(12) United States Patent
Warren et al.

(10) Patent No.: US 8,722,402 B2
(45) Date of Patent: May 13, 2014

(54) ARTIFICIAL IMMUNE SYSTEM: METHODS OF USE

(75) Inventors: William L Warren, Orlando, FL (US); Heather Fahlenkamp, Cleveland, OK (US); Russell Higbee, Orlando, FL (US); Anatoly Kachurin, Orlando, FL (US); Conan Li, Los Altos, CA (US); Mike Nguyen, Orlando, FL (US); Robert Parkhill, Orlando, FL (US); Guzman Sanchez-Schmitz, Orlando, FL (US); Darrell J. Irvine, Arlington, MA (US); Gwendalyn J. Randolph, New York, NY (US); Nir Harcohen, Brookline, MA (US); Bruce Torbett, Encinitas, CA (US)

(73) Assignees: Sanofi Pasteur Vaxdesign Corporation, Orlando, FL (US); Mount Sinai School of Medicine, New York, NY (US); The Whitehead Institute, Cambridge, MA (US); Massachusetts Institute of Technology, Cambridge, MA (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/608,579

(22) Filed: Sep. 10, 2012

(65) Prior Publication Data

US 2013/0078656 A1  Mar. 28, 2013

Related U.S. Application Data

(60) Continuation of application No. 12/725,698, filed on Mar. 17, 2010, now Pat. No. 8,288,159, which is a division of application No. 11/116,234, filed on Apr. 28, 2005, now Pat. No. 7,855,074.

(60) Provisional application No. 60/565,846, filed on Apr. 28, 2004, provisional application No. 60/643,175, filed on Jan. 13, 2005.

(51) Int. Cl.
*C12N 5/08* (2006.01)
*C12N 5/00* (2006.01)
*C12N 5/02* (2006.01)

(52) U.S. Cl.
USPC .......................... 435/373; 435/375; 435/377

(58) Field of Classification Search
None
See application file for complete search history.

(56) References Cited

U.S. PATENT DOCUMENTS

| | | |
|---|---|---|
| 5,008,116 A | 4/1991 | Cahn |
| 5,160,490 A | 11/1992 | Naughton et al. |
| 5,354,686 A | 10/1994 | Haberman |
| 5,562,910 A | 10/1996 | Daynes et al. |
| 5,725,856 A | 3/1998 | Hudziak et al. |
| 5,739,001 A | 4/1998 | Brown et al. |
| 5,750,329 A | 5/1998 | Quinn et al. |
| 6,177,282 B1 | 1/2001 | McIntyre |
| 6,274,378 B1 | 8/2001 | Steinman et al. |
| 6,479,064 B1 | 11/2002 | Atala |
| 6,541,225 B1 | 4/2003 | Li |
| 6,835,550 B1 | 12/2004 | Estell et al. |
| 2002/0155108 A1 | 10/2002 | Barbera-Guillem et al. |
| 2003/0109042 A1 | 6/2003 | Wu et al. |
| 2003/0147923 A1 | 8/2003 | Klaviniskis |
| 2003/0199006 A1 | 10/2003 | Britz et al. |
| 2003/0207287 A1 | 11/2003 | Short |
| 2004/0009943 A1 | 1/2004 | Semple et al. |
| 2004/0109876 A1 | 6/2004 | Yamamoto et al. |
| 2004/0234510 A1 | 11/2004 | Mochitate |
| 2005/0191743 A1 | 9/2005 | Wu et al. |
| 2005/0229264 A1 | 10/2005 | Chang et al. |
| 2005/0282148 A1 | 12/2005 | Warren et al. |
| 2006/0078540 A1 | 4/2006 | Warren et al. |
| 2006/0105454 A1 | 5/2006 | Son et al. ............. 435/325 |
| 2006/0270029 A1 | 11/2006 | Warren et al. |
| 2006/0275270 A1 | 12/2006 | Warren et al. |
| 2007/0015136 A1 | 1/2007 | Sanchez-Schmitz et al. |
| 2007/0141552 A1 | 6/2007 | Warren et al. |
| 2007/0154956 A1 | 7/2007 | Warren et al. |
| 2007/0178076 A1 | 8/2007 | Drake et al. |
| 2007/0218054 A1 | 9/2007 | Sukumar et al. |
| 2008/0008653 A1 | 1/2008 | Tew et al. |
| 2009/0011455 A1 | 1/2009 | Warren et al. |
| 2009/0104221 A1 | 4/2009 | El Shikh et al. |
| 2009/0117581 A1 | 5/2009 | Warren et al. |

FOREIGN PATENT DOCUMENTS

| | | |
|---|---|---|
| EP | 0358506 | 9/1989 |
| EP | 1013668 | 6/2000 |
| EP | 1437147 | 9/2002 |
| EP | 1970444 | 12/2006 |
| JP | 3-10674 | 1/1991 |

(Continued)

OTHER PUBLICATIONS

Ansel, et al., "A Chemokine-Driven Positive Feedback Loop Organizes Lymphoid Follicles", Nature, vol. 406, pp. 309-314 (2000).

(Continued)

*Primary Examiner* — Michail Belyavskyi

(74) *Attorney, Agent, or Firm* — Roylance, Abrams, Berdo & Goodman LLP

(57) ABSTRACT

The present invention relates to methods of constructing an integrated artificial immune system that comprises appropriate in vitro cellular and tissue constructs or their equivalents to mimic the normal tissues that interact with vaccines in mammals. The artificial immune system can be used to test the efficacy of vaccine candidates in vitro and thus, is useful to accelerate vaccine development and testing drug and chemical interaction with the immune system.

30 Claims, 63 Drawing Sheets

(56) References Cited

FOREIGN PATENT DOCUMENTS

| | | |
|---|---|---|
| JP | 8-507860 | 8/1996 |
| WO | 94/20142 | 9/1994 |
| WO | WO 99/12972 | 3/1999 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 2004/031361 | 4/2004 |
| WO | WO 2004/101773 | 11/2004 |
| WO | WO 2005/013896 | 2/2005 |
| WO | WO 2005/072088 | 8/2005 |
| WO | WO 2005/104755 | 11/2005 |
| WO | WO 2007/075979 | 7/2007 |
| WO | WO 2007/106559 | 9/2007 |
| WO | WO 2007/108835 | 9/2007 |
| WO | WO 2007/146267 | 12/2007 |

OTHER PUBLICATIONS

Aydar et al. (2005) *J. Immunol.* 174, 5358-5366.
Badylak, S.F. et al., "*Small Intestinal Submucosa: A Substrate for in vitro Cell Growth*," J. Biomater. Sci. Polymer Edn. (1998), vol. 9, No. 8, pp. 863-878.
Bai et al., "*Generation Of Dendritic Cells From Human Bone Marrow Mononuclear Cells: Advantages From Clinical Applications In Comparison To Peripheral Blood Monocyte Derived Cells*," International Journal of Oncology, (2002), 20(2), pp. 247-253.
Banchereau, et al., "Dendritic Cells and the Control of Immunity", Nature, vol. 392, pp. 245-252 (1998).
Banchereau, et al., "Immunobiology of Dendritic Cells", Annu. Rev. Immunol., vol. 18, pp. 767-811 (2000).
Baumgarth, "A Two-Phase Model of B-Cell Activation", Immunological Review, vol. 176, pp. 171-180 (2000).
Benbrook et al., "Organotypic cultures represent tumor microenvironment for drug testing," Drug Discovery Today: Disease Models, 3(2), pp. 143-148 (2005).
Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).
Birkness et al., A Tissue Culture Bilayer Model To Study the Passage of *Neisseria meningitidis*, Infection and Immunity, Feb. 1995, p. 402-409, vol. 63, No. 2.
Birkness et al., An In Vitro Tissue Culture Bilayer Model To Examine Early Events in *Mycobacterium tuberculosis* Infection, Infection and Immunity, Feb. 1999, p. 653-658, vol. 67, No. 2.
Bogdan, et al., "Fibroblasts as Host Cells in Latent Leishmaniosis", J. Exp. Med., vol. 191, pp. 2121-2129 (2000).
Boni et al. (2006) *Eur. J. Immunol.* 36, 3157-3166.
Brandtzaeg, P. et al., "*Mucosal B Cells: Phenotypic Characteristics, Transcriptional, Regulation, and Homing Properties*," Immunological Reviews (2005), vol. 206, pp. 32-63.
Bromelow, K. V. et al., "*Whole Blood Assay For Assessment Of The Mixed Lymphocyte Reaction*," Journal of Immunological Methods, (2001), 247(1-2), pp. 1-8.
Büchele, S. et al., "*Presentation of Tetanus Toxoid To Autologous T Cells By Dendritic Cells Generated From Human Blood. Improved Specificity With Dendritic Cells Generated Without Fetal Calf Serum*," Advances in Experimental Medicine and Biology, (1997), vol. 417, pp. 233-237.
Buchler et al. (2003) *Vaccine*, 21, 877-882.
Butcher, et al., "Lymphocyte Trafficking and Regional Immunity", Advances in Immunology, vol. 72, pp. 209-253 (1999).
Castro, et al., "Spleen-Derived Stromal Cells. Adhesion Molecules Expression and Lymphocyte Adhesion to Reticular Cells", Eur. J. Cell. Biol., vol. 74, 321-328 (1997).
Caux et al. (1995) *J. Immunol.* 155, 5427-5435.
Cayeux et al. (1999) *Eur. J. Immunol.* 29, 225-234.
Chen, et al., "A Film Tension Theory of Phagocytosis", Journal of Colloid and Interface Science, vol. 190, pp. 118-133 (1997).
Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).
Clayton et al., Clin. Exp. Immunol., 2003, v.132, p. 174-179.
Crivellato, et al., "Stromal Cell Organisation in the Mouse Lymph Node. A Light and Electron Microscopic Investigation Using the Zinc Iodide—Osmium Technique", J. Anat., vol. 190, pp. 85-92 (1997).
Cyster, "Chemokines and the Homing of Dendritic Cells to the T Cell Areas of Lymphoid Organs", J. Exp. Med. vol. 189, No. 3, pp. 447-450 (1999).
Cyster, et al., "Follicular Stromal Cells and Lymphocyte Homing to Follicles", Immunological Reviews, vol. 176, pp. 181-193 (2000).
D'Amico et al., Blood 92:207-214 (1998).
Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).
Denkbas, et al., "Magnetic Chotosan Microspheres: Preparation and Characterization", Reactive & Functional Polymers, vol. 50, pp. 225-232 (2002).
Dubey et al. (2005) *J. Clin. Endocrin & Met.*, 90, 247-255.
Dubois, et al., "Dendritic Cells Enhance Growth and Differentiation of CD40-Activated B Lymphocytes", J. Exp. Med., vol. 185, pp. 941-951 (1997).
Dubois et al., J. Leukocyte Biology, 1999, v.66, p. 224-230.
Edelman et al, A Cultureal Renaissance: In Vitro Cell Biology Embraces Three-Dimensional Context. Exp Neurol. 2005, vol. 192, pp. 1-6.
El Shikh, M. et al., "Follicular Dendritic Cells Stimulated By Collagen Type I Develop Dendrites And Networks In Vitro," Cell and Tissue Research, (2007), 329(1), pp. 81-89.
Forster, et al., "CCR7 Coordinates the Primary Immune Response by Establishing Functional Microenvironments in Secondary Lymphoid Organs", Cell., vol. 99, pp. 23-33 (1999).
Fransson, et al., "Culture of Human Epidermal Langerhans Cells in a Skin Equivalent", British Journal of Dermatology, vol. 139, pp. 598-604 (1998).
Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).
Fulcher, et al., "B-Cell Activation Versus Tolerance—The Central Role of Immunoglobulin Receptor Engagement and T-Cell Help", Int. Rev. Immunol., vol. 15, pp. 33-52 (1997).
Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).
Furuyama, A. et al., "*Assembly of Basement Membrane in vitro by Cooperation Between Alveolar Epithelial Cells and Pulmonary Fibroblasts*," Cell Structure and Function (1997), vol. 22, pp. 603-614.
Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).
Gansuvd et al., Human Immunol., 2003, v.64, p. 427-439.
Garside, et al., "Visualization of Specific B and T Lumphocyte Interactions in the Lymph Node", Science, vol. 281, pp. 96-99 (1998).
Gergel, et al., "Activation of Endothelium by *Borrelia burgdorferi* In Vitro Enhances Transmigration of Specific Subsets of T Lymphocytes", Infection and Immunity, vol. 69, pp. 2190-2197 (2001).
Gretz, et al., "Cords, Channels, Corridors and Conduits: Critical Architectural Elements Facilitating Cell Interactions in the Lymph Node Cortex", Immunological Reviews, vol. 156, pp. 11-24 (1997).
Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

(56) References Cited

OTHER PUBLICATIONS

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).
Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).
Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).
Gunzer, et al., "Antigen Presentation in Extracellular Matrix: Interactions of T Cells with Dendritic Cells are Dynamic, Short Lived, and Sequential", Immunity, vol. 13, pp. 323-332 (2000).
Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).
Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).
Jenkins, et al., "In Vivo Activation of Antigen-Specific CD4 T Cells", Annu. Rev. Immunol., vol. 19, pp. 23-45 (2001).
Junt, et al., "Antiviral Immune Responses in the Absence of Organized Lymphoid T Cell Zones in *plt/plt* Mice", The Journal of Immunology, vol. 168, pp. 6032-6040 (2002).
Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).
Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).
Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).
Khademhosseini et al., "Microscale Technologies for Tissue Engineering and Biology," Proc. Natl. Acad. Sci. USA, vol. 103, pp. 2480-2487 (2006).
Kim et al., "*Three-Dimensional Tissue Culture Models In Cancer Biology,*" Seminars in Cancer Biology, (2005), 15(5), pp. 365-377.
Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).
Kosco, M. H. et al., "*Folicular Dendritic Cell-Dependent B-Cell Proliferation And In Vitro Germinal Center,*" Lymphatic Tissues In Vivo Immune Responses, (1991), pp. 687-690.
Kosco, M. H. et al., "*Follicular Dendritic Cell-Dependent Adhesion and Proliferation Of B Cells In Vitro,*" Journal of Immunology, (1992), 148(8), pp. 2331-2339.
Kosco, M. H. et al., "*Follicular Dendritic Cells And Germinal Center Formation In-Vitro,*" Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).
Kosco-Vilbois, "Are Follicular Dendritic Cells Really Good for Nothing", Nature Reviews Immunology, vol. 3, pp. 764-769 (2003).
Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).
Larsson, et al., "Requirement of Mature Dendritic Cells for Efficient Activation of Influenza A-Specific Memory CD8 + T Cells", The Journal of Immunology, vol. 165, pp. 1182-1190 (2000).

LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).
Levenberg, S. et al., "*Advances In Tissue Engineering,*" Current Topics In Developmental Biology, (2004), vol. 61, pp. 113-134.
Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).
Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).
Manna, P. et al., "Differentiation And Functional Maturation Of Human CD14<+> Adherent Peripheral Blood Monocytes By Xenogeneic Endothelial Cells: Up-Regulation Of Costimulation Cytokine Generation, And Toll-Like Receptors," Transplantation, (2002), 74(2), pp. 243-252.
Matsumoto, et al., "Affinity Maturation Without Germinal Centres in Lymphotoxin-α-Deficient Mice", Nature, vol. 382, pp. 462-466 (1996).
Mebius, "Organogenesis of Lymphoid Tissues", Nat. Rev. Immunol, vol. 3, pp. 292-303 (2003).
Mellman, et al., "Dendritic Cells: Specialized and Regulated Antigen Processing Machines", Cell, vol. 106, pp. 255-258 (2001).
Miller, et al., "Two-Photon Imaging of Lymphocyte Motility and Antigen Response in Intact Lymph Node", Science, vol. 296, pp. 1869-1873 (2002).
Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).
Moser et al. (2000) Nature Immunol. 1, 199-205.
Nakamura, M. et al., "*Expression of Leptin in Two-layered Culture of Gastric Mucous Cells and Fibroblasts: Effect of Helicobacter pylori Attachment,*" Aliment Pharmacol Ther. (2004), vol. 20, suppl. 1, pp. 125-130.
Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-1,*" Microvascular Research (2003), vol. 66, pp. 102-112.
Neves, A. R. et al., "*Dendritic Cells Derived From Metastatic Cancer Vaccinated With Allogeneic Dendritic Cell-Autologous Tumor Cell Hybrids Express More CD86 and Induce Higher Levels Of Interferon-Gamma In Mixed Lymphocyte Reactions,*" Cancer Immunology and Immunotherapy, (2005), 54(1), pp. 61-66.
Oehler et al. (2000) Ann. Hematol., 79, 355-362.
Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.
Parker, "T Cell-Dependent B Cell Activation", Annu. Rev. Immunol., vol. 11, pp. 331-360 (1993).
Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).
Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).
Podgrabinska, et al., "Molecular Characterization of Lymphatic Endothelial Cells", Proc. Natl. Acad. Sci. U.S.A., vol. 99, No. 25, pp. 16069-16074 (2002).
Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.
Poznansky, et al., "Efficient Generation of Human T Cells From a Tissue-Engineered Thymic Organoid", Nature Biotechnology, vol. 18, pp. 729-734 (2000).

(56) References Cited

OTHER PUBLICATIONS

Qu, et al., "Autocrine Type I IFN and Contact with Endothelium Promote the Presentation of Influenza A Virus by Monocyte-Derived APC", The Journal of Immunology, vol. 170, pp. 1010-1018 (2003).
Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).
Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).
Randolph, et al., "Differentiation of Monocytes into Dendritic Cells in a Model of Transendothelial Trafficking", Science, vol. 282, pp. 480-483 (1998).
Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).
Randolph, et al., "Role of Tissue Factor in Adhesion of Mononuclear Phagocytes to and Trafficking Through Endothelium in Vitro", Blood, vol. 92, pp. 4167-4177 (1998).
Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).
Razanajaona, et al., In Vitro Triggering of Somatic Mutation in Human Naïve B Cells, The Journal of Immunology, vol. 159, pp. 3347-3353 (1997).
Regnier, et al., "Integration of Langerhans Cells into a Pigmented Reconstructed Human Epidermis", The Journal of Investigative Dermatology, vol. 109, No. 4, pp. 510-512 (1997).
Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).
Roos et al. (2005) *Expert Opin. Drug Metab. Toxicol.* 1, 187-202.
Rot, "In Situ Binding Assay for Studying Chemokine Interactions with Endothelial Cells", Journal of Immunological Methods, vol. 273, pp. 63-71 (2003).
Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).
Safarik, et al., "Use of Magnetic Techniques for the Isolation of Cells", Journal of Chromatography B, vol. 722, pp. 33-53 (1999).
Santini et al. (2000) *J. Exp. Med.* 191, 1777-1788.
Sarradell et al. (2003) *Vet. Pathol.*, 40, 395-404.
Seguin, R. et al., "*Human Brain Endothelial Cells Supply Support For Monocyte Immunoregulartory Functions,*" Journal of Neuroimmunology, (2003), 135(1-2), pp. 96-106.
Sieben, et al., "Comparison of Different Particles and Methods for Magnetic Isolation of Circulating Tumor Cells", Journal of Magnetism and Magnetic Materials, vol. 225, pp. 175-179 (2001).
Simmingskoeld et al., Scand. J. Immunol. 7:233-238 (1978).
Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).
Skibinski, et al., "The Role of Hepatocyte Growth Factor and Its Receptor *c-met* in Interactions Between Lymphocytes and Stromal Cells in Secondary Human Lymphoid Organs", Immunology, vol. 102, pp. 506-514 (2001).
Soderberg, O. et al., "*The Human Follicular Dendritic Cell Line FDC-1 Binds Immune Complexes And Promotes Somatic Hypermutation,*" Blood, (2001), 98(11 part 2), pp. 40b.
Sprent, et al., "Antigen-Induced Selective Recruitment of Circulating Lymphocytes", Cellular Immunology, vol. 2, pp. 171-181 (1971).
Stoll, et al., "Dynamic Imaging of T Cell-Dendritic Cell Interactions in Lymph Nodes", Science, vol. 296, pp. 1873-1876 (2002).
Stuart, et al., "The Human Reticular Cell: Morphology and Cytochemistry", J. Pathol, vol. 103, pp. 41-47 (1971).
Suematsu, et al., "Generation of a Synthetic Lymphoid Tissue-Like Organoid in Mice", Nature Biotechnology, vol. 22, No. 12, pp. 1539-1545 (Dec. 2004).
Tan et al. (2005) *J. Leuk. Biol.* 78, 319-324.
Tarte et al., Leukemia, vol. 14, 2000, abstract p. 2182.
Tew et al. (2001) *Trends Immunol.* 22, 361-367.
Tew, J. G. et al., "*Follicular Dendritic Cells As Accessory Cells,*" Immunological Reviews, (1990), No. 117, pp. 185-211.
Tew, J.G. et al., "*Follicular Dendritic Cells and Presentation of Antigen and Costimulatory Signals to B Cells,*" Immunological Reviews (1997), vol. 156, pp. 39-52.
Thompson, H.G. et al., "*A Three-dimensional in vitro Model of Angiogenesis in the Airway Mucosa,*" Pulmonary Pharmacology & Therapeutics (2007), vol. 20, pp. 141-148.
Toyama, et al., "Memory B Cells Without Somatic Hypermutation are Generated from Bcl 6 Deficient B Cells", Immunity, vol. 17, pp. 329-339 (2002).
Transwell® Permeable Supports Selection and Use Guide, Corning Corp., pp. 1-12 (2009).
Tsunoda, R. et al., "*Follicular Dendritic Cells In Vitro Modulate The Expression Of Fas and Bcl-2 on Germinal Center B Cells,*" Cell and Tissue Research, (2000), 299(3), pp. 395-402.
Tsunoda, R. et al., "*Human Follicular Dendritic Cells In Vitro And Follicular Dendritic-Cell-Like Cells,*" Cell and Tissue Research, (1997), 288(2), pp. 381-389.
Van Den Berg, et al., "Localization of β 1 Integrins and Their Extracellular Ligands in Human Lymphoid Tissues", American Journal of Pathology, vol. 143, pp. 1098-1110 (1993).
Weppler et al., Modulation of Endotoxin-Induced Neutrophil Transendothelial Migration by Alveolar Epithelium in a Defined Bilayer Model, *Experimental Lung Research* 32:10, 455-482 (2006).
West, et al., "Polymeric Biomaterials with Degradation Sites for Proteases Involved in Cell Migration", Macromolecules, vol. 32, pp. 241-244 (1999).
Wu et al. (2008) *J. Immunol.* 180, 281-290.
Wu, Y. et al., "*Influence Of Follicular Dendritic Cells And Primed T Cells On Somatic Hypermutation In In Vitro Germinal Centers,*" Journal of Immunology, (2006), 176(suppl. S), pp. S235-S236.
Zhang, S. et al., "*Growth Factors Secreted by Bronchial Epithelial Cells Control Myofibroblast Proliferation: An in vitro Co-culture Model of Airway Remodeling in Asthma,*" Laboratory Investigation (1999), vol. 79, No. 4, pp. 395-405.
International Search Report—PCT/US2007/083795.
International Search Report—PCT/US2008/056720.
International Search Report—PCT/US08/70107a.
International Search Report—PCT/US06/048959.
International Search Report—PCT/US07/014826.
International Search Report—PCT/US08/69172.
International Search Report—PCT/US07/013745.
International Search Report—PCT/US05/14444.
International Search Report—PCT/US06/43563.
International Search Report—PCT/US06/43712.
International Search Report—PCT/US07/006532.
International Search Report—PCT/US07/006571.
International Search Report—PCT/US07/013871.
International Search Report—PCT/US06/049128.
International Search Report—PCT/US08/70107b.
Dynal (Norway): http://www.invitrogen.com/.
Agowa GMBH (Germany): http://agowade/contentsframes/magneticseparation/particle.html.
http://www.xcyte.com.
Protocol for anti-CD3 Activation of T-Cells from E-Bioscience (San Diego, CA): http://www.ebioscience..com/ebioscience/appls/AC145.htm.
Takeuchi et al., CCL21 Chemokine Regulates Chemokine Receptor CCR7 Bearing Malignant Melanoma Cells, Clin. Cancer Res. 10:2351-2358 (2004).

(56) References Cited

OTHER PUBLICATIONS

Katakai et al., Lymph Node Fibroblastic Reticular Cells Construct the Stromal Reticulum via Contact with Lymphocytes, J. Exp. Med. 200(6):783-795 (2004).

Caux et al., Functional CD40 on B Lymphocytes and Dendritic Cells, Res. Immunol. 145:235-239 (1994).

Inaba et al., Clustering of Dendritic Cells, Helper T Lymphocytes, and Histocompatible B Cells During Primary Antibody Response In vitro, J. Exp. Med. 160:858-876 (1984).

Grouard et al., Regulation of Human B Cell Activation by Follicular Dendritic Cell and T Cell Signals, Curr. Topic Microbiol. Immunol. 201:105-117 (1995).

Warren, W., The Front-End of Vaccine Manufacturing: Getting Good Candidates from the Get-Go. Workshop on Science and Technology in North American Rapid Vaccine Manufacturing, Jan. 26, 2007.

Hashimoto, K., et al., Direct Observation and Analysis of Spatiotemporal Dynamics of Individual Living Monocyte During Transendothelial Migration. Atherosclerosis 177(1):19-27 (Nov. 2004).

Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.

Higbee, R., et al., An Immunologic Model for Rapid Vaccine Assessment—A Clinical Trial in a Test Tube. ALTA 37, Suppl. 1, 19-27 (2009).

Price, N. et al., Genome-scale microbial in silico models: the constraints-based approach, Trends Biotechnol., 2003, vol. 21, No. 4, pp. 162-169.

Nagashima, U. et al., The cutting edge of molecular simulation What can molecular simulation tell us? From micro to macro—From the nature of the molecule to the nature of assembly, Chemical Engineering, 2003, vol. 67, No. 8, pp. 432-435.

Tomita, M. et al., Computer Simulation of Cells, CICSJ Bull., 2001, vol. 19, No. 6, pp. 2-6.

Sun, W.D. et al., An artificial immune system architecture and its applications, IECE Trans. Fundamentals, 2003, vol. E86-A, No. 7, pp. 1858-1868.

Guidry, A.J. et al., A bovine mammary endothelial/epithelial cell culture model of the blood/milk barrier, Can. J. Vet. Res., 1998, vol. 62, pp. 117-121.

Hauser, A. et al., Chemotactic responsiveness toward ligands for CXCR3 and CXCR4 is regulated on plasma blasts during the time course of a memory immune response, J. Immunol., 2002, vol. 169, pp. 1277-1282.

Alt, C. et al., Functional expression of the lymphoid chemokines CCL19 (ELC) and CCL21 (SLC) at the blood-brain barrier suggests their involvement in G-protein-dependent lymphocyte recruitment into the central nervous system during experimental autoimmune encephalomyelitis, Eur. J. Immunol., 2002, vol. 32, pp. 2133-2144.

Ferrero et al. CD14+ CD34+ Peripheral Blood Mononuclear Cells Migrate Across Endothelium and Give Rise to Immunostimulatory Dendritic Cells. J. Immunol. 160:2675-2683 (1998).

Figure 7
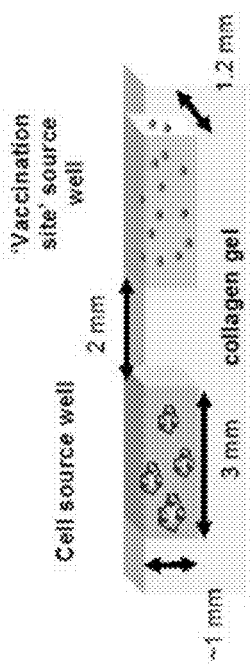
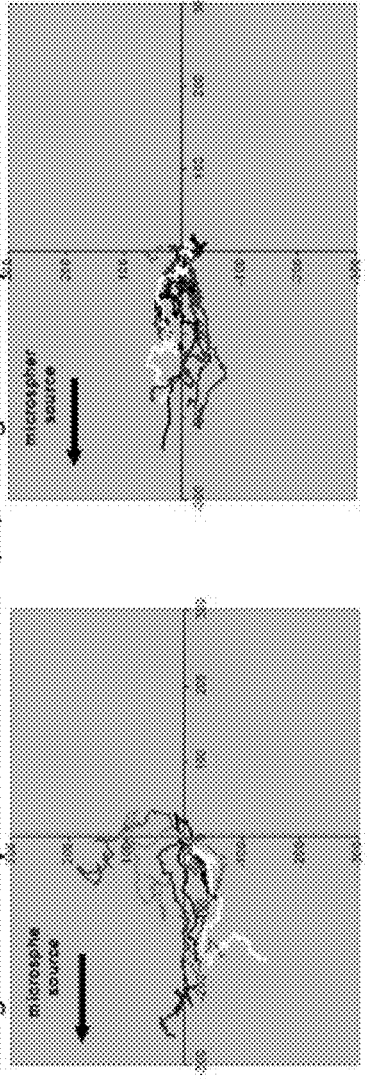

Figure 9: Mockup of Digitally Printed Lymph Node (Left) and a Retinal Image of Vasculature (right)

Figure 22
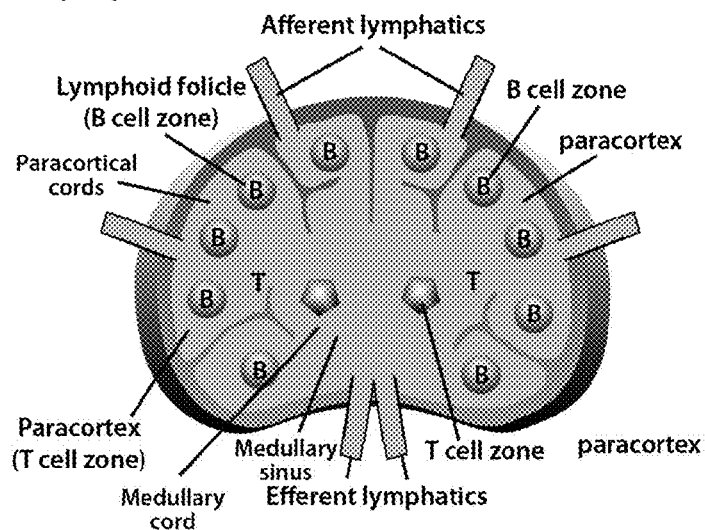
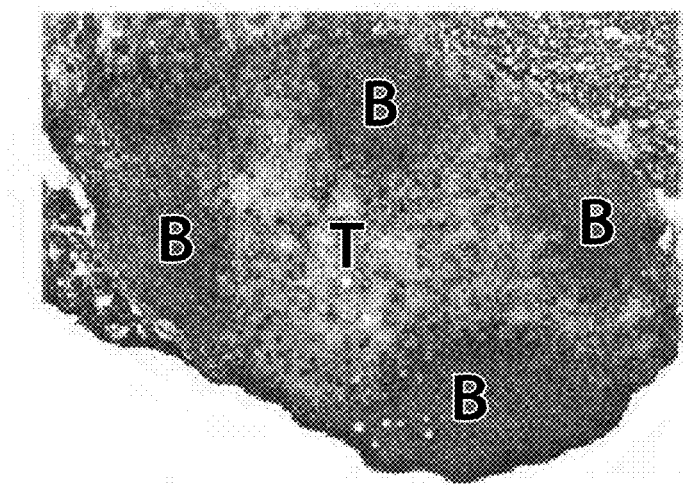

B cells on Cytodex - 1 microcarriers (Amersham),
bright field microscopy (left) and fluorescence (right).

T cells on Cytopore - 1 microcarriers (Amersham), bright field (left) and fluorescence (right).

T cells on LN ECM / Protasan in-house microcarriers, confocal fluorescence image.

Figure 34
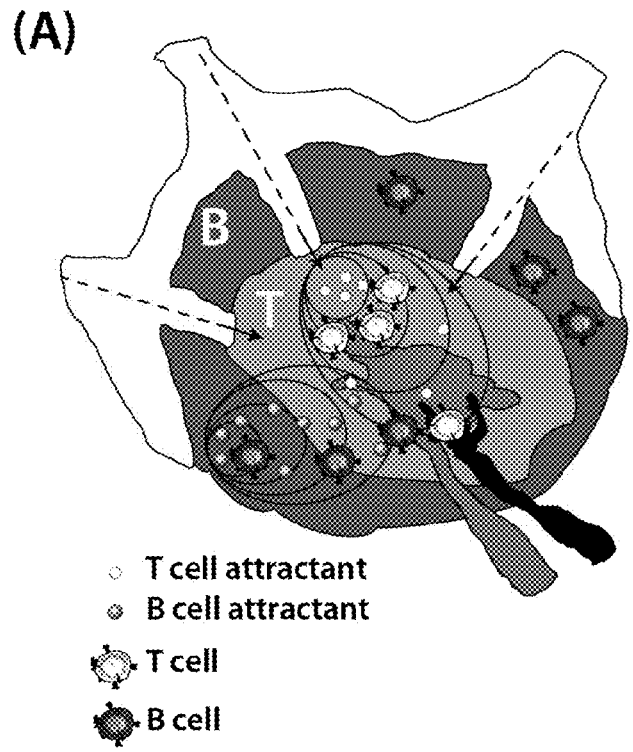
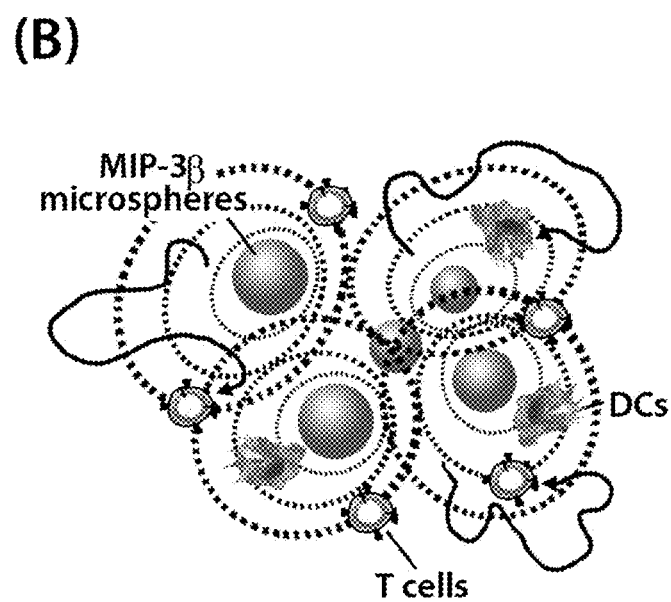

Laminate Microchannel

Microfluidic bioreactor and optical diagnostics on microfluidic backplane

Removing the beads occurs in the reverse order

**Laser-machined integrated optical waveguides:
$n_1$ represents the refractive index of the
waveguide core, $n_2$ is the cladding index**

Magnetic Bead-Assisted ELISA of the Humoral Antibodies in the LTE Compartment

Hypothetical Hyper-Conjugate of the Anti-CD3 Magnetic Bead with CD4+ and CD8+ T-cells and Fluorescent Anti-CD4 and Anti-CD8 Antibodies.

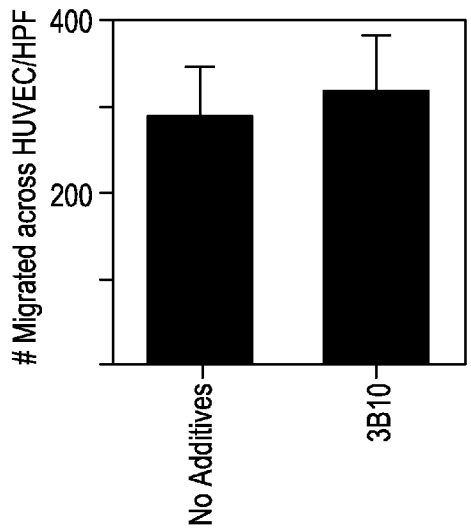
Figure 45A
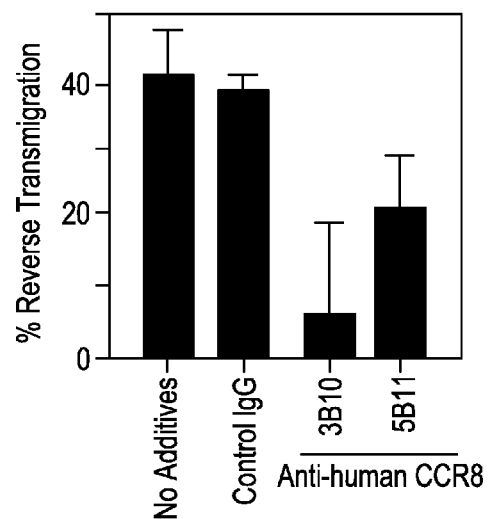
Figure 45C
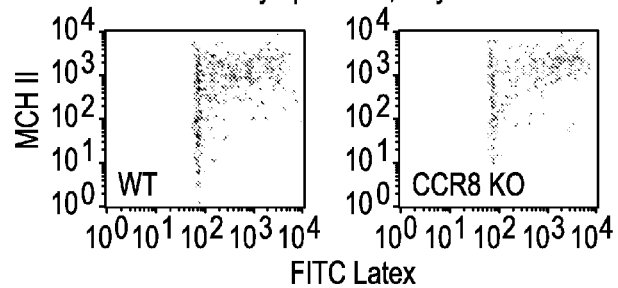
Figure 45D
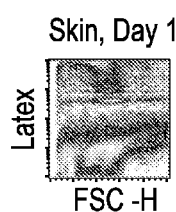
Figure 45B
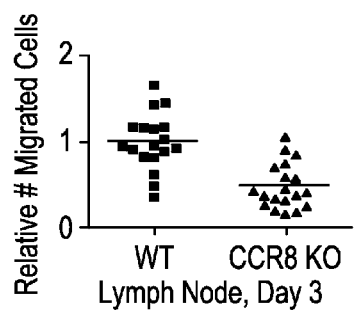
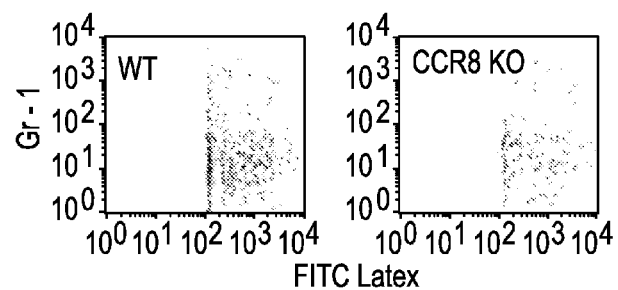

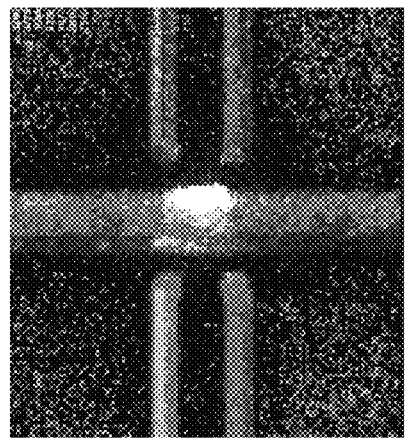
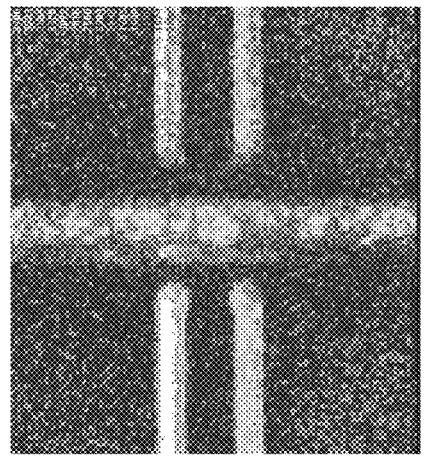
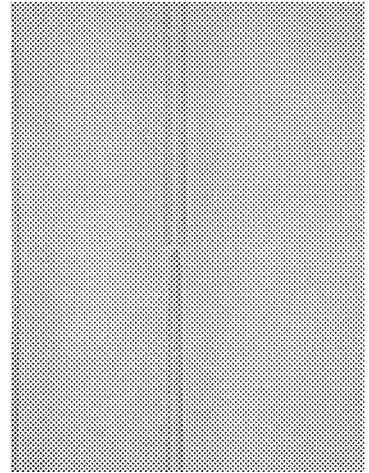
Figure 46

Other side overlay
(top with fibroblasts just beneath ECs)

One side overlay
(bottom of amnion, away from fibroblasts)

Figure 47G
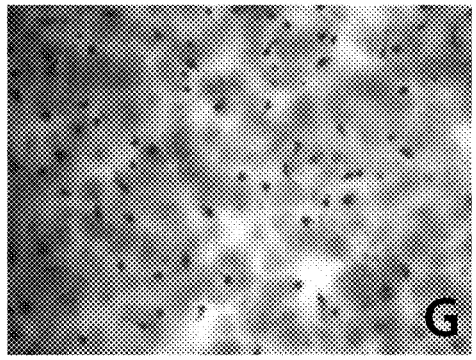
Figure 48
Plan view of Integrated Bioreactor that shows Micromachined Blood Vascular and Lymphatic Pathways with High Contact Area Beneath the VS and LTE ETCs
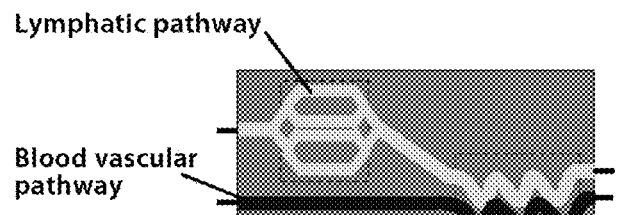
PDMS microfluidic layer
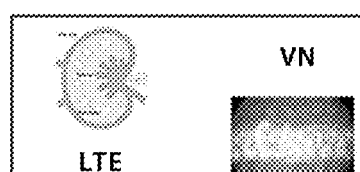
BAT structural layer

Cross-Sectional View of Direct Deposition in the AIS Device

A Cross-Sectional View of an Example Bioreactor

Transparent gas-permeable polymer

BAT-printed structural layer

PDMS micro-fluidic layer

Fabrication of 3-Layer Planar Waveguide

Figure 57
(A)
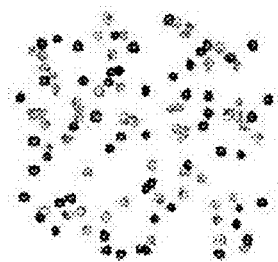
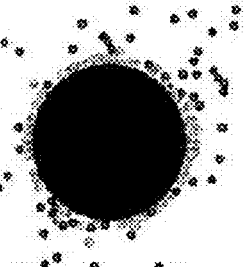
(B)
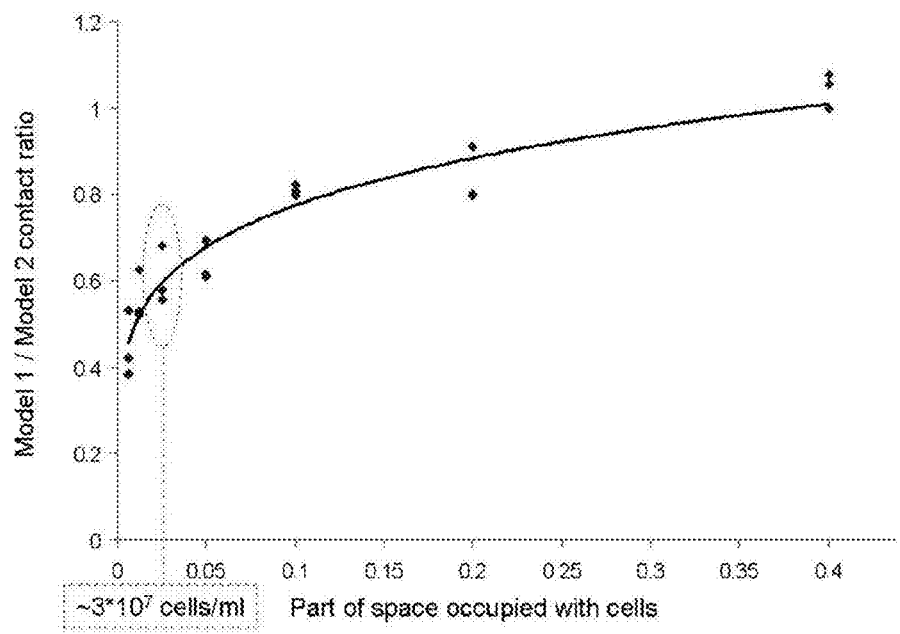
Ratio of contact frequencies for Model 1 towards Model 2

Before Staining, 10x     After Staining, 10x     After Staining, 10x

Contrast Mode, 40x     CMFDA Live Cells, 40x     Ethidium Homodimer-1
                                                 Dead Cells, 40x Figure 59
Bioreactor construction with collagen membranes on rings and support matrix
(A) Polycarbonate Bioreactor Design
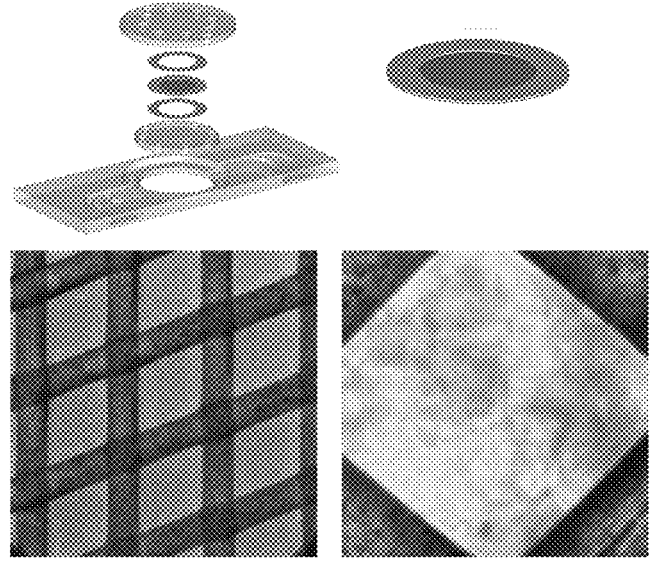
(B)
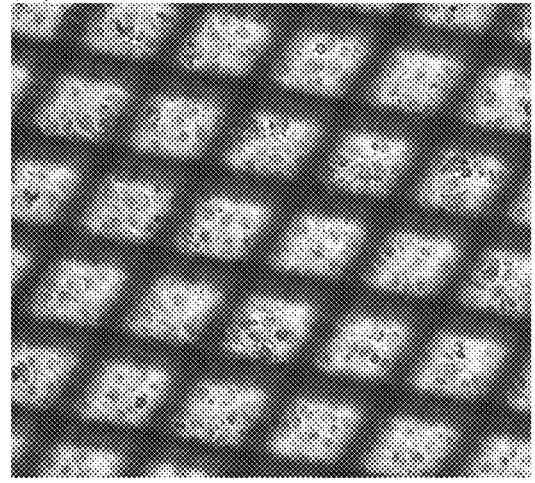

(C)

Ring structures showing variable methods of attachment of membranes for VS in the bioreactor Figure 66 shows HuVEC cells on the culture plate with a bead of Devon two-part epoxy applied and polymerized in place prior to seeding.

ARTIFICIAL IMMUNE SYSTEM: METHODS OF USE

CROSS REFERENCE TO RELATED APPLICATIONS

This application is a continuation of U.S. application Ser. No. 12/725,698, filed Mar. 17, 2010, which issued as U.S. Pat. No. 8,288,159 on Oct. 16, 2012, which is a divisional of U.S. application Ser. No. 11/116,234, filed Apr. 28, 2005, which issued as U.S. Pat. No. 7,855,074 on Dec. 12, 2010 and which claims priority from U.S. Provisional Application Ser. No. 60/565,846, filed Apr. 28, 2004 and U.S. Provisional Application Ser. No. 60/643,175 filed Jan. 13, 2005. The entirety of each of these applications is incorporated herein by reference.

STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.

BACKGROUND OF THE INVENTION

1. Field of the Invention

The present invention is directed to a method for constructing an integrated artificial human tissue and, in particular, construction of an integrated human immune system for in vitro testing of vaccines, adjuvants, immunotherapy candidates, cosmetics, drugs, biologics, and other chemicals. The artificial immune system is useful for assessing the interaction of substances with the immune system, and thus can be used to accelerate and improve the accuracy of vaccine, drug, biologic, immunotherapy, cosmetic, and chemical development.

2. Background of the Technology

The development and biological testing of human vaccines has traditionally relied on small animal models, such as mouse and rabbit models, and then non-human primate models. However, such small animal models are expensive and non-human primate models are both expensive and precious.

The mammalian immune system uses two general adaptive mechanisms to protect the body against environmental pathogens. When a pathogen-derived molecule is encountered, the immune response is highly activated to ensure protection against that pathogenic organism.

The first mechanism is the non-specific (or innate) inflammatory response. The innate immune system appears to recognize specific molecules that are present on pathogens but not on the body itself.

The second mechanism is the specific or acquired (or adaptive) immune response. Innate responses are fundamentally the same for each injury or infection. In contrast, acquired responses are custom tailored to the pathogen in question. The acquired immune system evolves a specific immunoglobulin (antibody) response to many different molecules present in the pathogen, called antigens. In addition, a large repertoire of T cell receptors is sampled for their ability to bind processed forms of the antigens bound to MHC class I and II on antigen-presenting cells (APCs), such as dendritic cells (DCs).

The immune system recognizes and responds to structural differences between self and non-self proteins. Proteins that the immune system recognizes as non-self are referred to as antigens. Pathogens typically express large numbers of highly complex antigens. Acquired immunity has specific memory for antigenic structures; repeated exposure to the same antigen increases the response, which increases the level of induced protection against that particular pathogen.

Acquired immunity is mediated by specialized immune cells called B and T lymphocytes (or simply B and T cells). B cells produce and mediate their functions through the actions of antibodies. B cell-dependent immune responses are referred to as "humoral immunity," because antibodies are detected in body fluids. T cell-dependent immune responses are referred to as "cell mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Advances in the design, creation and testing of more sophisticated vaccines have been stalled for several reasons. First, only a small number of vaccines can be tested in humans, because, understandably, there is little tolerance for harmful side effects in healthy children exposed to experimental vaccines. With the exception of cancer vaccine trials, this greatly limits the innovation that can be allowed in the real world of human clinical trials. Second, it remains challenging to predict which epitopes are optimal for induction of immunodominant CD4 and CD8 T cell responses and neutralizing B cell responses. Third, small animal testing, followed by primate trials, has been the mainstay of vaccine development; such approaches are limited by intrinsic differences between human and non-human species, and ethical and cost considerations that restrict the use of non-human primates. Consequently, there is a slow translation of basic knowledge to the clinic, but equally important, a slow advance in the understanding of human immunity in vivo.

The artificial immune system (AIS) of the present invention can be used to address this inability to test many novel vaccines in human trials by instead using human tissues and cells. The AIS enables rapid vaccine assessment in an in vitro model of human immunity. The AIS provides an additional model for testing vaccines in addition to the currently used animal models.

Attempts have been made in modulating immune system. See, for example, U.S. Pat. No. 6,835,550 B1; U.S. Pat. No. 5,008,116; Suematsu et al., *Nat. Biotechnol.*, 22, 1539-1545 (2004); and US Patent Publication No. 2003/0109042.

Nevertheless, none of these publications describes or suggests the AIS, which comprises a vaccine site (VS), a lymphoid tissue equivalent (LTE), a lymphatic and blood vascular network equivalent, and the use of AIS for assessing the interaction of substances with the immune system.

SUMMARY OF THE INVENTION

The present invention provides an integrated system of the functionally equivalent human tissues for testing vaccines, adjuvants, drugs, biologics, cosmetics, and other chemicals in vitro. One aspect of the invention relates to a method for constructing a functionally equivalent tissue using blueprints that design, as opposed to fabricate, morphologically equivalent constructs. Functional equivalency to the human immune system is achieved by building three engineered tissue constructs (ETCs), housed in a modular miniaturized immunobioreactor system.

Another aspect of the invention relates to a method of constructing an artificial immune system. The method comprises: (1) designing and blueprinting three functionally equivalent immunologic engineered tissues that form the basis for the human immune system (vaccination site, lymphoid tissue equivalent, and lymphatic/vascular highways); (2) providing real time communication pathways between the engineered immunological constructs; and (3) integrating the engineered tissues and immunological constructs in a modular immunobioreactor to form the basis for an in vitro AIS for rapid vaccine assessment.

Approaches to construction of the artificial immune system include the construction of engineered immunological tissues, populated with a reproducible cell source, with a particular focus on dendritic cells (DCs). The ability to optimize the spatial juxtaposition and temporal relationships between the cells, biomolecules, and scaffolds via a directed self assembly process moves far beyond existing two dimensional (2D) Petri dish cell cultures into reproducible three dimensional, (3D) heterogeneous, biologically viable constructs, much more similar to the in vivo situation.

The artificial immune system of the present invention further relates to the method of using AIS for (1) modulating the immune system in a subject to eliminate various of infectious diseases and pathogens (2) rapid comparison of vaccine or immunotherapy formulations; (3) rational dissection of vaccine or immunotherapy action to identify "rate limiting steps" to focus further development; and (4) systematic determination of optimal formulations to create better vaccines that promote more rapid and long lived protection.

The predictive value of such an engineered tissue construct equivalent immune system is superior to current in vitro models of human immunity.

BRIEF DESCRIPTION OF THE FIGURES

FIGS. 7A-7D demonstrate in vitro control of monocyte and dendritic cell chemotaxis. FIG. 7A is a schematic representation of the experimental design. FIG. 7B shows the movement of monocyte-derived DCs in the absence of chemokine. FIGS. 7C and 7D show the movement of monocyte-derived DCs and moncytes, respectively, towards the vaccination site source well.

FIG. 10A shows pictures of vascular endothelial cells grown on 3D constructs of fibronectin-coated collagen. FIG. 10B is a schematic diagram showing the stages of monocyte behavior in such a 3D culture. FIG. 10C shows demonstrates that monocytes can be infected with influenza to measure activation of IFN$\gamma$ induction and expansion during recall responses in T cells from adults previously infected with flu.

FIGS. 22A and 22B show the structure of a lymph node. FIG. 22A is a schematic view of a lymph node. FIG. 22B is a histologic section of a lymph node; B cells are stained blue and T cells are stained brown (Abbas, et al., Cellular and Molecular Immunology (W. B. Saunders Co., New York, N.Y.) (2000)).

FIG. 23A is an image of toluidine blue-stained HUVEC cells on a collagen cushion. FIG. 23B is a higher magnification of FIG. 23A. FIG. 23C shows a high density of newly applied peripheral blood mononuclear cells (PBMCs) on the layer of HUVEC. FIG. 23D shows a focal plane below the HUVEC cells, within the collagen matrix, 45 minutes after the application of PBMCs. Cells in focus are within the collagen and are easily distinguished between HUVEC and surface PBMCs. FIG. 23E is an image of CMFDA labeling showing cell viability and position of live cells within the collagen cushion. FIG. 23F shows transmigration of PBMCs into collagen cushions without or with the presence of Zymosan. Phase contrast, and CMFDA labeling was done to determine cell placement within the cushion. Z-stack images were taken through the entire cushion to determine the numbers of cells within the cushion and those that had undergone transmigration. FIG. 23G shows increased numbers of transmigrated cells remained in the cushion in the presence of Zymosan as compared to cushions with no Zymosan. FIG. 23H is a comparison of depth of penetration in the presence of Zymosan versus no Zymosan. FIG. 23I is a schematic diagram of this experimental design.

FIG. 24A shows a schematic of overall lymph node structure and a scanning electron micrograph of ECM structure in the T zone (Gretz, et al., Immunol. Rev. 156:11-24 (1997)). FIG. 24B is a confocal immunofluorescence image of stromal cells lining the reticular network (Gretz, et al., J. Exp. Med. 192:1425-1440 (2000)). Collagen fibers of the network are stained red, while reticular fibroblasts are stained green. FIG. 24C shows fiber organization in an in vitro type I collagen gel (Kaldjian, et al., Int. Immunol. 13:1243-1253 (2001); Friedl, et al., Eur. J. Immunol., 28:2331-2343 (1998)).

FIG. 34 shows a lymphoid tissue equivalent (LTE). (A) maintenance of T cell and B cell areas in vivo. (B) schematic of T cell-DC localization to T cell areas of the LTE via MIP-3β-releasing microspheres.

FIG. 45 shows the role of CCR8 in DC migration: role for CCR8 immigration. Panels A and C are graphs showing migration of monocytes in the absence or presence anti-CCR8 mAb 3B 10. Panels B and D show monocyte conversion into DCs in vivo using green fluorescent latex microspheres injected into the skin of CCR8-deficient and age/sex-matched wild-type C57BL/6 counterparts.

FIG. 46 shows images of an ultra-short pulse laser micromachined planar optical waveguides integrated into microfluidic channel. Left panel: Tapered port for fiber optic coupling. Middle panel: microfluidic channel intersection of planar waveguide (source off). Right panel: microfluidic channel intersection of planar waveguide (source on, entering from right).

Panels A and B are immunohistological staining of respective endothelial monolayers. Blue=endothelial nuclei; Green=CD31 staining to identify confluent endothelial junctions; Red=acting to identify actin bundles in all cell types and particularly fibroblasts. Some fibroblasts are visible beneath the vascular endothelium. Panel C is immunohistological staining of fibroblasts within the amnion. Panel D is immunohistological staining of monocytes that have traversed the blood endothelium and moved toward the second endothelial monolayer. Panel E is hematoxylin staining of an endothelial monolayer. Panels F and G show that monocytes penetrate deeply into the amniotic membrane toward the second endothelial monolayer.

FIG. 48 is a plan view of an example integrated bioreactor that shows micromachined blood vascular and lymphatic pathways with high contact area (left panel) beneath the VS and LTE ETCs (right panel).

Figure 49:
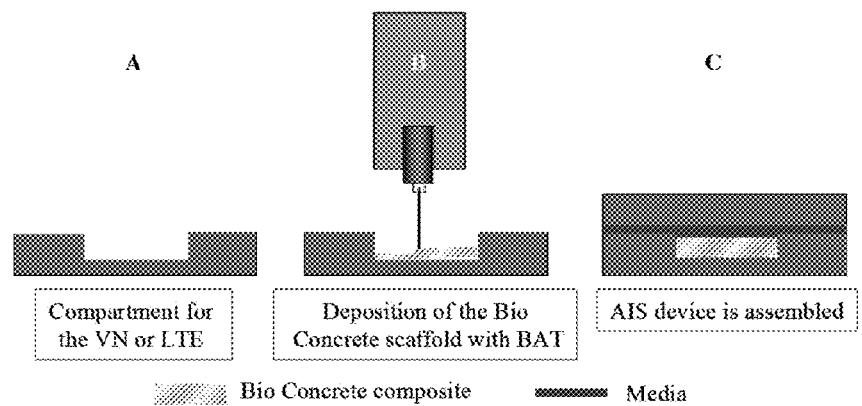

FIG. 49 shows cross sectional views of direct deposition in the AIS device. Various biomaterial structures can be incorporated as constituents of the artificial immune system (e.g., bio concrete, inverse hydrogel opal, colloidal particles, ECM gels, collagen gels, microcarriers). For example, a polymeric mesh rebar can be deposited layer by layer directly in the recessions of the VS and LTE areas. In such a design, it is preferred to have the lower plate of the AIS unit made of polyacrylate, polystyrene, or another transparent plastic sensitive to DM, to allow the mesh rebar to attach to the plate. In this embodiment, the surface is micro-patterned using KOH in a manner similar to the ESC scaffolds. Fibrin gel matrix bearing all necessary nutrients and cytokines can be used to coat the threads of the mesh as a thin film, leaving sufficient space for cell accommodation and motion.

Figure 50:
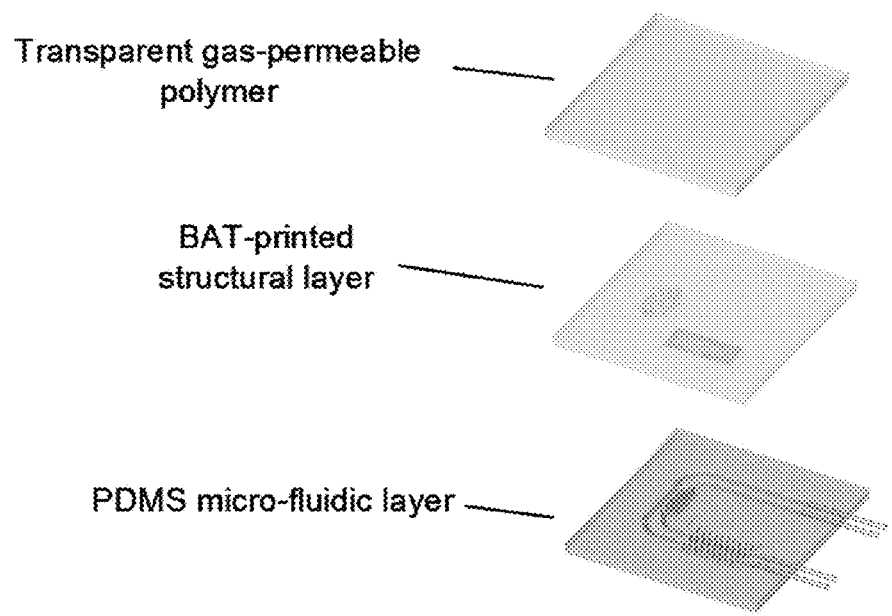

FIG. 50 shows an example microfluidic bioreactor in separate layers.

Figure 51:
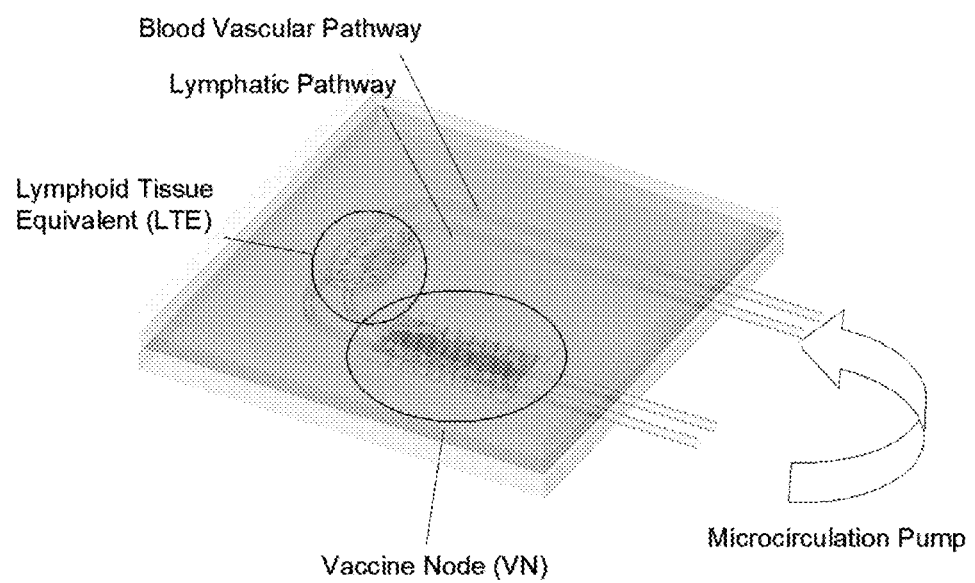

FIG. 51 shows an assembled microfluidic bioreactor.

Figure 52:
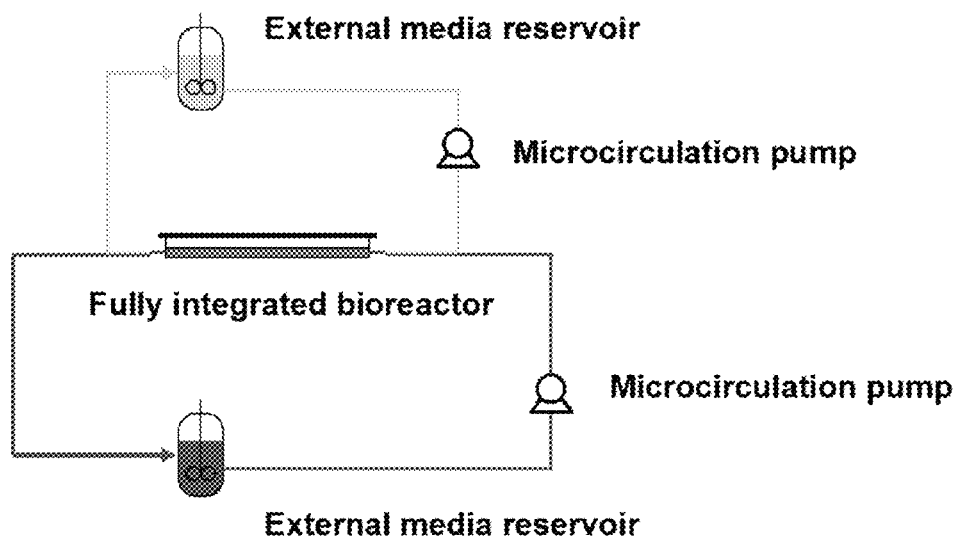

FIG. 52 is a schematic diagram of perfused bioreactor system with the associated external pumps for the lymphatic and blood vascular loops and external media reservoirs. The AIS bioreactor can be operated in either semi-batch or continuous mode.

Figure 53:
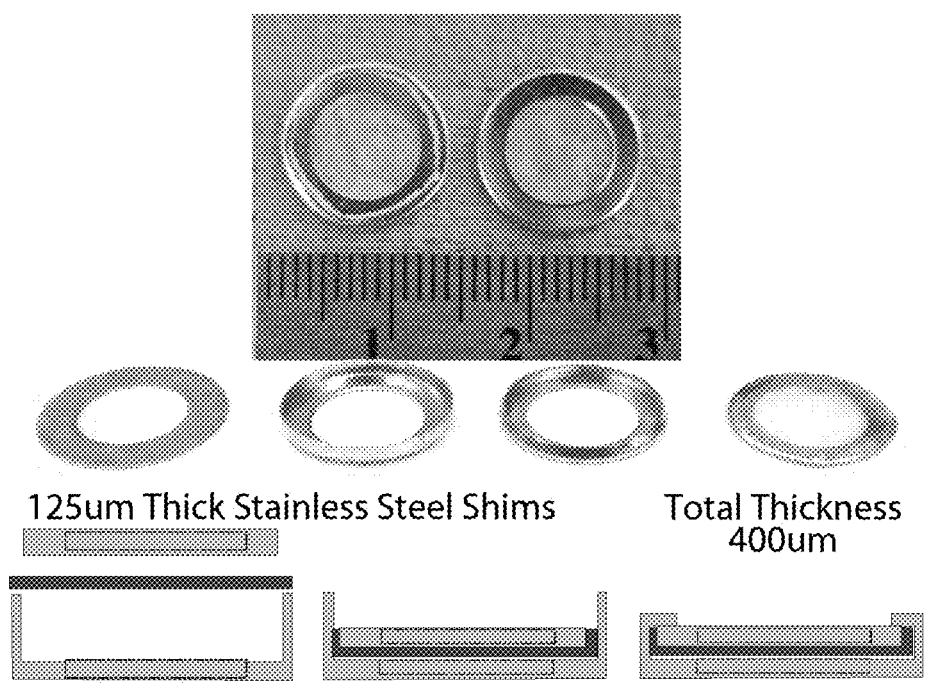

FIG. 53 shows membranes between thin metal (e.g., stainless steel) rings. Using such a crimping method, biological membranes can be supported without use of adhesives and can be pressed into a disk with thickness profile of about 400 µm or less.

Figure 54:
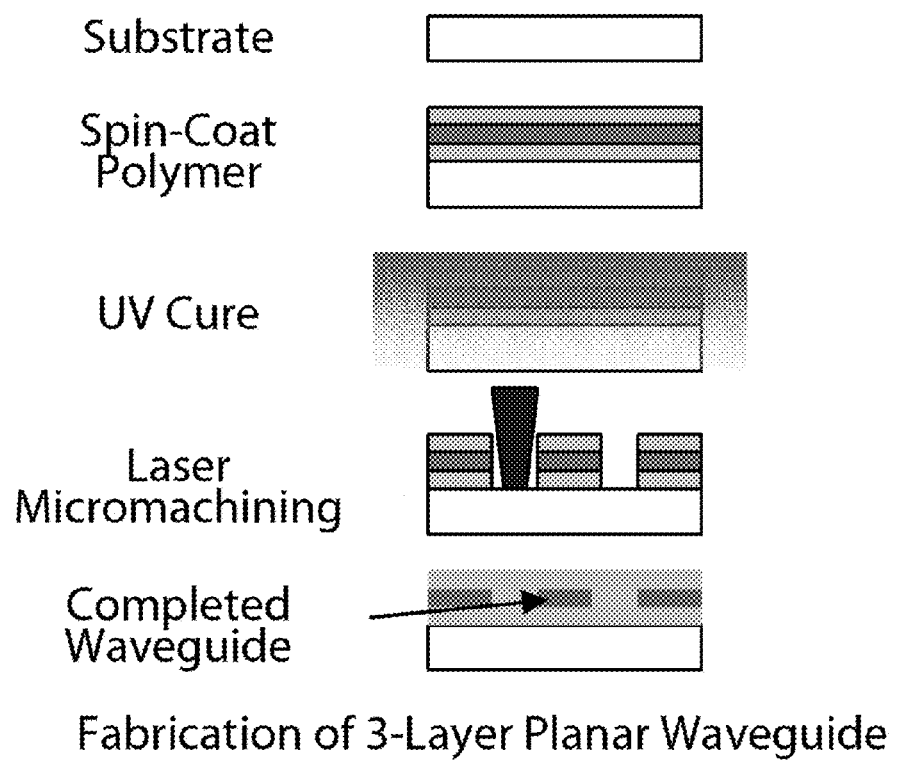

FIG. 54 is a schematic showing the fabrication of a 3-layer planar waveguide.

Figure 55:
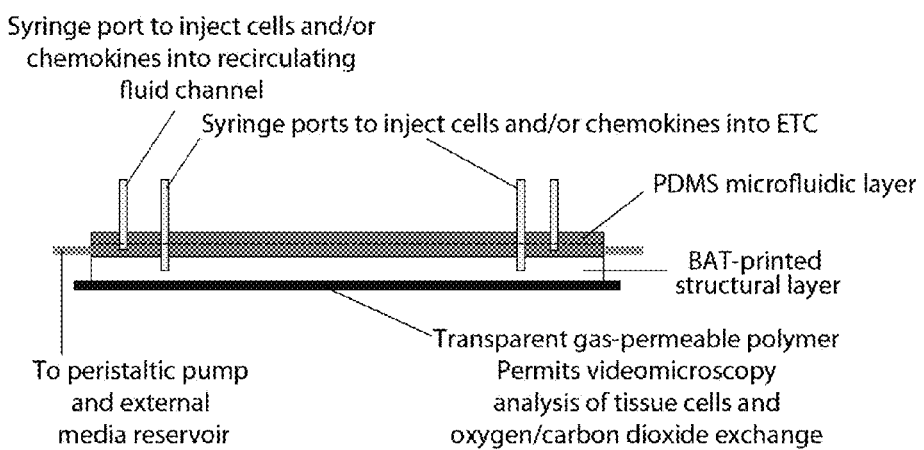

FIG. 55 shows an example device comprising a perfusion bioreactor, an ELISA chip with integrated optical waveguides, microfluidic backplane to connect and allow swapping of devices and microfluidic connectors for external pumps and reservoirs.

Figure 56:
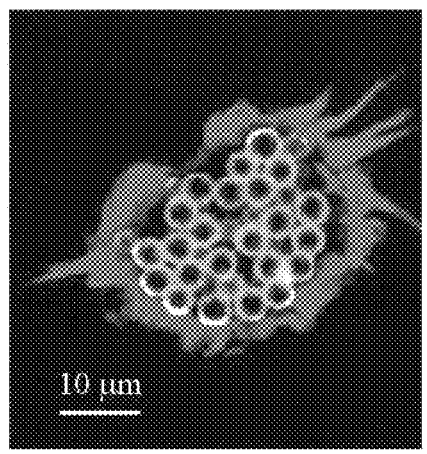

FIG. 56 shows phagocytosis of microparticles by a monocyte.

FIGS. 57(A) and (B) show kinetics in silico modeling of T and B interaction in LTE. FIG. 57(A) is the in silico 2D models of B and T cell interaction. Size of cell is 12 µm; size of carrier is 250 µm; speed of T cell is 12 µm/min; speed of B cell: 6 µm/min; B-T interaction time is 3 min; cell population density: $2.76 \times 10^7$/ml (1/40 space taken by cells); number of B cells are 65; and number of T cells are 65.

Figures 58A, 58B, 58C:
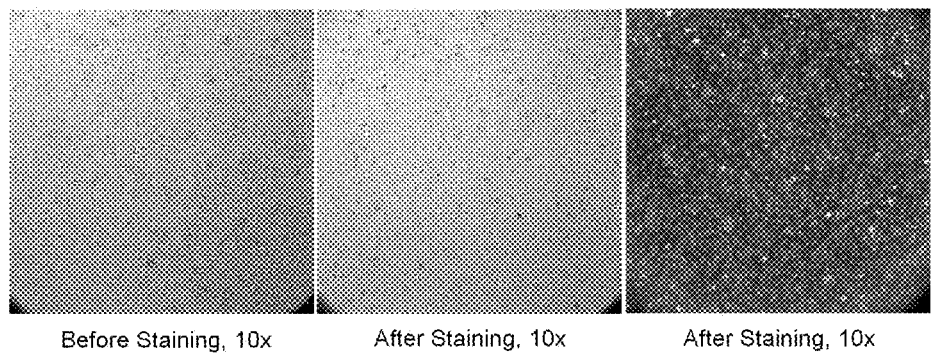
Figures 58D, 58E, 58F:
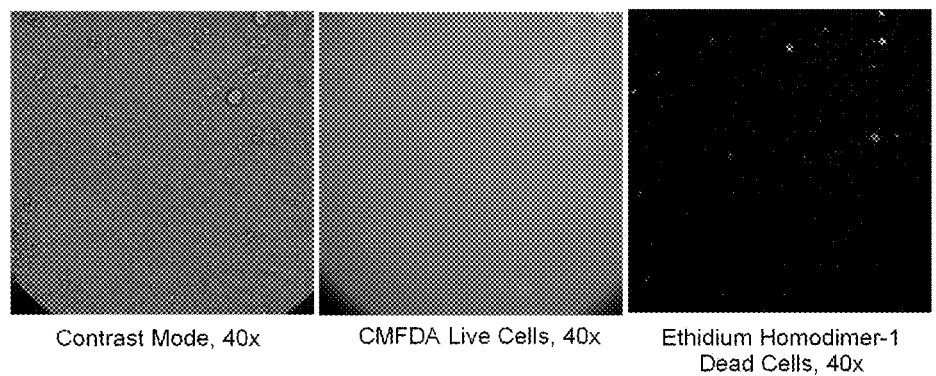

FIG. 58 shows characterization of the HUVEC endothelial cells in the collagen cushion. Panels A-C: HUVEC cells before (A) and after (B; C) staining with CMFDA to determine cell viability by epifluorescent illumination prior to application of PBMCs for migration studies. Panel D: characterization of HUVEC cells by phase contrast. Panels E and F, staining with CMFDA showing live cells (E) and with ethidium homodimer-1 showing dead cells (F).

Figure 59:
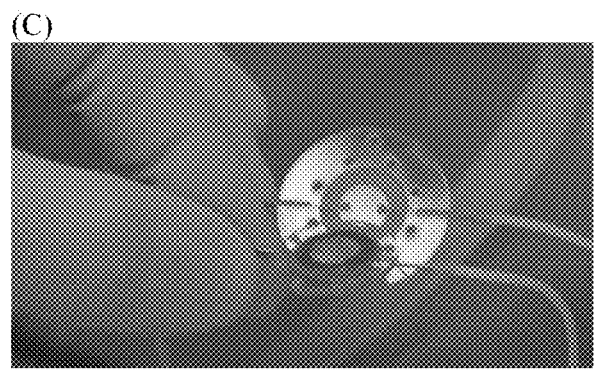

FIG. 59 shows an example bioreactor construction with collagen membranes on rings and support matrix. Panel A sows the bioreactor design. Panel B shows progression from the whole bioreactor to the level of the collagen matrix cushion within the mesh. Panel C shows the assembly of the bioreactor under sterile conditions, after the HUVEC cells have reached confluence on the collagen cushion. Once assembled, media flow is initiated.

Figure 60:
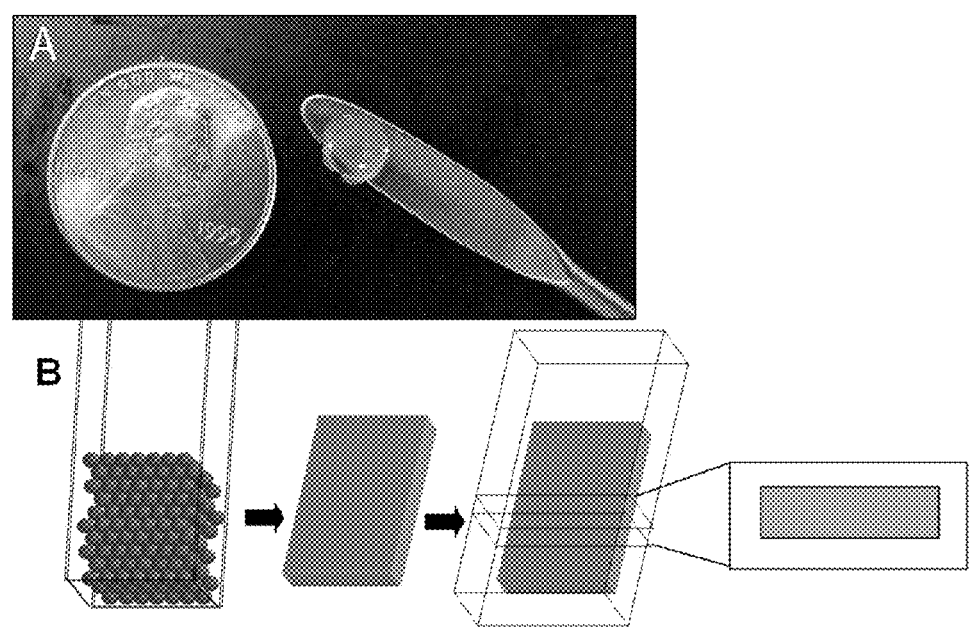

FIG. 60 shows the preparation of an inverse opal gel scaffold. Panel A: Inverse opal gel scaffolds can be prepared with arbitrary dimensions by the choice of mold for creating the colloidal crystal template. Shown is a photograph of a templated gel ~6 mm in diameter and ~2 mm tall, on the end of a spatula (coin for scale). Panel B: Gels of very precise thicknesses can be fabricated by templating gels, polymerizing additional gel material around the templated scaffold, and then slicing the bulk-gel-surrounded construct into arbitrary thin layers.

Figure 61:
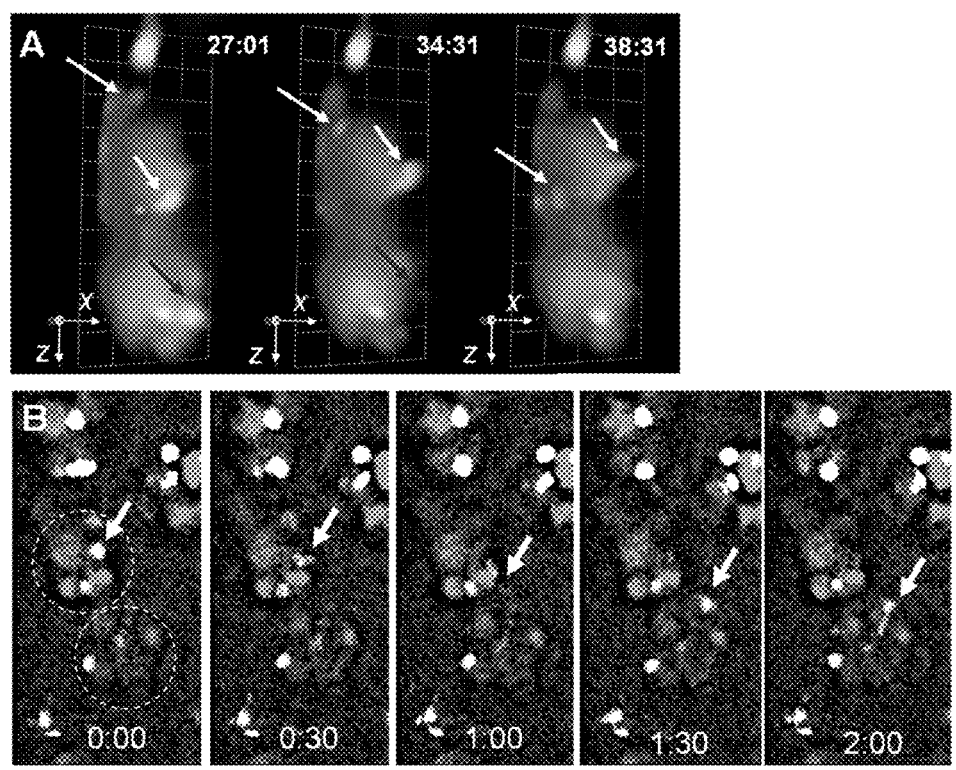

FIG. 61 shows T cell motility induction on inverse opal scaffolds. Panel A: 3D reconstruction of naive T cells (green) migrating over clusters of mature dendritic cells (red) within voids of the inverse opal scaffold. Times in the upper corners represent relative elapsed min:sec. Color-coded arrows track the position of several cells in the field of view. Panel B: Deconvolved 2D fluorescence image demonstrating the rapid trafficking of one naive T cells (green, marked with arrow) from one cluster of DCs to another (clusters identified with dotted lines in first frame), laterally through a window connecting two voids of the scaffold. Elapsed time as in panel (A).

Figure 62:
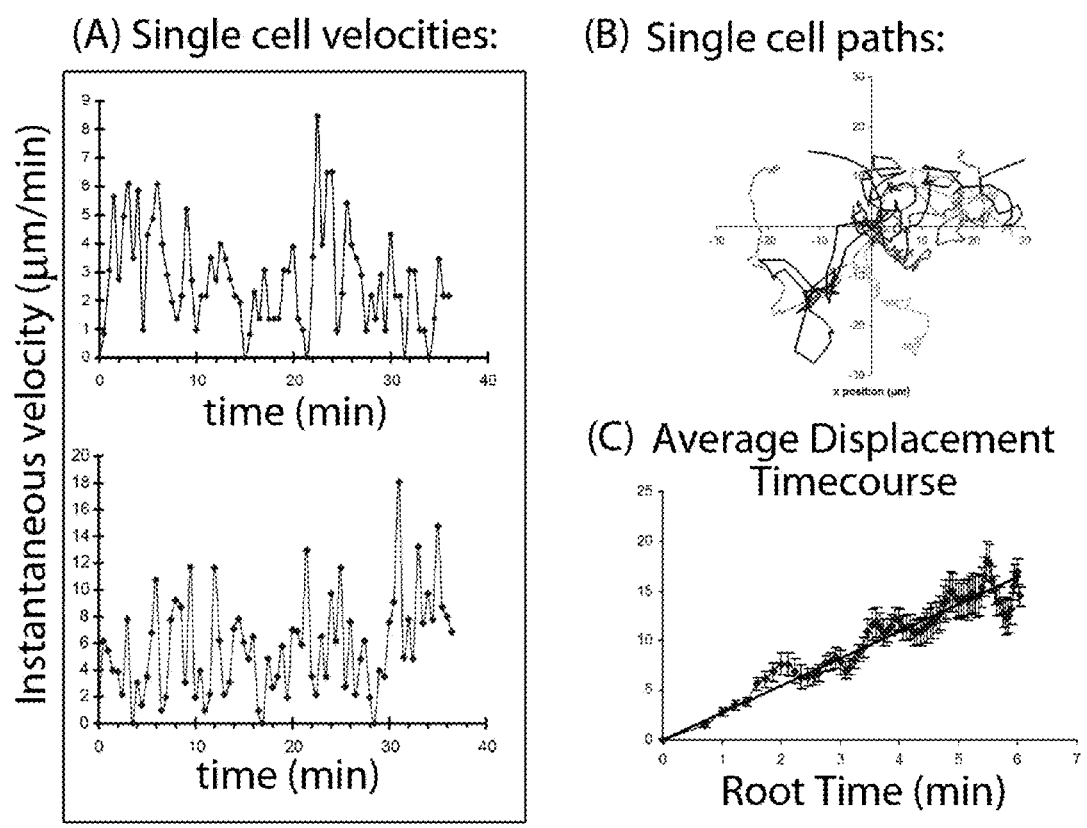

FIG. 62 shows quantitation of cell movement. Panel A: Single-cell instantaneous velocities of cells migrating in scaffolds vs. time. Panel B: 2D projections of single cell migration paths in x and y, with positions shown in microns, plotted over 30 min T cells show random migration within the scaffold, as observed in the lymph node T zone. Panel C: Mean displacement as a function of time for naive T cells in inverse opal scaffolds, co-cultured with mature dendritic cells.

Figure 63:
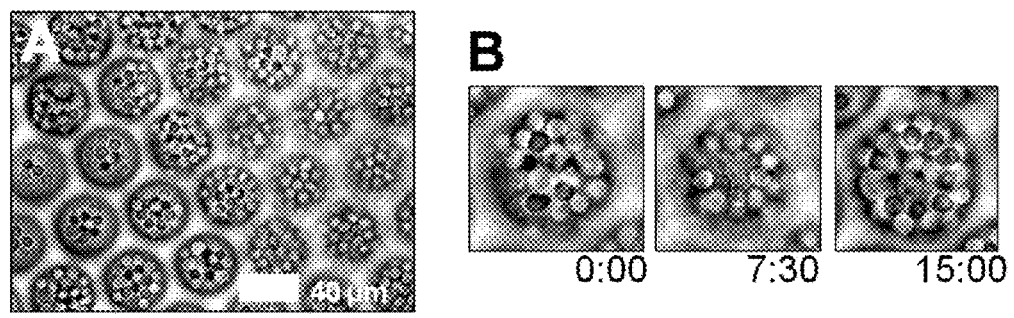

FIG. 63 illustrates that Cell-cell contact alone within scaffolds does not drive T cell migration. Naive OT-II CD4+ T cells cultured at lymph node-like cell densities in inverse opal scaffolds do not polarize or migrate. Panel A: overall view of a region of scaffold by bright field microscopy. Panel B: 3 time-lapse clips of cells within one void of the matrix. Times are elapsed min:sec.

Figure 64:
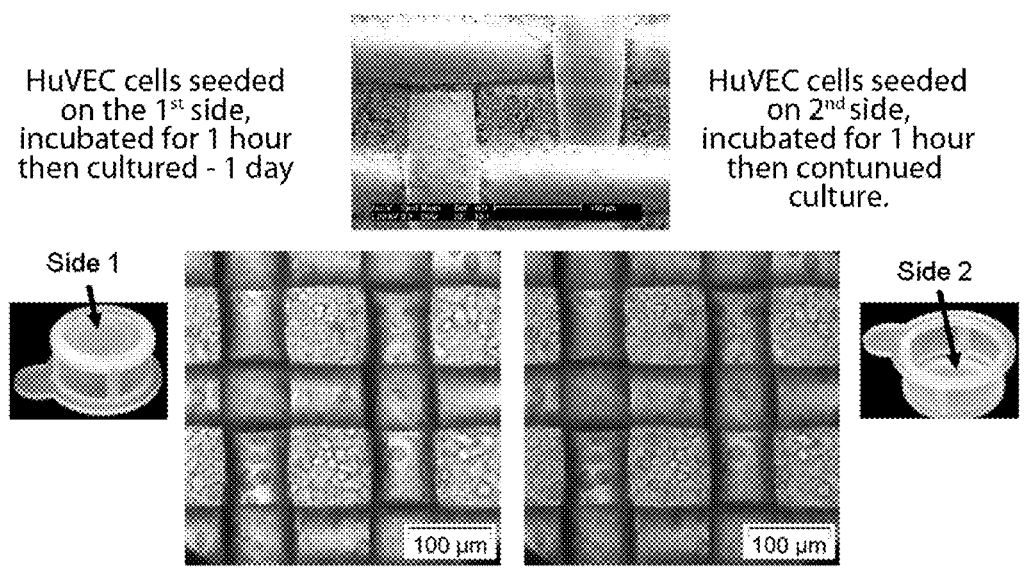

FIG. 64 shows HUVEC cells growing on protasan/collagen matrix on a nylon mesh. High-magnification SEM of the nylon membrane and interspersed Protasan/collagen matrix material is shown in the top image. Seeding of the primary layer of HUVEC cells was accomplished on an inverted membrane (left, Side 1), then 24 hours later, brought to an upright position (right, Side 2) where the second layer was applied. Phase contrast images of each plane of HUVEC cells is shown in the center two lower images, with the left being the first layer, and the right being the second layer applied.

Figure 65:
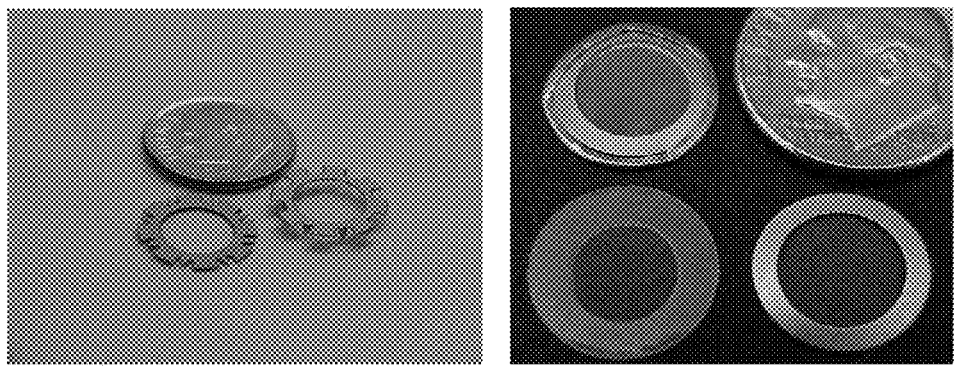

FIG. 65 shows pictures of ring structures showing variable methods of attachment of membranes for VS in the bioreactor. The left panel shows the spiked ring design used to hold 'wet' membrane structures such as amniotic or UBM naturally occurring ECM membranes. The right panel shows three methods used to attach 'dry' synthetic membranes to the ring structure. Top left (next to the left side of the dime) is crimped, bottom left is by laminating the membrane between two rings of the same material, and bottom right (below the dime) is glued.

Figure 66:
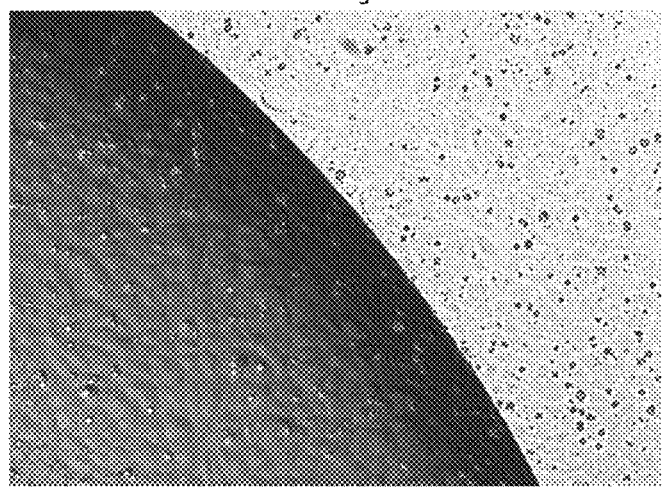

FIG. 66 shows HUVEC cells on the culture plate with a bead of Devon two-part epoxy applied and polymerized in place prior to seeding.

Figure 67:
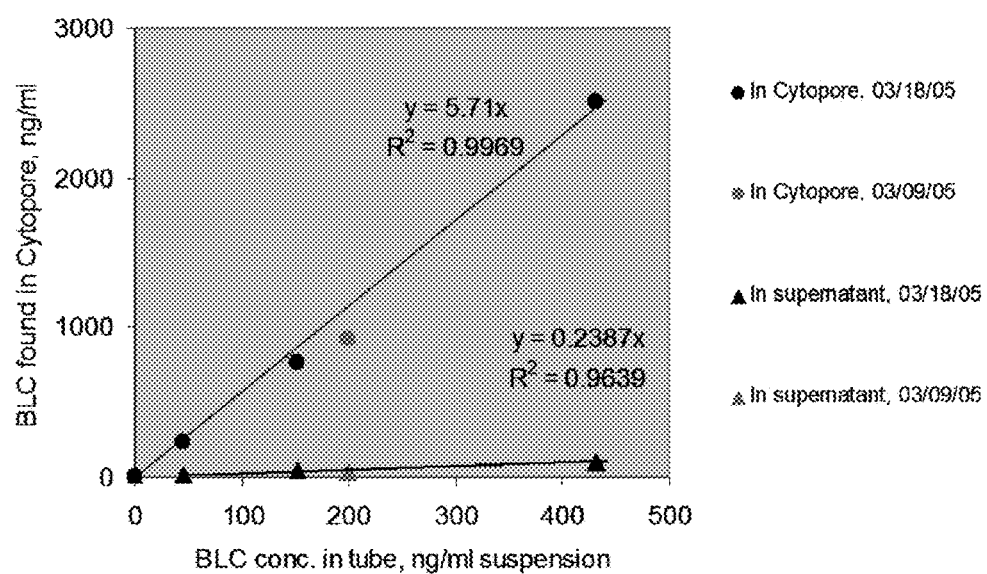

FIG. 67 is a sorption curve of Cytopore/heparin.

DETAILED DESCRIPTION OF THE INVENTION

A primary objective of the present invention is to provide an integrated human tissue, an integrated human immune system, for testing vaccines, immunotherapies, adjuvants, drugs, biologics, cosmetics, and other chemicals in vitro. One aspect of the invention relates to methods to construct an integrated human immune system model that comprise using appropriate in vitro cellular and tissue constructs or their equivalents to mimic the normal tissues that interact with vaccines in humans. Such an integrated platform of human tissues enables acceleration of vaccine development strategies and testing of drugs that interact with the immune system. Furthermore, it enables a reduction in animal testing and enables candidate vaccines to be re-engineered and retested at a fraction of the cost of animal studies and human trials.

Tissue engineering involves the development of synthetic materials or devices that are capable of specific interactions with cells and tissues. The constructs combine these materials with living cells to yield functional tissue equivalents. Tissue engineering involves a number of different disciplines, such as biomaterial engineering, drug delivery, recombinant DNA techniques, biodegradable polymers, bioreactors, stem cell isolation, cell encapsulation and immobilization, and the production of 2D and 3D scaffolds for cells. Porous biodegradable biomaterial scaffolds are required for the 3D growth of cells to form the tissue engineering constructs. There are several techniques to obtain porosity for the scaffolds, including fiber bonding, solvent casting/particulate leaching, gas foaming/particulate leaching, and liquid-liquid phase separation. These produce large, interconnected pores to facilitate cell seeding and migration. As used herein, the terms "tissue-engineered construct" or "engineered tissue construct" ("ETC") include any combination of naturally derived or synthetically grown tissue or cells, along with a natural or synthetic scaffold that provides structural integrity to the construct.

It is known that 3D biology is important to induce proper functionality of immunological ETCs (see, e.g., Edelman & Keefer, Exp. Neurol. 192:1-6 (2005). A principal approach to studying cellular processes is to culture cells in vitro. Historically, this has involved plating cells on plastic or glass supports. Cells grown on solid or filter support are referred as two dimensional (2D) cultures. Such 2D cultures on porous supports have been extremely useful for studying many aspects of biology. However, much more in vivo-like conditions can now be realized in 3D cultures. For example, many epithelial cells, both primary cultures and established lines, form complex epithelial structures when grown in 3D ECM.

Recently, in lymph nodes, it has been shown that 3D interstitial tissue matrix facilitates not only T cell migration toward an APC, but also supports motility upon cell-cell interaction. A 3D collagen matrix environment, because of its spatial architecture, provides traction for lymphocyte crawling, mimicking some structural features of the lymph node cortex. This provides experimental justification for the importance of a 3D environment in the constructs that comprise the in vitro immune system.

The differences between 2D and 3D microenvironments include that:
(1) in 2D cultures, cells experience unnatural, anisotropic, external cues from the artificial support, while in 3D cultures, cells are able to migrate on the ECM in all dimensions;
(2) in 2D cultures, the support (e.g., plastic, glass) is far more rigid than naturally occurring ECM;
(3) cells grown in 3D culture are more resistant to apoptosis, and
(4) proteins secreted by cells can better interact with and be organized by a 3D culture surrounding ECM and influence cell behavior.

The practice of the present invention will employ, unless otherwise indicated, conventional methods of immunology, histology, microbiology, cell and tissue culture, and molecular biology within the ordinary skill of the art. Such techniques are explained fully in the literature. All publications, patents, and patent applications cited herein are incorporated by reference in their entirety.

The design of the in vitro artificial immune system (AIS) of the present invention comprises:
1. three basic, functional, immunological tissues:
   a. skin and/or mucosal equivalent (the vaccination site),
   b. a lymphoid tissue equivalent (LTE (the lymph node), and
   c. lymphatic and blood vascular network equivalents to connect the other two tissues,
2. a cell source for reproducible and repeatable testing, and
3. a bioreactor to house and integrate the immunological tissues and rapidly assess and test vaccine efficacy.

The AIS of the present invention further comprises:
(a) an in vitro skin and/or mucosal-equivalent scaffold (vaccination site, VS) that facilitates trafficking of blood monocytes and non-monocytic dendritic cell (DC) precursors and supports their natural conversion into mature antigen presenting dendritic cells within the artificial skin 3D tissue-engineered construct;
(b) a lymphatic vessel-like pathway from the vaccination site to the lymphoid tissue equivalent (LTE) for mature DC migration and a blood vessel-like pathway for monocyte migration into the vaccination site (VS);
(c) a lymphoid tissue equivalent in a tissue-engineered scaffold with a structure that mimics lymph node geometry and contains appropriate lymph node cell types;
(d) the above constructs that are functionally equivalent tissue constructs that exhibit comparable properties to endogenous tissues;
(e) integration of these immunological tissue constructs in a modular bioreactor system.

Design and construction of a 3D perfusion mesh, membrane, or gel-like structure for the in vitro vaccination site (VS) is an important feature of the present invention. The VS provides an important part of the model of vaccine action. As a stand-alone system for vaccine studies, it enables the dissection of differences in mechanism between different vaccines, adjuvants, drugs, biologics, cosmetics, and immunotherapy candidates and thus helps in the refinement and improvement of these substances.

The design and construction of a blood endothelium pathway for monocyte migration to the in vitro VS is also important. A lymphatic endothelium pathway from the in vitro VS to the LTE for mature DC migration is provided. A 3D model consisting of vascular and lymphatic endothelial cells that supports transendothelial trafficking of monocytes and other DC precursors in a manner that recapitulates in vivo differentiation and migratory functions for a vaccination site (e.g., skin equivalent) can be used for testing cosmetics, anti-oxidants, possible skin irritants, and other chemicals.

The AIS enables quantitative measurement of T and B cell stimulation:
(a) through a venue in the LTE for DC, CD4+ T, CD8+ T and B cells to meet in one place, to test whether a vaccine or immunotherapy promotes optimal levels of T cell help (TH1 or TH2) to induce cytotoxic T lymphocyte (CTL) and B cell responses;
(b) enabling DC, T and B cells to meet in a 3D environment with extracellular matrix and support cells that mimic the environment of the lymph node where the three cell types can interact;
(c) the inclusion of endothelium so that monocytes and DCs can interact with endothelial cells during recruitment and emigration;
(d) the presence of a more representative population of cells and of cells that can migrate across the endothelium and differentiate in response to local tissue signals (for example, to distinguish the effects of TLR 9 (Toll-like receptor 9) ligands versus TLR-4 ligands, as they are expressed differentially on multiple DC subtypes).

The present invention further comprises:
1. the use of novel biomolecule controlled-release strategies (such as controlled-release microspheres, direct injection nanosyringes, dual functionality nanogels, directed degradation rates);
2. the use of directed cell migration from ETCs to and from the vascular highway using, for example, chemotaxis or the influence of shear forces on transendothelial migration (to orchestrate the cellular migratory routes to the VS (monocytes), from the VS (mature DCs), and into the LTE (mature DCs, T and B cells);
3. directed cell migration from ETCs to and from the vascular highway using magnetic microbead approaches (magnetic microbeads and electromagnetic fields may also be used to move cells between compartments of the AIS);
4. the design and construction of a lymph node-like structure (the LTE) in a 3D scaffold with a structure that mimics lymph node geometry and contains appropriate lymph node cell types, cytokines and chemokines;
5. facilitation of an approach to create tunable microenvironments to study initiation of the immune response via a model of the lymph node's T zone in the LTE design (including engrafting T zone fibroblastic reticular cells (FRCs, stromal cells of the T zone) on ordered, macroporous, hydrogel scaffolds akin to inverse opal structures and the use of both synthetic and natural extracellular matrix (ECM) materials, to achieve 3D structures that provide a physical structure mimicking the lymph node's "open" reticular network, containing lymphocytes and biochemical cues (such adhesion motifs and chemokine gradients) expected by lymphocytes in secondary lymphoid tissues);
6. in the LTE, providing the lymph node-like function of T cell help for B cell antibody production (for example, distinct T and B cell areas within the LTE can be designed by the combined action of digital printing (directing assembly of T and B cells within distinct zones) and by controlled release technology (using, for example, microspheres releasing T and B cell attractants to maintain T and B cell areas, respectively);
7. to assist in self organization of the LTE, BLC (B lymphocyte chemoattractant, MV10 kDa), MIP-3β (macrophage inflammatory protein-3β, CCL19), and SLC (secondary lymphoid tissue chemokine) chemokine microspheres for controlled release with the LTE matrix; additionally, microspheres may be co-printed with T and B cells into LTE scaffolds (in an alternative embodiment, microspheres can be directly encapsulate within the "struts" (e.g., using polycaprolactone) of the hydrogel matrix during polymerization in a criss-cross pattern, much like a "Lincoln log") (in still another embodiment, FRC-engrafted T cell areas can be used, assuming the stromal cells guide T cell localization within scaffolds);
8. the use of a digital printing BioAssembly Tool (BAT) capable of precision-manufacturing 3D ETCs, specifically with fine volumetric control to create 3D constructs;
9. use of an engineered, cellular microfluidic, environmental bioreactor that can sustain multiple immunological ETCs and be used to mimic the human immune system;
10. use of a miniature 3D housing with internal channels through which a nutrient-rich liquid is pumped to "feed" the immunological cells. The walls of these channels are modified to allow endothelial cell attachment, creating an artificial endothelium, or are fabricated from a biologically compatible material that does not alter cell behavior. Cells within the constructs rely on constant fluid flow, not just for nutrients, but also as a signal that all is well and that they should continue with their business via chemokines. Nutrient fluid primes the system before various cells are injected (via syringe initially); the complete AIS is then functionally connected to a pumping that simulates blood flow for the nutrient/oxygen solution. In a preferred embodiment, a pulsed pumping mechanism is used to better mimic the situation seen in the blood vasculature. Embodiments of miniature size and transparent architecture enable the visualization of the tissue construct components in situ under a microscope;
11. use of the AIS to test the efficacy of vaccine adjuvants, vaccine formulations, and immunotherapies in vitro for high throughput vaccine and immunomodulator screening in an ex vivo immune system with an appropriate repertoire of T and B cells;
12. the manufacture of monoclonal antibodies in the AIS by activating B cells in the LTE.

In another embodiment of the LTE, adjacent T and B cell zones are created, thereby mimicking the natural separation of B and T zones in a real lymph node. In this embodiment, T and B zones of the LTE are created using microcarriers. Much is now known about the cultivation of cells on microcarriers; these are particles typically about 100 to 5000 μm in diameter, rough surfaced or porous, coated with the necessary components of the extracellular matrix, on which a variety of anchoring dependent cells can grow and proliferate. The model system is akin to particles in a box. Matrix materials for the microcarriers may include lymphoid tissue particulate ECM material, protasan, collagen, protasan/collagen mixes, PLGA (poly(lactide-co-glycolide)), and other scaffold materials.

Figure 1A:
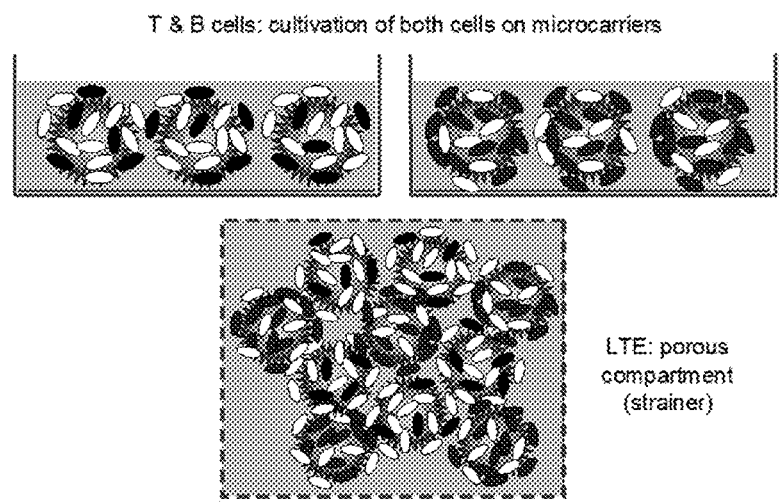
FIG. 1(A) is a schematic representation of the LTE in which T and B cell are cultivated together on microcarriers and then transferred to a porous container
Figure 1B:
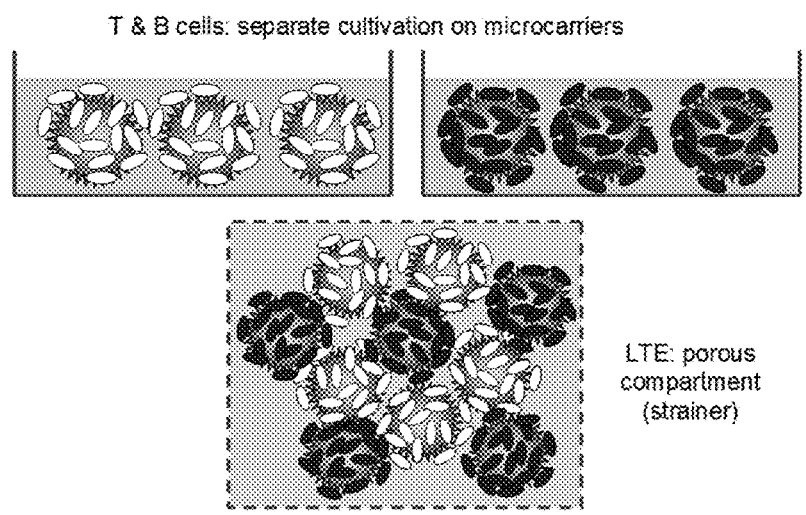
FIG. 1(B) is a schematic representation of the LTE in which T and B cell are cultivated on separate microcarriers and then brought together in a porous container.
Figure 1C:
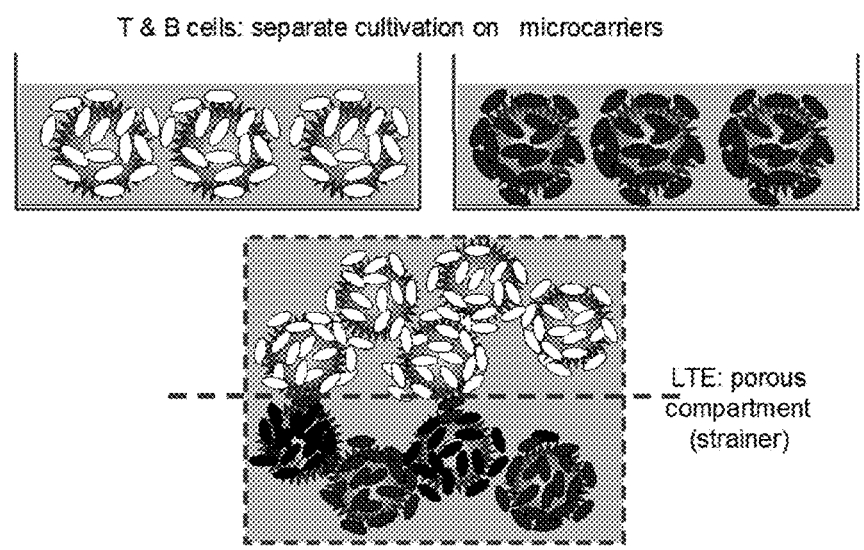
FIG. 1(C) is a schematic representation of the LTE in which separate T and B cell microcarriers are cultivated on separate microcarriers and then brought together in a porous container with separate compartments.

The general approach to creating such a LTE comprises:
1. loading microcarriers with appropriate adhesion ligands, such as chemokines, for the attachment of T and B cells; the microcarriers can be natural or synthetic, dense or porous and of various sizes depending on the desired packing density;
2. culturing s T and B cells on the microcarriers; the T and B cells can be cultivated together (FIG. 1A), or cultivated separately on their respective microcarriers (FIGS. 1B and 1C);

3. bringing together the T and B cell-populated microcarriers in contact in a porous container (akin to a "tennis ball basket;"); and
4. allowing the microcarriers to pack 'intelligently;' such packing density allows cell penetration.

Figure 1D:
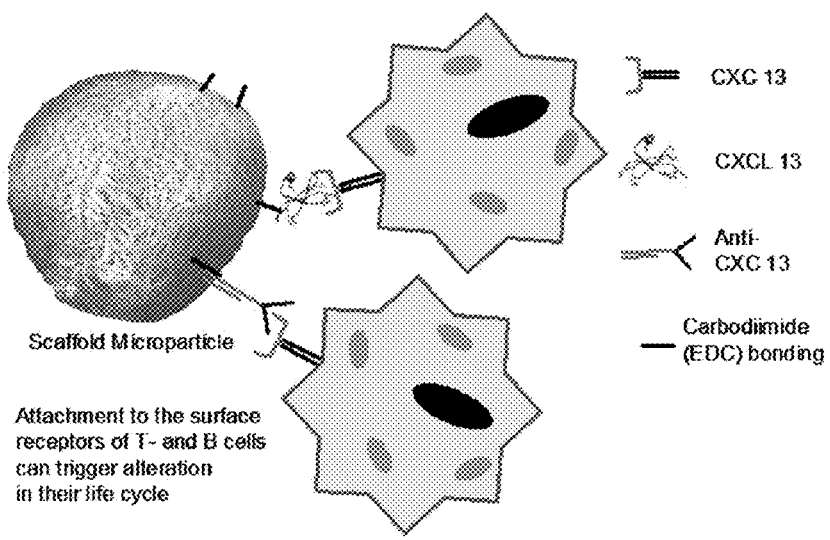
FIG. 1(D) is a schematic showing binding T and B cells to the microcarriers having CXC 13 ligand as an adhesion ligand.
Figure 1E:
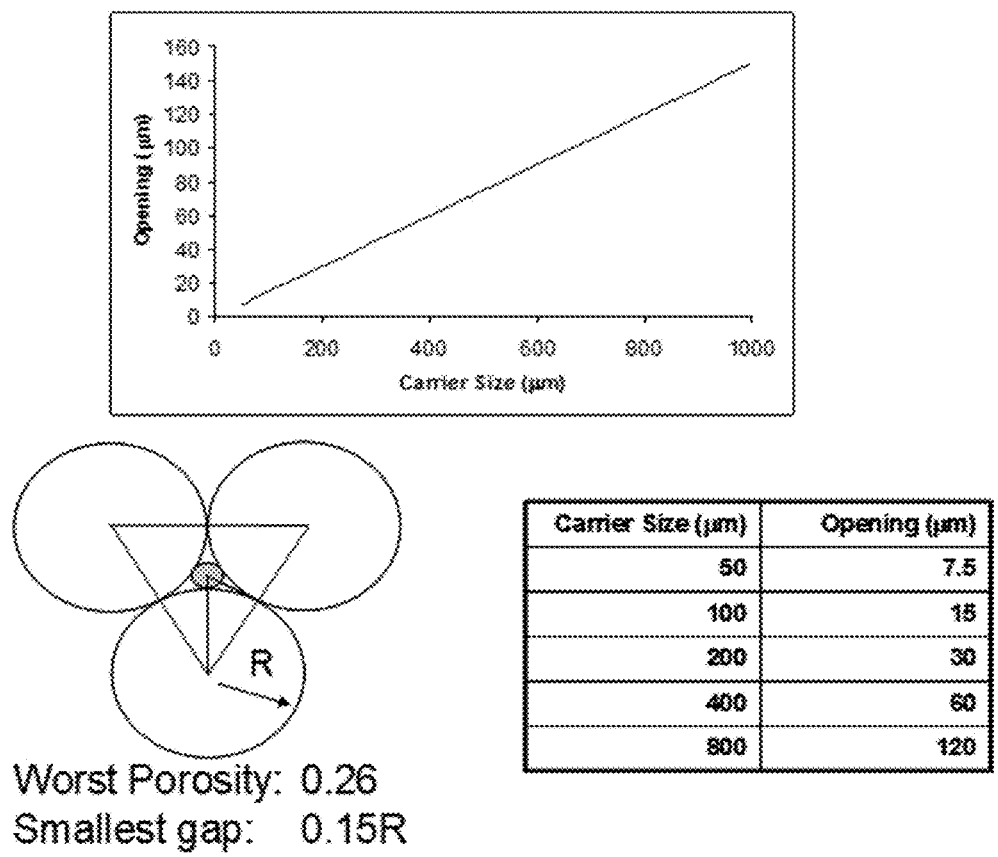
FIG. 1(E) illustrates the influence of microcarrier particle size on the porosity and openings between the microcarriers.

FIG. 1D is a schematic showing binding T and B cells to the microcarriers having CXC 13 ligand as an adhesion ligand. As shown in FIG. 1E, the size of the microcarrier particle influences the porosity and the openings between the microcarriers. In addition, the shape of the microcarriers (e.g., spherical, irregular shaped, etc.) also impacts on the optimized packing densities.

It is also envisaged that the T cells could be "free" in media while the B cells are primarily located on microcarriers or alternatively that the B cells could be "free" in the media while the T cells are primarily located on the microcarriers as other variations on this theme.

The development of an in vitro immune system requires:
1. engineering of 3D scaffolds and cell differentiation cascades that allow the formation of three basic, functional, biological tissues, in particular, immunological tissues such as:
   a. skin and/or mucosa (vaccination site, VS),
   b. lymph node (lymphoid tissue equivalent, LTE), and
   c. lymphatic and blood vascular network equivalents,
2. a cell source for reproducible and repeatable testing, and
3. a microfluidic bioreactor to house and integrate the immunological tissues.

Figure 2:
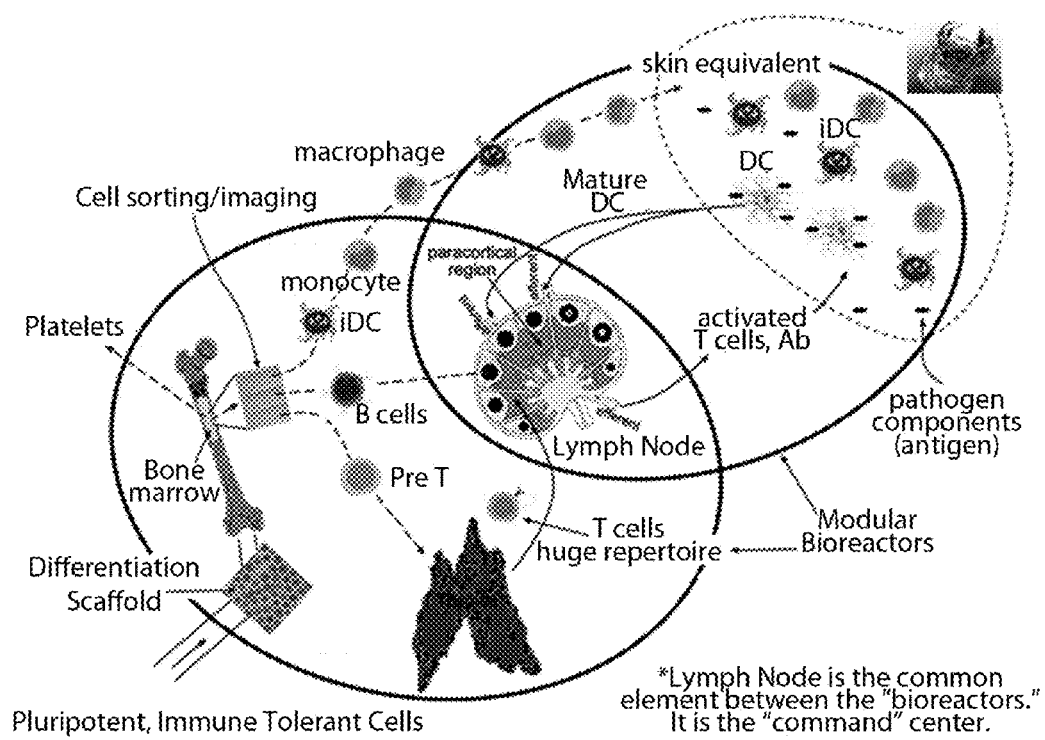
FIG. 2 illustrates how the AIS of the present invention operates.

How such a system works is illustrated schematically in FIG. 2.

There are sequential steps in the generation of an immune response to a vaccine in a mammal. First, a vaccine acts on immune cells in the skin, gut, or mucosal site of vaccination to activate cells. Second, after immunization with a vaccine, dendritic cells (DCs) migrate out of the site to the draining lymph node via lymphatic highways. Third, dendritic cells in the draining lymph node (or other secondary lymphoid tissues) interact with T and B cells to activate antigen specific lymphocytes that are capable of activating further immune responses, eliminating the pathogen through multiple effector mechanisms and transforming into memory cells with long term memory of antigen.

This three-step process is mimicked functionally and structurally in the AIS of the present invention. First, the antigen/pathogen acts on immune cells in the in vitro vaccination site (VS, e.g., skin equivalent or mucosal tissue equivalent) to activate antigen presenting cells and start the maturation process. Second, as cytokines, chemokines, and chemicals are produced at the site of vaccination, dendritic cells migrate out of the site to the lymphoid tissue equivalent (LTE) via lymphatic vessels and complete their maturation process. Third, dendritic cells in the LTE interact with T and B cells to activate antigen-specific lymphocytes that are capable of activating further immune responses, eliminating the pathogen through multiple effector mechanisms and transforming into memory cells with long-term memory of antigen.

The AIS comprises three immunological tissue constructs corresponding to the three basic steps in vaccine or immunotherapy action. To functionally reproduce these three steps, the AIS comprises three tissue engineered constructs:
1. an in vitro VS scaffold that facilitates trafficking of blood monocytes and non-monocytic dendritic cell precursors and supports their natural conversion into mature antigen-presenting dendritic cells within the artificial skin 3D construct,
2. a lymphatic vessel-like pathway from the vaccination site (skin equivalent) to the lymphoid tissue equivalent for dendritic cell migration; likewise, a blood vessel-like pathway for monocyte migration to the vaccination site (skin equivalent and/or mucosal equivalent), and
3. a lymphoid tissue equivalent (LTE) in a scaffold with a structure that mimics lymph node geometry and contains appropriate lymph node cell types.

These functionally equivalent tissue constructs exhibit comparable properties to endogenous tissues. These functionally equivalent tissue constructs are integrated in a modular bioreactor. The AIS is designed to perform high throughput vaccine and immunomodulator screening in an ex vivo immune system that provides the appropriate repertoire of T and B cells within a bioreactor system.

The Vaccination Site (VS)

Figure 3:
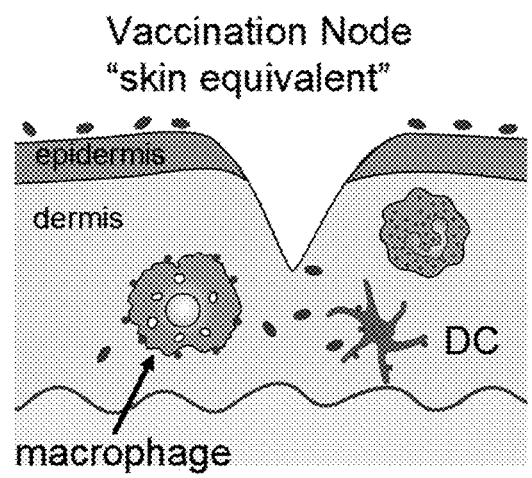
FIG. 3 is a schematic representation of vaccination site (VS).

The efficacy of a vaccine reflects, to a large degree, the quality of the initial interactions with cells at the site of vaccination (FIG. 3). Consequently, to create a useful model of vaccination, it is important to construct an artificial vaccination site in vitro. Such a vaccination site will act as a skin-, gut-, or mucosal-equivalent tissue and comprises a skin construct (or a mucosal tissue, such as lung), together with vascular and lymphatic endothelium and blood-derived hematopoietic cells. The skin construct can be derived from many sources, including complex sources, such as cadaveric human skin, less complex sources, such as commercially available skin-like products (EpiDerm, Episkin), or simple skin-like structures (using many different preparations of ECM and sources of skin fibroblasts and keratinocytes) optimized for integration into the in vitro system.

Blood cells (including monocytes) can be placed (or can flow) along the vascular endothelium. Such cells naturally migrate, convert to dendritic and other cells, and become resident in the skin.

If dendritic cells are present in the correct subtype and state of maturation for resting skin, the vaccination site is then ready to accept a vaccine candidate for testing. Upon vaccination, the vaccine will interact with skin-resident cells to induce further migration of monocytes and other cells into the skin, and their subsequent differentiation into more antigen-presenting cells (APCs), including macrophages and dendritic cells. Dendritic cells (DCs) and other antigen-presenting cells (APCs) pick up vaccine antigen and will be induced to migrate across the lymphatic endothelium to drain in the lymphoid tissue equivalent. DCs arriving in the LTE interact with T and B cells to initiate an adaptive immune response, and depending on the maturation state of the DCs, they will activate T and B cells to differing extents.

In summary, together with the LTE (described below), the vaccination site provides an important model of vaccine, chemical, adjuvant, drug, or biologic action. However, even without the LTE, the vaccination site is an important stand-alone model for vaccine studies that enables the dissection of differences in mechanism between different vaccines or chemical candidates and thus helps in the refinement and improvement of vaccines. It is an important stand-alone model for testing cosmetics, fragrances, antioxidants, possible skin irritants, and other chemicals.

The In Vitro Lymphoid Tissue Equivalent (LTE)

Figure 4:
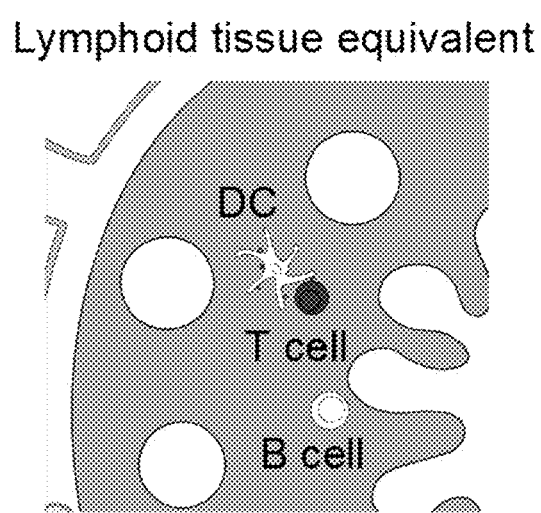
FIG. 4 is a schematic representation of an artificial lymphoid tissue (or lymphoid tissue equivalent).

The ultimate output of a vaccine occurs in the lymphoid tissues, where antigen-specific T and B cells are activated and partly convert to memory cells that have been notoriously difficult to detect in vitro. To mimic a natural immune response in vitro, it is therefore essential to build a lymphoid tissue equivalent (FIG. 4) and connect it up with the vaccination site via lymphatic vessels. In vivo, vaccine-derived antigen is transported to lymph nodes by diffusion along lymphatic vessels to lymph node cells, or by migration of mature DCs that have internalized the antigen, to the draining lymph node. In the lymph nodes, DCs activate antigen-specific T cells and, in conjunction with helper T cells, help to activate antigen-specific B cells to elicit an immune response.

The strength and quality of the T and B cell responses depend on the amount of antigen delivered and on the subtype and maturation state of the DC (APC) carrying the vaccine-derived antigen. Two- and three-way interactions between the key cells (dendritic cells, B and T cells) occur in spatially segregated regions of the lymph nodes in a sequential order of events. To simulate this process, an artificial lymphoid tissue or lymphoid tissue equivalent (FIG. 4) can be constructed with lymph node-like geometries and spatial organization in vitro using a combination of tissue engineering, materials science, and biological studies. For example, immune cells are highly responsive to chemokine gradients, and thus the design of scaffolds containing organized gradients of these signaling molecules allows the synthetic lymph node tissue to self-organize, in a fashion similar to that in native tissue. The formation of native tissue can also be studied in parallel to uncover further molecules to help form in vitro-organized tissues. Such complex synthetic structures can also be fabricated using the digital printing BioAssembly Tool (BAT).

In an embodiment of the present invention, once the LTE is assembled, it is also possible to use it as a "biofactory," biosynthesizing various desired biomolecules (such as cytokines, proteins, antibodies). For example, if an antigen is presented to B cells, they can create antibodies in the LTE. Potentially, the created antibodies could also be monoclonal, depending on the repertoire of B cells and how the peptide is presented to the B cells.

In Vitro Lymphatic and Blood Vascular Highways

Figure 5:
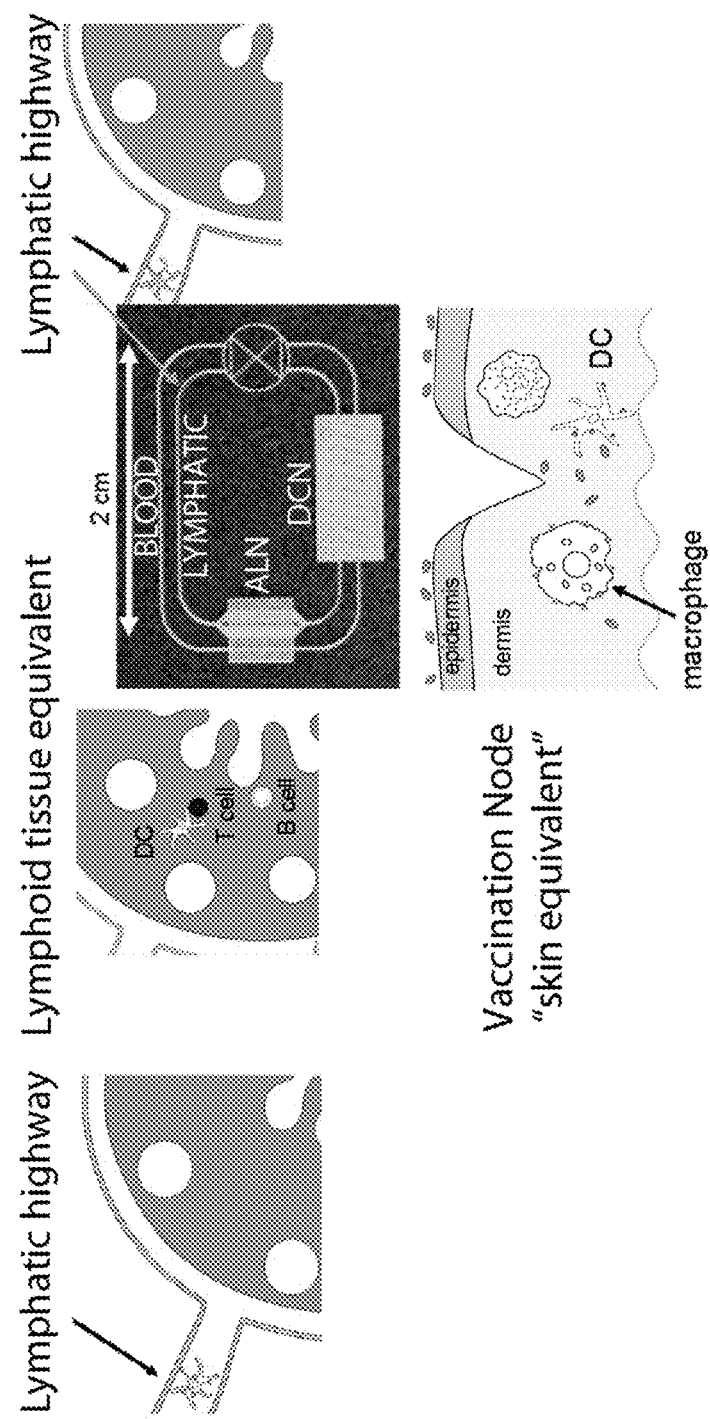
FIG. 5 is a schematic of the in vitro immune system ensemble.

The present invention provides designs for endothelium pathways (e.g., using different matrix formulations, sources of endothelial cells, and growth conditions) that facilitate cell immigration and emigration into and from the VS and the LTE, as well as between the VS and LTE. A schematic of the in vitro artificial immune system ensemble is shown in FIG. 5. The artificial immune system can have a general bioreactor design that is mechanistically different than the natural immune system, though similar in terms of functionality. In a preferred embodiment, the three immunological ETCs are integrated in a miniature, engineered, cellular environmental bioreactor. This design uses two functionally equivalent membranes in a sequential order to create a functional VS and localized collections of T and B cells on or around particles, to function as the LTE Important design considerations are to emulate biological functions, minimize media volume between zones to increase efficiency of cell trafficking, and provide a means of evaluating antigenic responses. By integrating and minimizing the media volume, potential for cell migration within and between the immunological ETCs is dramatically enhanced and can provide an increased immunological response.

However, it is not necessary to have the VS and LTE in an integrated bioreactor. In an alternative embodiment, mature DCs from the VS can be physically positioned in the LTE. These mature DCs will activate T cells within the T cell zones and B cells within the B cell zones of the LTE. Thus, it will be possible to test and characterize both the VS and LTE and the interactions between the mature DCs from the VS and the T cells in the LTE in a non-integrated fashion.

The general, basic cascade of events for AIS operation is as follows:
monocytes and other blood derived cells (PBMCs) are injected into the blood vascular highway;
chemokines (either natural to the VS or intentionally added) attract monocytes to enter into the VS;
monocytes differentiate into immature DCs (iDCs);
iDCs mature in response to vaccination in the VS;
chemokines attract mature DCs into the lymphatic highway;
chemokines (either natural to the LTE or intentionally added) attract mature DCs into the LTE; and
mature DCs in the LTE activate T and B cells.

Monocytes and dendritic cells will naturally interact and migrate across the vascular and lymphatic endothelia. In other embodiments chemokines can be used to direct the migration of the cells, as can magnetic microbeads. Magnetic beads together with miniaturized electromagnets are a convenient mechanism for manipulation of cells in a bioreactor. For example, cells with appropriate surface markers (receptors, epitopes) can be selected using the beads and selected cells can be transported from one local environment to another, bringing cells in contact with, e.g., desired surfaces, environments, or other cells (see Examples).

Universal Cell Source

The in vitro AIS device would at a minimum have to contain T cells, B cells, and antigen-presenting cells, but would preferably include other cellular components, such as endothelial cells to create the endothelium, neutrophils and mast cells to respond to vaccine-derived signals, fibroblasts cells that mediate initial entry of a specific pathogen into the skin, or cells from target organs (e.g., lung) that the pathogen in question infects. The T and B cells would be located primarily in the LTE, the monocytes/DC precursors in the blood vasculature and the vaccination site, and the blood and lymphatic endothelial cells would be in the blood and lymphatic highways, respectively.

In an embodiment, the immune cells from peripheral blood mononuclear cells (PBMC) will be from individuals who are HLA (human leukocyte antigen)-matched to the endothelium and VS matrix cells used in the system. Peripheral blood mononuclear cells represent a heterogeneous population of immune cells (T cells, B cells and various granulocytes) that arise from pluripotent hematopoietic stem cells in the bone marrow (Janeway, et al., *Immuno. Biology* (1999), Garland Publishing/Elsevier London, UK). In an alternative embodiment, using stem cells, it may be possible to provide all the necessary cell types for the system. In still another embodiment, parallel with progenitor cell development, cells from a humanized mouse node can be used to initially populate the various tissue constructs.

The Bioreactor

In the integrated AIS bioreactor, a nutrient-rich liquid is pumped through internal channels in a 3D housing to 'feed' the immunological cells. The walls of these channels are modified to allow endothelial cell attachment, creating an endothelium, or are fabricated from a biologically compatible material that does not alter cell behavior.

To overcome obstacles in developing the AIS bioreactor, in one embodiment, laser micromachining with ultra-short pulse lasers can be used to design and fabricate the channels so that the fluid flows well. In other embodiments, microstamping, laminates, or standard CNC and other milling processes can be used.

Cells within the constructs will rely on a constant flow, not just for nutrients, but also as a signal that all is well and that they should continue with their business via chemokines. Nutrient fluid will prime the system before various cells are injected via syringe initially or using the cell sorting systems described.

The complete artificial immune system is then connected to a pump that simulates blood flow for the nutrient/oxygen solution. In a preferred embodiment, the pumping mechanism can also be pulsed, to better mimic the blood vasculature. The entire assembly can then be inserted into an incubator that regulates temperature, humidity, and concentrations of oxygen and carbon dioxide to best simulate the natural in vivo environment.

In a preferred embodiment, the bioreactor system can be constructed to be of the order of a few inches in total size, potentially allowing the in vitro immune system bioreactor apparatus to be built into other stationary and portable analytical instruments. Embodiments of miniature size and optical transparency allow viewing of the tissue construct components in situ using a microscope.

Using the AIS, it is possible to rapidly test and evaluate the immune response to vaccines and other substances. Several concepts are presented to organize the tissue and activate it appropriately to receive vaccines. In one embodiment, the integrated engineered tissue constructs incorporate chemotaxis and engineered-release microparticles to allow control of temporal, spatial, and dose parameters of various biomolecules for tissue and cell assemblage and programming. In another embodiment, constructs provide an environment that enables the stroma and parenchyma to self-assemble into a native-like tissue via communication achieved through cell-cell, cell-matrix, structural and endogenous growth factor cues that the cells themselves create; no exogenous growth factors may be necessary to induce given phenotypes.

EXAMPLES

Example 1

Figure 6:
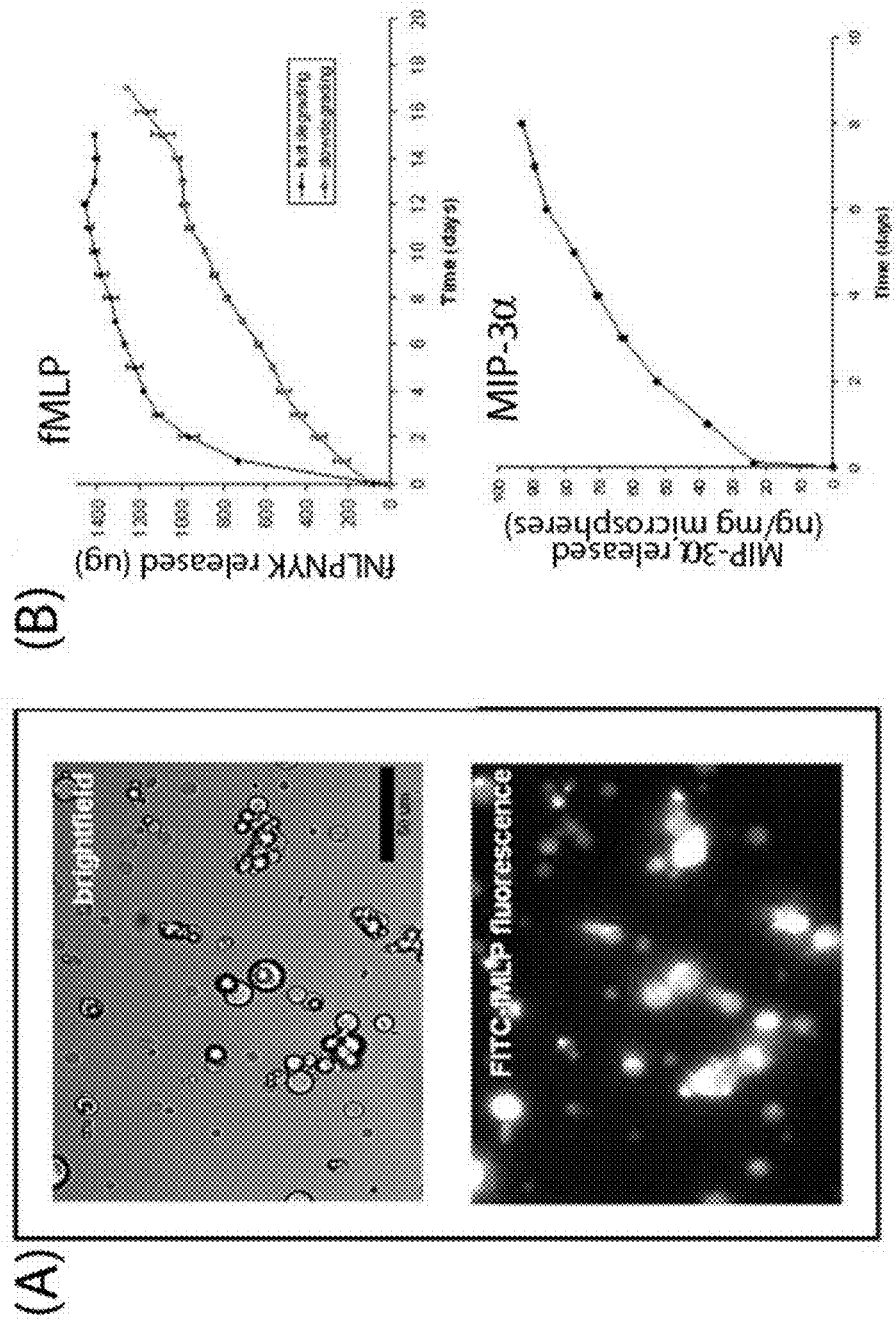
FIG. 6A is example micrographs of microspheres encapsulating fluorochrome-labeled fMLP chemokine (a monocyte and immature DC chemoattractant).
FIG. 6B is a diagram showing in vitro release kinetics for a peptide chemokine (fMLP) and a 10 kDa chemokine (MIP-$3\alpha$).
Figure 8:
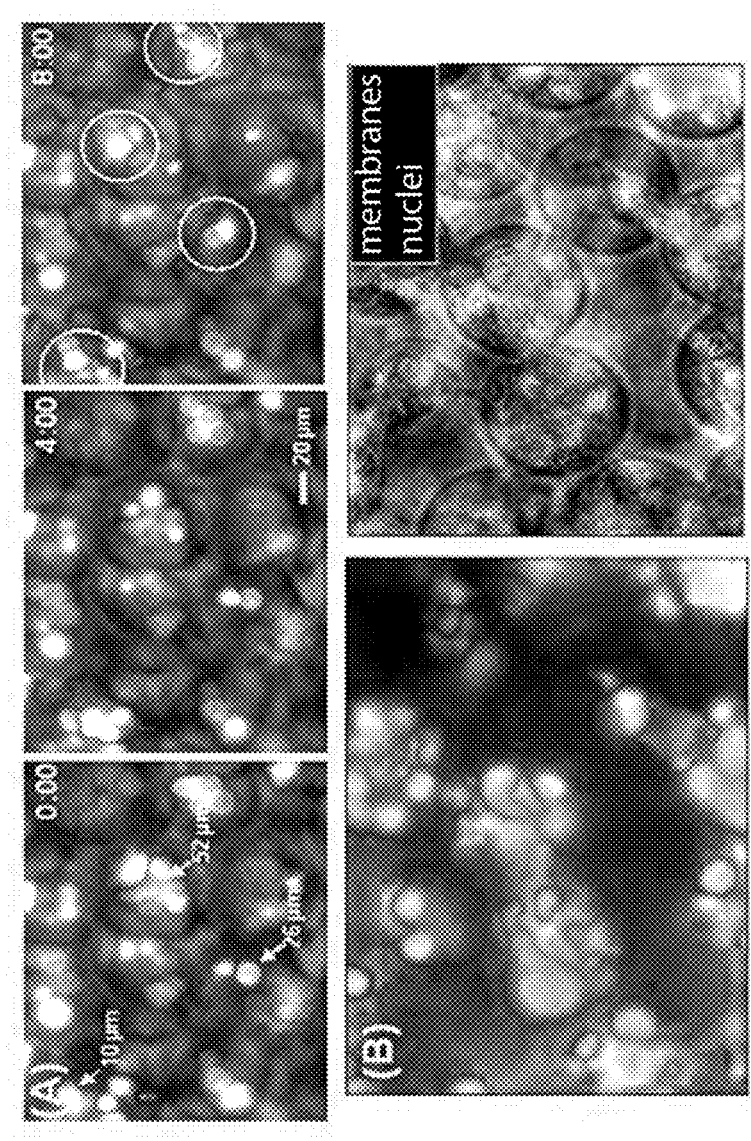
FIGS. 8A and 8B are pictures showing cell development in a lymphoid tissue equivalent (LTE) matrix. Synthetic inverse opal hydrogel scaffolds were synthesized that support T-cell migration and interaction with B cells (FIG. 8A), and the attachment and growth of high cell densities, which is an important feature in mimicking the microenvironment of the lymph node (FIG. 8B).

In Vitro and In Vivo Control of Chemotaxis of Both iDCs and Monocytes Using Controlled-Release Microparticles PLGA (poly(lactide-co-glycolide)) microspheres provide steady controlled release of encapsulated chemokines. FIG. 6A shows example micrographs of microspheres encapsulating fluorochrome-labeled fMLP chemokine (a monocyte and immature DC chemoattractant). FIG. 6B shows the release kinetics for both low molecular weight peptide chemokines and a 10 kDa chemoattractant, MIP-3β (macrophage inflammatory protein-3β). As shown in FIGS. 7A-7D, human monocytes and dendritic cells move towards microspheres releasing the chemoattractant fMLP (N-formyl-methionyl-leucyl-phenylalanine) in an in vitro setting. FIG. 8 shows in vivo mouse immunohistochemical staining for monocytes that were attracted to the chemokine MIP-3β in an implanted extracellular matrix scaffold. Synthetic inverse opal hydrogel scaffolds were synthesized that support T-cell migration and interaction with B cells (FIG. 8A), and support attachment and growth of high cell densities, which is an important feature in mimicking the microenvironment of the lymph node (FIG. 8B).

Example 2

Designer Scaffold Structures

Designer scaffold structures were constructed to test cell viability, cell motility, and nutrient flow for bioreactors and have studied cell motility as a function of construct stability for collagen gels. FIG. 64 shows HUVEC cells growing on protasan/collagen matrix on a nylon mesh. High magnification SEM of the nylon membrane and interspersed Protasan/collagen matrix material is shown in the top image. Seeding of the primary layer of HUVEC cells was accomplished on an inverted membrane (left, Side 1), then 24 hours later, brought to an upright position (right, Side 2) where the second layer was applied. Phase contrast images of each plane of HUVEC cells is shown in the center two lower images, with the left being the first layer, and the right being the second layer applied.

Example 3

Digital Printing Technology

Figure 9:
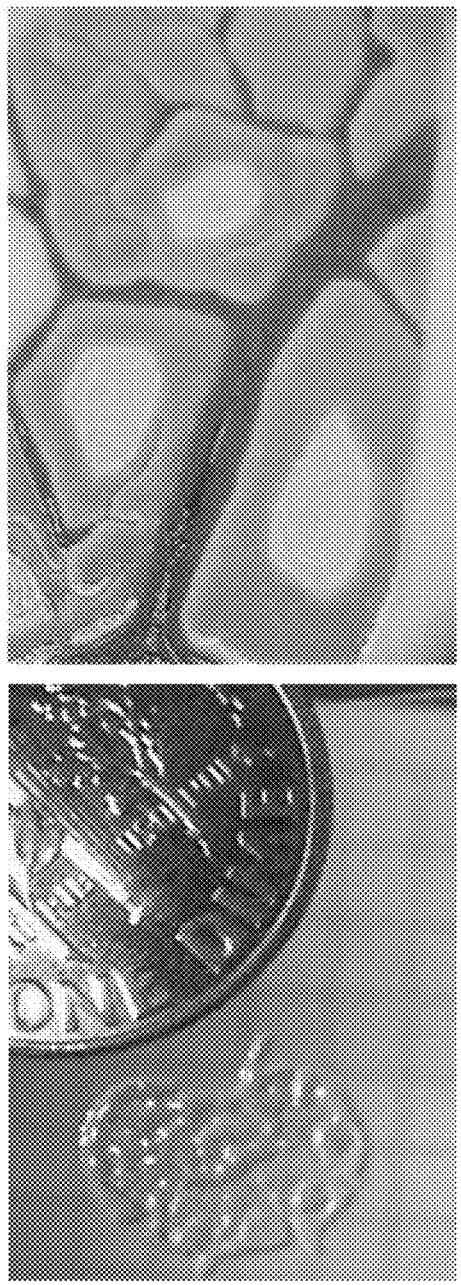
FIG. 9 shows mockup of digitally printed lymph node (left panel) and a retinal image of vasculature (right panel).

Preliminary hardware and software ETC heterogeneity digital printing prototypes have been developed. FIG. 9 shows the mockup of a digitally printed lymph node and a retinal image of vasculature. This mockup lymph node comprises six biocompatible hydrogel layers, four different patterns, and three materials. The vasculature image has been built with multiple layers of biodegradable construction material with feature sizes that range from 100 to 3,000 μm. The objects were fabricated with three dispensing nozzles each.

Example 4

3D Tissue Constructs 3D biology is important to induce proper functionality of the immunological ETCs. An important approach to studying cellular processes is to culture cells in vitro. This has typically involved plating cells on plastic or glass supports. In this application, cells grown on solid or filter support are referred to as two-dimensional (2D) cultures. Such 2D cultures on porous supports have been useful for studying many aspects of biology. However, much more in vivo-like conditions can now be realized in 3D cultures.

The majority of vaccines are delivered via the skin or mucosal surfaces of the body. Within the delivery site, key steps in the action of vaccines are the differentiation of precursor cells to dendritic cells (DCs), the acquisition of antigen by DCs, and the maturation of the DCs to optimally process antigen and activate T cells, B cells, and other immune cells. During the period of DC maturation, DCs must also be mobilized and transported to a position within the T cell zone of lymph nodes where they can optimally encounter and select the T cells with the most appropriate T cell receptor to respond to the processed antigen in question. In some cases, antigens diffuse to the draining lymph node directly, and are then captured by lymph node DCs.

To date, there has been no model of these early steps of vaccine action in humans; furthermore, it is not possible to study these steps in humans because it occurs in inaccessible peripheral tissues and not in the more accessible blood. Therefore, the present invention provides a model system that enables studies of these early steps in a more realistic context of cells and structures than is currently available.

The present invention provides a model vaccination site in vitro for testing the efficacy of vaccines in antigen loading and activation of immune cells, especially dendritic cells. The vaccination site comprises immune cells, including monocytes and dendritic cells, embedded in a skin-equivalent (or mucosal tissue equivalent) tissue that is attached to vascular and lymphatic endothelium. This in vitro tissue construct enables rapid testing of vaccine candidates and evaluation of their effects at the early steps of vaccination. The vaccination site is then integrated with the lymphoid-tissue equivalent to form an artificial immune system for testing vaccine efficacy in a more complete model of the human immune system.

The VS can be envisaged as a skin equivalent or a vaccination site equivalent to the in vitro immune system. In an alternative embodiment, a mucosal tissue equivalent can also be readily envisaged. The skin equivalent is preferred because of recent advances in skin tissue models in vitro. Indeed, a number of studies exist in the literature that have used human skin explants and still others have probed DC behavior in volunteer subjects, who consented for biopsies during immune modulation studies (Cumberbatch, et al., Br. J. Dermatol. 141:192-200, (1999)). There have been a few reports on the integration of DCs in skin in vitro cultures (Regnier et al., J. Invest. Dermatol. 109:510-512, (1997); Fransson, et al., Br. J. Dermatol. 139:598-604, (1998)). Finally and most importantly, skin is the most common site of vaccination. Consequently, it is logical to use skin models to study the early stages of DC activation in the periphery.

The present invention provides a reproducible skin equivalent model for testing vaccine candidates and other drugs, biologics, and chemicals and for integrating this tissue with a lymphoid tissue equivalent in vitro to measure T and B cell immune responses. A step-wise approach is provided to build a 3D structure that comprises vascular and lymphatic endothelial cells that can support transendothelial trafficking of monocytes and other DC precursors in a manner that recapitulates in vivo differentiation, maturation and migratory functions.

Figure 10:
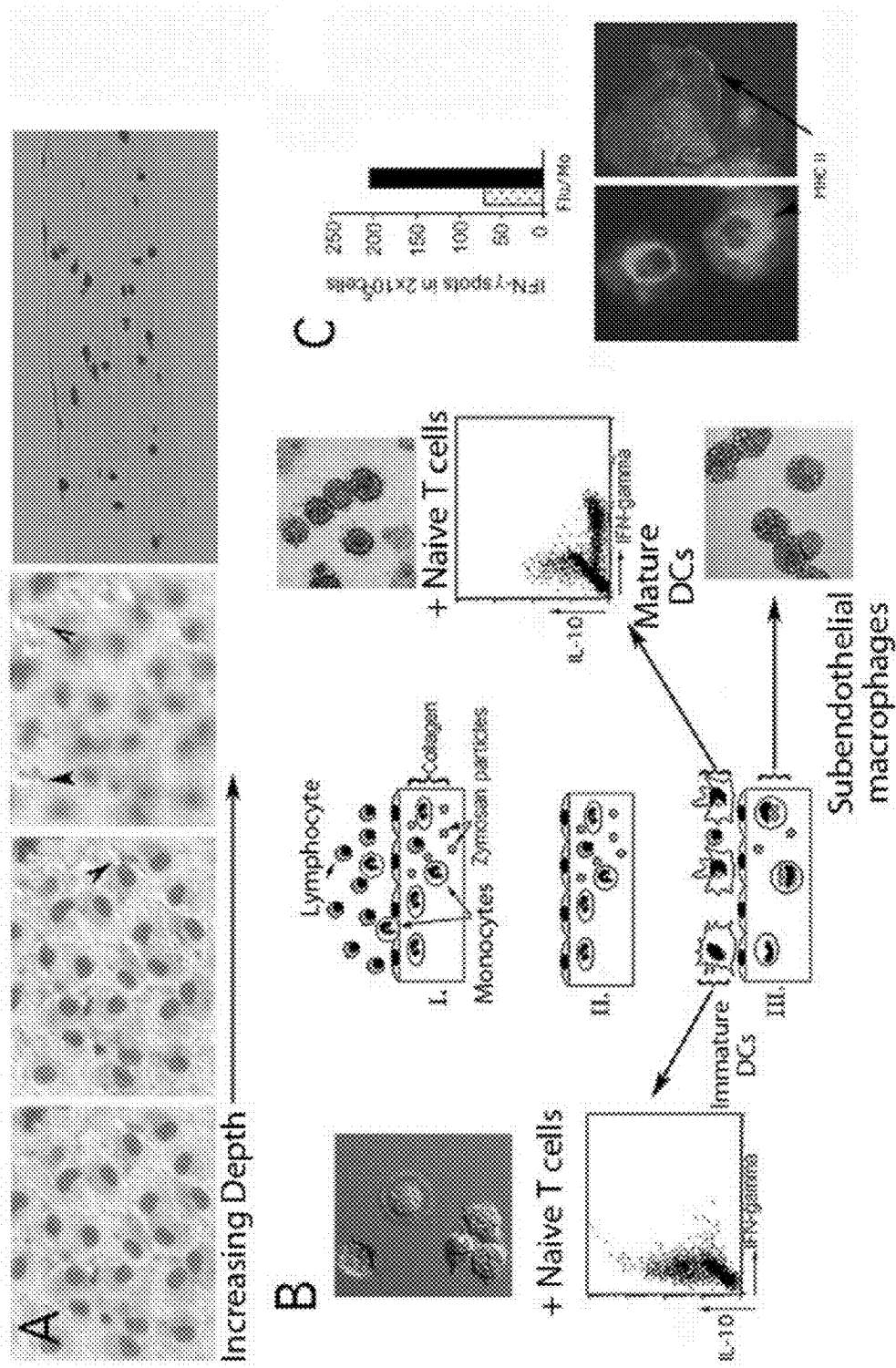
FIGS. 10A-10C show antigen-presenting cell behavior in an artificial immune system.

It is known that a 3D tissue construct that permits heterologous cell-cell interactions impacts the differentiation of DC precursors, including monocytes, in a manner that more closely mimics an intact human system than is observed in 2D culture (See, e.g., Edelman & Keefer, Exp. Neurol. 192:1-6 (2005)). Specifically, co-culture of whole PBMCs with vascular endothelial monolayers, grown on either reconstituted type I collagen matrices (Randolph, et al., Blood 92: 4167-4177 (1998a); Randolph, et al., Science 282:480-483 (1998b); Randolph, et al., Proc. Natl. Acad. Sci. USA 95:6924-6929 (1998c); Randolph, et al., J. Exp. Med. 196: 517-527 (2002)) (FIG. 10) or native amniotic connective tissue (Randolph & Furie, J. Exp. Med. 183:451-462 (1996)) promotes the passage particularly of monocytes across the endothelium, largely in response to endogenous production of the chemoattractant monocyte chemoattractant protein (MCP)-1 (CCL2) (Randolph & Furie, J. Immunol. 155:3610-3618 (1995)). This is consistent with the knowledge that many monocytes leave the blood each day, under normal steady state conditions. When the endothelium is activated, other inflammatory cell types, such as neutrophils, can traverse the endothelium, again with the same regulatory events that are understood to operate in vivo (Furie & McHugh, J. Immunol. 143:3309-3317 (1989)). If the fate of monocytes is followed with time in endothelial cell/collagen cultures, it becomes apparent that a substantial fraction of monocytes increase production of a range of molecules (including MHC II, CD40, CD83, CD86) known to be upregulated in DCs and these cells also acquire migratory properties such that they migrate out of the cultures, crossing the endothelium in the abluminal to luminal direction, away from the vascular endothelium and away from the macrophages that remain resident in the subendothelial matrix.

As shown in FIG. 10A, vascular endothelial cells grown on 3D constructs of fibronectin-coated collagen form intercellular junctions that remain intact after passage of monocytes into subendothelial matrix to increasing depths (arrowheads, monocytes visualized by differential interference contrast microscopy). En face views and a cross-section of the cultures are shown, where emigrated leukocytes are distributed throughout the matrix under the characteristically flat endothelial monolayer. As described in design features 1 and 2, a lymphatic endothelial monolayer or an epidermal monolayer, respectively, on the currently bare lower surface of such a matrix. FIG. 10B is a schematic diagram showing the stages of monocyte behavior in such a 3D culture. The image on the left depicts the sequence of observations when the matrix does not contain a source of microbial antigen, whereas the images on the right depict the sequence of observations made when yeast particles (zymosan) are incorporated as a model microbial antigen in the matrix. In stage I, incubation of peripheral blood mononuclear cells (PBMCs) are incubated with endothelium for 1.5 hours results in the transmigration of most monocytes (3), some BDCA1+ blood dendritic cells (data not shown), natural killer cells (Berman et al., J. Immunol. 156:1515-1524, (1996)), but few lymphocytes, into the subendothelial collagen. Of the few lymphocytes that do migrate, these are likely of a memory phenotype (Gergel & Furie, Infect. Immun. 69:2190-2197, (2001)), consistent with our understanding that naive T cells traffic into lymph nodes directly and memory T cells can enter tissues. In stage II, the cell culture is washed, and monocytes accumulated in the subendothelial matrix are left with an intact endothelial monolayer, where the monocytes engulf phagocytic particles if such particles have been included in the collagen matrix. In stage III, some of the phagocytic monocyte-derived cells retraverse the same endothelium and accumulate in the apical compartment. These reverse-transmigrated monocytes previously or simultaneously differentiate into DC. Photographs (upper right, B) show their characteristic morphology. When no activation stimuli are included in the cultures (left), the reverse-transmigrated cells are immature DCs and promote T cells to produce IL-10 as observed by intracellular cytokine staining. Many of these cells are non-adherent, like DCs, but a few spreading cells are similar to less differentiated monocytes (left photo inset, B). When activation stimuli are included in the cultures, the reverse-transmigrated cells become mature DCs and promote development mainly of IFNγ producing T cells. C) Monocytes can be infected with influenza to measure activation of IFNγ induction and expansion during recall responses in T cells from adults previously infected with flu (Qu, et al., J. Immunol. 170:1010-1018, (2003)). The number of T cell clones that begin in proliferate (each represents a "spot" in ELISPOT assay) in response to presentation of the processed virus is more than 3-fold increased when monocytes are permitted to differentiate in the 3-D endothelial cultures (filled bar) compared with their response when they are cultured on bare plastic. Even in the absence of a maturation stimulus in the endothelial/collagen cultures, some monocytes accumulate MHC II in perinuclear compartments, indicative of immature DCs (Mellman, et al., Cell 106:255-258, (2001)), in contrast to the same monocytes cultured on plastic where they express a greatly reduced amount of MHC II on the cell surface, more characteristic of macrophages (C, photos).

As DCs are known to traffic substantially through lymphatic vessels, by traversing lymphatic endothelium in the abluminal to luminal direction, these data demonstrate that the in vitro model mimics aspects of DC trafficking via lymphatics. Experiments identifying molecules that mediated DC migration in this model and then evaluating whether the same mediators control DC migration in intact authentic human skin explants, support this (Randolph, et al., Science 282:480-483 (1998b); Robbiani, et al., Cell 103:757-768 (2000)). This model system has also, for example, allowed examination of the role of monocyte heterogeneity in differentiation to DCs; the CD16+ monocyte subset preferentially develops into DCs over other monocytes (Randolph, et al., J. Exp. Med. 196:517-527 (2002)). Recent in vivo studies in mouse have identified a population of monocytes apparently equivalent to CD16+ monocytes, and studies indicate that this subset readily becomes DCs (Randolph, et al., J. Exp. Med. 196:517-527 (2002)). Thus, the 3D model of the present invention mimics normal immunophysiology.

Before microbes can be engulfed and destroyed, leukocytes in the periphery must be able to reach them. The process is a complex one, and mutational data indicate that it is very important: severe immunodeficiencies result from a failure of leukocyte adhesion, diapedesis, and chemotaxis, which have not been addressed in skin equivalents thus far.

By increasing in a step wise fashion the complexity of the 3D construct, and conducting assays for verification along the way, a faithful recapitulation of the events that regulate recruitment of DC precursors and other inflammatory cells that would modulate their responses is achieved. The differentiation of these DCs in response to vaccine formulations or characterized antigens/pathogens, and their trafficking into lymphatic vessels. In one embodiment, this can be achieved using printed scaffolds and the novel matrices/methodology described herein, and additional experience in the isolation and growth of skin derived blood and particularly lymphatic endothelium (Podgrabinska, et al., Proc. Natl. Acad. Sci. USA 99:16069-16074 (2002)). Moreover, our work with human skin explants provides assays and a sound basis for comparison of outcomes between the in vitro model and the behavior of DCs in intact skin (Randolph, et al., Proc. Natl. Acad. Sci. USA 95:6924-6929 (1998c)).

In one embodiment, a 3D model comprising vascular and lymphatic endothelial cells was constructed. The vascular and lymphatic endothelial cells support transendothelial trafficking of monocytes and other DC precursors in a manner that recapitulates in vivo differentiation and migratory functions. As it is now possible to differentially isolate vascular and lymphatic endothelium (Podgrabinska, et al., Proc. Natl. Acad. Sci. USA, 99:16069-16074 (2002)) and given the knowledge and resources for preparing these cells, a functional model was designed as diagrammed in FIG. 11. Several matrices can be used, including xenographic ECM sheets, natively polymerized human amniotic connective tissue (Randolph & Furie, J. Exp. Med. 183:451-462 (1996)), reconstituted collagen matrices, protasan/collagen membrane scaffolds, or preferably matrices that contain fibroblasts and/or mast cells. Several commercial preparations of dermal tissues containing fibroblasts are available and these are readily prepared in vitro, for example by seeding fibroblasts with matrix components and allowing the fibroblasts to modify and contract these components, as described earlier.

It is anticipated that the process of incorporating cells within the matrix could be adapted for the incorporation of a variety of cells such as fibroblasts or mast cells. In a preferred embodiment, vascular and endothelial monolayers are constructed that mimic the normal physiology of these vessels in coordinating recruitment and trafficking of immune cells during immunization. In another embodiment, the endothelium can be derived from human foreskin (Podgrabinska, et al., Proc. Natl. Acad. Sci. USA, 99:16069-16074 (2002)) or from adult skin.

Using a 3D in vitro model, DC migration, an important process in the initiation of immunologic priming, has been examined (Podgrabinska, et al., Supra, (2002)) Robust translation between the in vitro constructs, ex vivo models, and in vivo studies can be made. In an initial screen of a large panel of neutralizing mAbs, it was found that mAbs that recognized ABCB1 not only blocked reverse transmigration of monocyte-derived cells in the in vitro endothelial cell/collagen constructs, but the same mAbs also effectively prevented the migration of Langerhans cells from human epidermis. Further analysis of this family of lipid transporters revealed strong expression of another member ABCC1 (ATP-binding cassette protein C1, MRP-1) in human skin DCs, and specific antagonists of ABCC1 also block skin Langerhans cell migration from explants. In mice, ABCC1 is much more strongly expressed than ABCB1. Functional studies indicated that ABCC1 participates in DC migration in vivo. Thus, the in vitro model in which human monocytes become DCs in conjunction with their passage through endothelial monolayers proved useful as a screening tool for relevant mediators of migration. In a similar experiment, an important role for chemokine receptor CCR8 in reverse transmigration in vitro and then subsequently in vivo has been revealed (Qu, et al., JEM 200:1231-1241 (2004)).

Thus, the differentiation and migration of DCs in the in vitro model of the present invention accurately reflects outcomes in vivo, even after crossing the human-mouse species barrier.

The advancements set out in the present invention over previous methodologies include, as a result of this design feature, more natural recapitulation of lymphatic trafficking. The monocyte-derived DCs are designed to be redirected to migrate across the lymphatic endothelium after first traversing the vascular endothelium. Based on studies of endothelium in 2D cultures, these features will be accurately maintained (Podgrabinska, et al., Proc. Natl. Acad. Sci. USA, 99:16069-16074 (2002)).

Example 5

Loading VS with Leucocytes

Further probing of the veracity of the VS design can be conducted using, for example, immune stimulation assays. Antigens of different compositions can be used, including stimuli delivered by various delivery depots. If the system operates as in vivo, a greater variety of leukocytes, including granulocytes will cross the vascular endothelium and enter the matrix after introduction of a pathogenic stimulus, like bacteria, compared with cultures not activated with such a stimulus. Viruses may promote a cellular infiltration of a different composition. It is expected that primarily DCs and memory T cells will traverse the full construct, crossing first vascular endothelium, penetrating the connective tissue matrix where they may acquire deposited antigen, and then trafficking across the lymphatic endothelium.

In one embodiment, the cells could be adult white blood cells and adult human skin derived vascular and endothelial cells. In such an embodiment, there would not be histocompatibility between endothelial cells and the leukocytes. In another embodiment, histocompatibility may be achieved by using all cells derived from human embryonic stem cells (ESCs). It is presently feasible to ensure that data generated in the model using cells from different donors is similar to that in a fully histocompatible system.

In another embodiment, full histocompatibility of leukocytes and endothelial cells can be achieved by working with endothelial cell derived from a particular male donor's foreskin and using cord blood from the same individual as the donor for leukocytes, including the monocytes and T cells. Foreskin tissue and cord blood can be obtained from the same donor (Podgrabinska, et al., Supra (2002)). Additionally, cord blood is a useful source of monocytes and T cells that generally recapitulates the trafficking patterns and generation of DCs observed with adult monocytes (Qu, et al., *J. Immunol.* 170:1010-1018 (2003) and the use of cord blood monocytes can lead to priming of the autologous T cell population. In another embodiment, HLA-matched foreskins and cord blood can be used to achieve histocompatibility.

Example 6

Fabrication of VS Scaffold Using Protasan

In another embodiment of the present invention, porous chitosan/collagen scaffolds are used in the vaccination site tissue-engineered construct. The membrane scaffold for the VS comprises a porous membrane comprising preferably natural biopolymers that accommodate confluent cultures of vascular and lymphatic endothelial cells, and remain sufficiently permeable to provide transmigration of monocytes during their transformation into immature dendritic cells.

Figure 12:
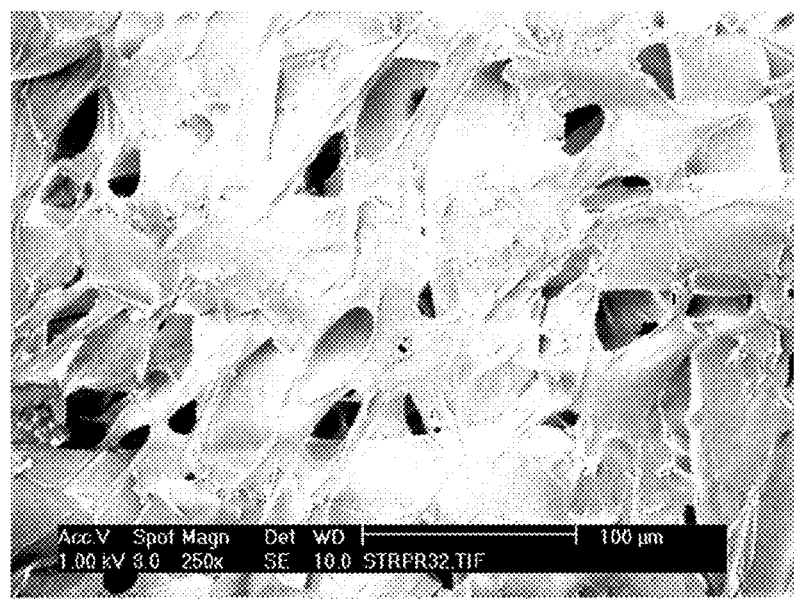
FIG. 12 is a picture of a porous scaffold prepared using the method of Example 6.

In this embodiment, a VS scaffold was prepared by freezing, alkaline gelation, and vacuum drying. Briefly, Protasan (8 mg/ml) was deposited on a nylon mesh strainer with 70 μm pore size, then frozen slowly at −30° C. and placed in cold ethanol/NaOH solution (1 part saturated NaOH+50 parts 95% ethanol) at −30° C., overnight. The strainer was then transferred to pure, cold ethanol (−30° C.) and washed for ½ hr with occasional stirring, and finally vacuum-dried. A picture of the scaffold is shown in FIG. 12.

Example 7

Fabrication of VS Scaffold Using Rat Tail Type I Collagen

Figure 13:
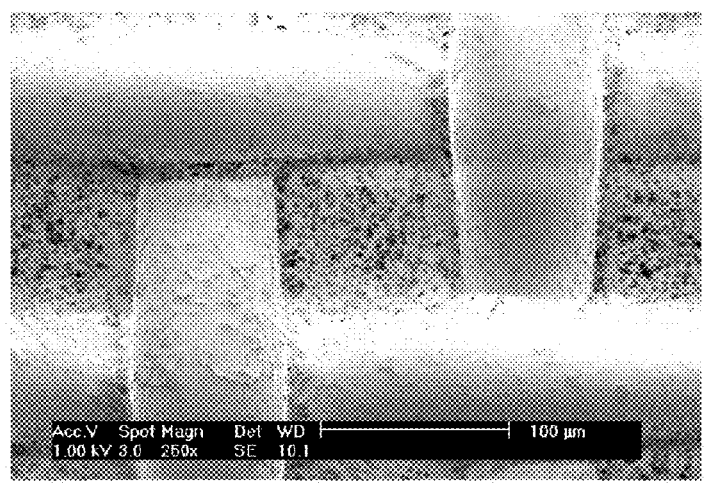
FIG. 13 is a picture of a porous scaffold prepared using the method of Example 7.

In this embodiment, the VS scaffold was prepared by leaching, alkaline gelation, and vacuum drying. Protasan (0.5 mg/ml) plus rat tail type I collagen (3.6 mg/ml) were placed in a 1.5 ml microfuge vial (200 μl collagen (3.8 mg/ml) plus ~5 μl 2% Protasan). Dry polystyrene beads (7 μm size) were added 1:1 by weight to get a paste that was centrifuged at 5000 g for 2-3 min The pellet was deposited sparingly on 100 μm pore size nylon mesh and air-dried at 60° C. The mesh was then placed in ethanol/NaOH solution at room temperature for 2 hr with slow stirring. It was then washed in pure ethanol for half hour with slow stirring. Finally, the mesh was transferred into tetrahydrofuran (THF) for 1 hr with slow stirring; it was then washed in pure ethanol and vacuum-dried. A picture of the scaffold is shown in FIG. 13.

Example 8

Fabrication of VS Scaffold Using Bovine Type I Collagen

Figure 14:
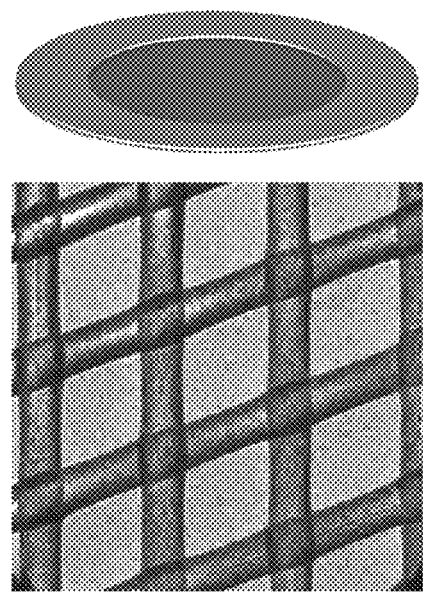
FIG. 14 is a picture of a porous scaffold prepared using the method of Example 8.

In this example, the VS scaffold comprises a continuous collagen membrane (a bovine type I collagen matrix deposited and congealed on the nylon mesh). Specifically, acidic bovine collagen (3 mg/ml) was neutralized with sodium hydroxide (NaOH) on ice and deposited onto a 100 μm pore size nylon mesh, laminated in a stainless steel O-ring so that it could be accommodated in a bioreactor. The scaffold was congealed at 37° C., 95% RH and placed in cell culture medium. A picture of the scaffold is shown in FIG. 14.

Example 9

Two-Side Culture of Human Endothelial Cells on Protasan/Collagen Porous Matrix

Figure 15:
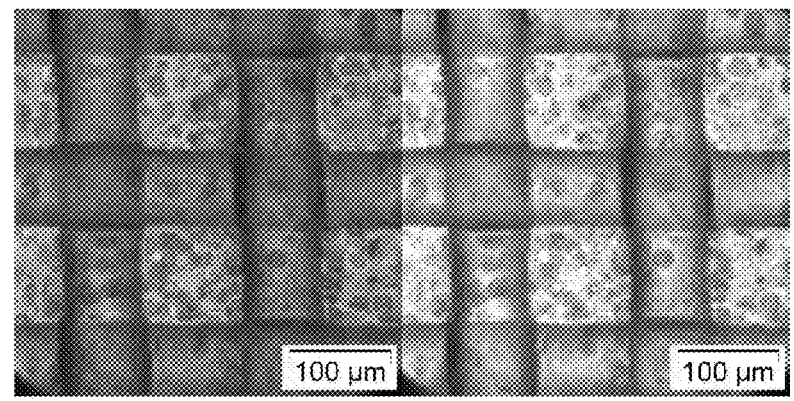
FIG. 15 shows pictures of confluent HUVEC culture on the bottom (left) and top (right) surfaces of a porous Protasan/collagen membrane supported by a nylon mesh.

In this embodiment, confluent endothelial cells were grown on the VS membrane matrix. Freshly expanded human vascular endothelial cells (HUVEC) were deposited on the bottom side of the nylon mesh strainer comprising a porous Protasan/collagen membrane. For this step, the strainer was placed upside down in a culture well. The cell suspension contained ~5×10$^5$ cells/ml. After letting the cells anchor and accommodate, another deposition of HUVEC was made on the opposite surface of the membrane, with the strainer turned in its normal position. The two-side culture was maintained in DMEM media for 12 days. Pictures of the scaffold are shown in FIG. 15.

Example 10

Permeability of the Two-Sided HUVEC Culture

Figure 16:
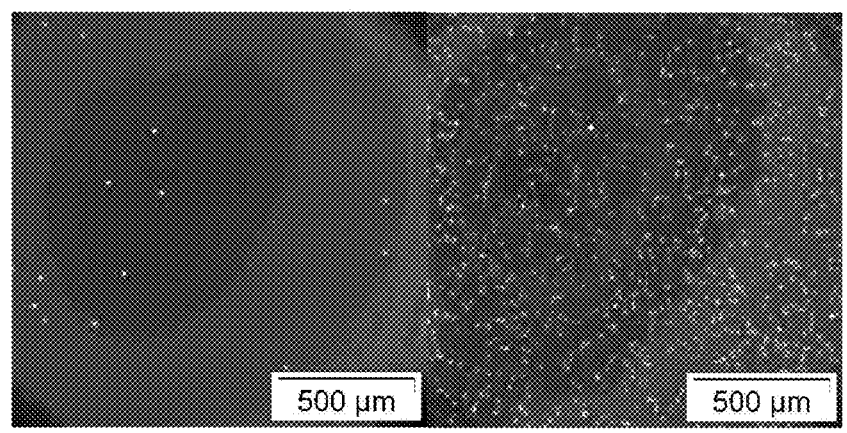
FIG. 16 illustrates monocytes migrated through the two-side HUVEC culture grown on porous Protasan/collagen mesh-supported membrane. Left: Monocytes on the bottom of the chamber without MCP-1, underneath of the two-side HUVEC culture, 30 min after application onto the membrane. Right: Monocytes on the bottom of the chamber with MCP-1, 30 min after application onto the membrane.

The permeability of the two-sided HUVEC culture to peripheral blood monocytes was examined. A specimen of the two-sided HUVEC culture grown on a Protasan/collagen porous matrix was seeded with human PBMC, with and without the monocyte-specific chemokine MCP-1 placed underneath. FIG. 16 shows monocytes on the bottom of the chamber without MCP-1 (left panel) with MCP-1 (right panel), 30 min after application onto the membrane.

Example 11

HUVEC Culture Grown on a Bovine Collagen Membrane

Figure 17:
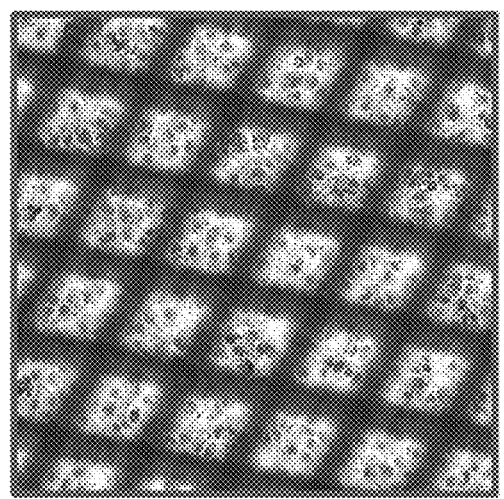
FIG. 17 is a picture showing HUVEC culture growing on a bovine collagen type I membrane.

Confluent HUVEC culture grown on a bovine collagen membrane supported by a nylon mesh. Cells demonstrated well-defined multi-angular morphology and clearly visible intercellular contacts, characteristic of successful ("happy") endothelial culture. Under proper seeding conditions, confluency was achieved in 24 hours (FIG. 17).

Example 12

Human Monocytes Permeates the HUVEC Culture

Figure 18:
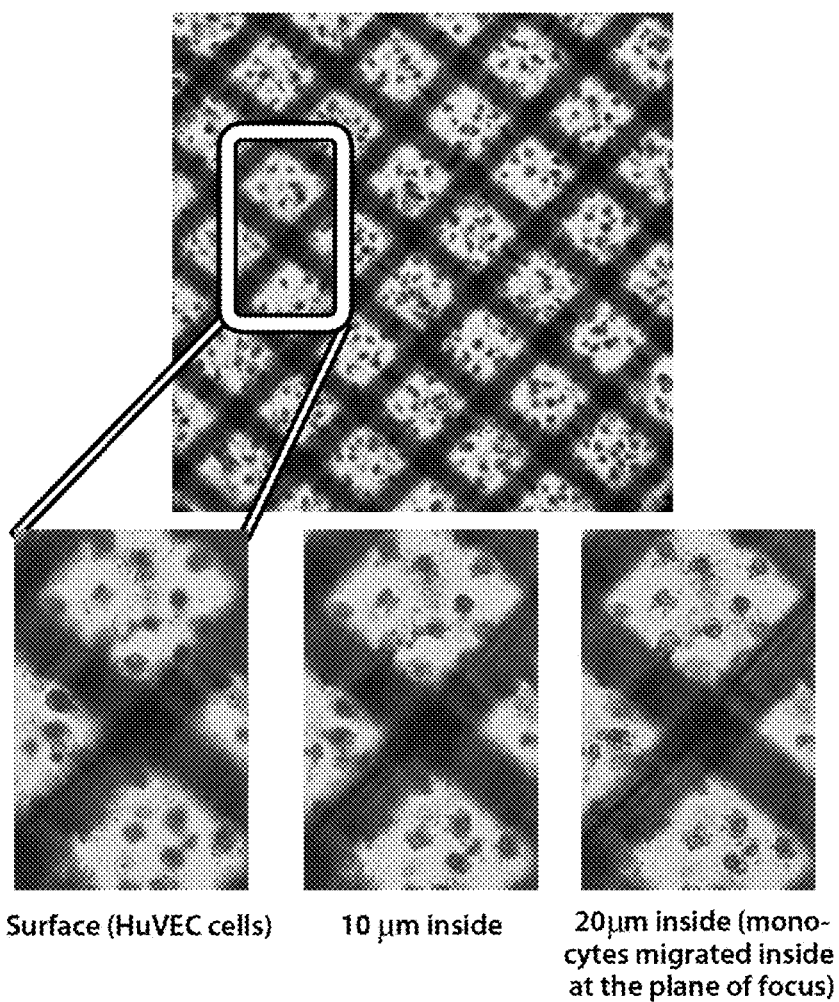
FIG. 18 is a composite of pictures showing human monocytes permeated the HUVEC culture on a collagen mesh-supported matrix.

Human monocytes permeated the HUVEC culture on a collagen mesh-supported matrix (FIG. 18). 1.5 hour after depositing human PBMCs over the HUVEC monolayer (5×10$^6$/ml), a high number of monocytes enter into the collagen cushion, traversing the monolayer in the luminal-to-abluminal direction. The figure shows toluidine blue-stained cells in the collagen attached to the ring mesh with cells 20 μm below the surface HUVEC cells.

Example 13

Construction of VS Using Skin Epithelium

In the AIS of the present invention, skin epithelium is integrated into the 3D tissue construct so that DC precursors can take up residence in the epidermis and normal immunophysiology is maintained. In this embodiment, the complexity of the vaccination site is increased to include key elements of the skin is based on the fact that skin is the most common site of immunization. Indeed, some of the latest vaccine candidates that appear promising are actually skin patches applied to the epidermis.

Figure 11:
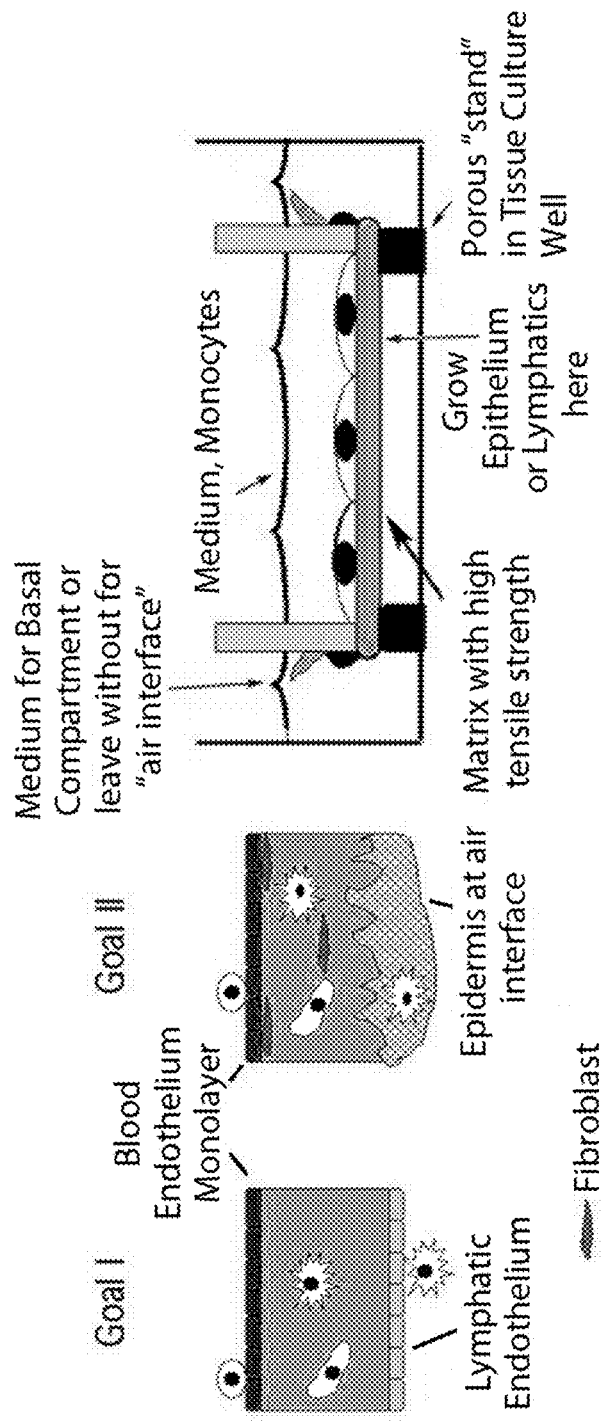
FIG. 11 is a schematic representing a 3D model of a vaccination site (VS).

A good source of skin is freshly isolated cadaveric skin from consenting organ donors. This split thickness skin is sufficiently functional to support migration of DCs through dermal lymphatics (Lukas, et al., *J. Invest. Dermatol.* 106: 1293-1299 (1996)) and it has previously been used to verify and identify novel mediators of DC migration from the epidermis (Randolph, et al., *Proc. Natl. Acad. Sci. USA*, 95:6924-6929 (1998c); Robbiani, et al., *Cell*, 103:757-768 (2000)). Thus, authentic skin can be used to compare with the model of skin of the present invention; explants for sources of keratinocytes, fibroblasts, endothelium, DCs, and dermal matrix can also be used (FIG. 11).

Example 14

Construction of VS

The integration of Langerhans cells in "skin equivalents" has been addressed (Regnier, et al., *J. Invest. Dermatol.* 109: 510-512 (1997); Fransson, et al., *Br. J. Dermatol.* 139:598-604 (1998)). These are encouraging descriptions, as one of the models showed that keratinocytes could support Langerhans cell differentiation from CD34+ progenitors naturally without the addition of exogenous cytokines (Frans son, et al., Supra (1998)).

In another embodiment of the present invention, epidermal cells are grown at the air interface, to permit stratification of the various normal layers of skin. On the other side of the matrix vascular endothelial cells are cultured. At a later time, adult PBMCs or cord blood PBMCs enriched in CD34+ cells are applied to assess whether monocytes or other DC precursors were recruited not only across the endothelium, but whether these cells migrate across the matrix, as if traversing the dermis, and then move into the epidermal layer to occupy it with integrated Langerhans cells. If integration is observed, the integrated cells can be retrieved to determine whether they acquired features specific to Langerhans cells, such as the Birbeck granule. Keratinocytes can also be seeded on the undersurface of a matrix with strong tensile strength. Matrices with such strength are readily stretched across various templates, such as Teflon rings (Randolph & Furie, *J. Immunol.* 155:3610-3618 (1995)). These Teflon rings have been further designed so that the stretched matrix provides a "floor" to a culture well.

Figure 19:
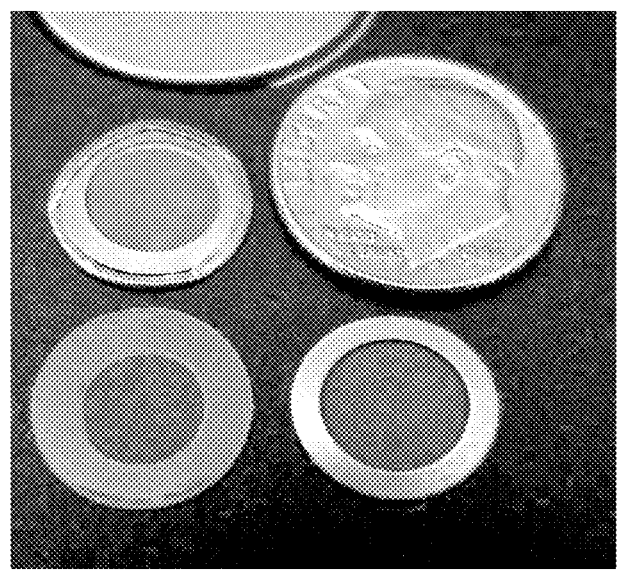
FIG. 19 is a picture of synthetic and natural membranes supported by stainless steel rings.

Creating insert supports for both synthetic and natural membranes has been accomplished using laminates, crimped rings, and adhesives. Laminates and adhesives have primarily been used to support polymer meshes, which in turn are provide mechanical strength to synthetically formulated biological membranes. Fabrication using the laminate process comprises sandwiching a stretched mesh between two pieces of polymer laminate, which are then sealed together, e.g., thermally. The adhesive method consists of stretching a mesh support and adhering a ring (comprising, e.g., stainless steel) using a biocompatible glue. The crimping method is shown in FIG. 53; in this, the membrane is compressed between two rings of suitable material, e.g., stainless steel. Generally, the laminate and adhesive methods are preferred for synthetic mesh supported membranes, while the crimping method can accommodate both natural, biological membranes and synthetic meshes. FIG. 19 shows pictures of membranes crimped in between thin stainless steel rings. Using the crimping method, biological membranes can be supported without the use of adhesives and pressed into a disk with thickness profile of about 400 µm or less. Epithelium is then grown on the topside or underside of the matrix, which can be left at the air interface by setting the structure on an inert, porous "stand" placed inside a tissue culture dish. Endothelium is then grown on the other side of the matrix to form a monolayer on the inner surface of the culture ring, to which culture medium can be added (FIG. 11, right panel).

FIG. 65 is a picture of ring structures showing variable methods of attachment of membranes for VS in the bioreactor. The left panel shows the spiked ring design used to hold 'wet' membrane structures such as amniotic or UBM naturally occurring ECM membranes. The right panel shows three methods used to attach 'dry' synthetic membranes to the ring structure. Top left (next to the left side of the dime) is crimped, bottom left is by laminating the membrane between two rings of the same material, and bottom right (below the dime) is glued. A variety of biologically cell-friendly cyanoacrylates, epoxies, and silicones have been successfully used in attaching meshes to the rings. FIG. 66 shows HUVEC cells on the culture plate with a bead of Devon two-part epoxy applied and polymerized in place prior to seeding. No ill affects on the cells were observed after 72 hours and cells reached confluence after 48 hours.

Because endothelial cells could be grown on human amniotic connective tissue, an acellular natively polymerized human connective tissue, in a noninflamed setting (Furie & McHugh, *J. Immunol.* 143:3309-3317 (1989)), amniotic matrices were prepared from human placenta. Vascular endothelium were grown on both sides of the amniotic matrix (FIG. 47) without underlying inflammatory signals, because on this matrix, neutrophils could be added without being recruited across the endothelium (only about 1% of neutrophils added migrated in these cultures, within the range considered to be noninflammatory (Furie & McHugh, *J. Immunol.* 143: 3309-3317 (1989)). A positive control for "inflammation" in these experiments was to stimulate some of the endothelial/amnion constructs with the pro-inflammatory cytokine, IL-1 an average of 76% of neutrophils migrated in the same experiments with IL-1, where only 1% migrated in its absence) (FIG. 47). These results demonstrate: (a) construction of a culture system that supported growth of two layers of endothelium and (b) construction of culture system that is not inherently inflammatory, but which can become so in response to appropriate stimuli (e.g., IL-1).

In addition to having endothelial layers to control recruitment into and out of the vaccination site, other cell types can be added to the cultures (e.g., fibroblasts; they are a normal component of all tissues). The isolated and cultured primary human fibroblasts were obtained from human placenta. These cells were seeded in the matrix after the addition of the first endothelial layer, but before the addition of the second endothelial layer. Fibroblasts incorporated themselves in the constructs and took up residence in the matrix that was sandwiched by the two layers of endothelium (FIG. 47).

Monocytes are one type of DC precursor; they can also develop into macrophages. Monocytes were seeded onto the dual endothelial/amnion constructs, and migration of monocytes across the entire construct was observed, although many monocytes stayed relatively close to the original endothelial layer (FIG. 47). This demonstrates that all parts of the matrix are "cell friendly" and accessible for migration. In contrast to neutrophils, monocytes can migrate across endothelium in the absence of inflammation, because endothelium constitutively produces the factors that support their migration.

In another embodiment, a good choice of matrix may be acellular human dermis itself; it is feasible to make such matrices from the split thickness skin discussed earlier. There are several methods to remove the sheet of epidermis (Dispase or ammonium thiocyanate), and remaining sheets that are of appropriate thickness can be selected to establish the desired construct in which vascular endothelium is cultured on one side and epidermis on the other. This design takes into account the incorporation of transmigrating blood cell precursors into Langerhans cells in the epidermis, DCs of the dermal type in the matrix, together with macrophages that take up residence in the matrix.

Example 15

Communication Between VS and LTE

The VS can be placed in communication with the artificial lymph node (LTE) of the present invention. Such direct communication can be achieved by inclusion of a flow chamber that permits such communication. For this embodiment, digital printing technology may be desirable.

Figure 20:
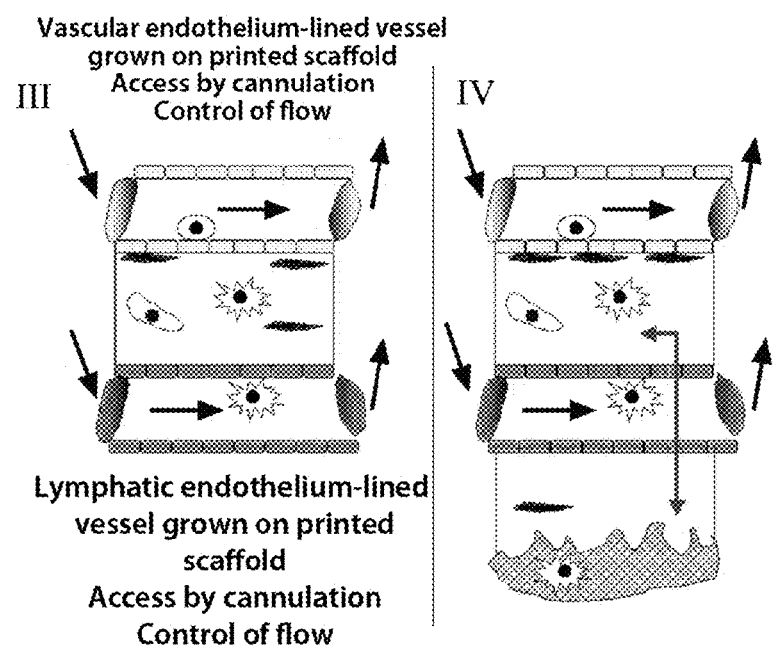
FIG. 20 is a schematic representation of an embodiment of an in vitro vaccination site.

FIG. 20 illustrates aspects of the present invention. In an embodiment, scaffolding for flow-supported, cannulated, endothelial cell lined tubes are constructed using digital printing technology. Preferably, this will include an epithelial layer (IV), but can also be a more simple vascular structure (III). The red arrow indicates the 3D nature of the construct in which the tubes are fully surrounded by connective tissue matrix. In an embodiment of the present invention, the construct has lymphatic and vascular tubes intertwined and positioned near dermal papillae, as occurs naturally in skin.

With this advanced in vitro skin equivalent construct that replicates the functional architectural and immunophysiology of natural skin, it is possible to test compounds in vitro. The VS is an accurate, reliable and reproducible means to replace animal systems for safety testing of cosmetics, chemicals, lotions, creams, adjuvants, vaccines, drugs, biologics, and other compounds.

For reasons of safety and risk assessment, new chemicals are presently evaluated for irritant potential by application to animals and observation of visible changes, such as erythema (skin redness) and edema (accumulation of serous fluid). Testing for skin irritation in animals potentially causes them pain and discomfort and the results are not necessarily predictive of those in humans. In recent years, animal testing for dermatotoxic effects has come under increasing scrutiny and criticism from animal-rights activists as being inhumane and unnecessary. Attempts have been made to restrict the marketing of products containing ingredients that have been tested on animals. The often conflicting needs to protect worker and consumer safety, comply with regulatory statutes, and reduce animal testing procedures are leading to a significant effort within industry, government, and academia to develop alternative testing methods for assessing the skin corrosion and irritation hazards of chemicals and product formulations without reliance on animal test procedures.

There is a continuing need for standardized, validated in vitro assays that provide dependable, predictive safety data for the broad range of products in the cosmetic, personal care, chemical, household products, and pharmaceutical industries. Factors driving the development of in vitro models include the frequent lack of correlation between animal data and the human response, the importance of human correlation test data using 3D tissue engineered constructs, increased sensitivity, better control conditions, better experimental flexibility, easier diagnostics, and the significant expense and time required for in vivo animal studies.

A major advantage of an in vitro model is that it boasts a rapid turn-around time for data analysis and decision-making via a clearer interpretation of sophisticated multi-endpoint data. The most prominent question guiding dermato-toxicologist is whether skin equivalents composed of keratinocytes and fibroblasts are sufficient to evaluate the irritant potential of substances. Certainly, a significant difference between in vitro equivalents and natural skin is the composition of the cells and the absence of communication with other tissues.

For evaluation of visible symptoms following irritation, the interaction of blood vessel endothelium, inflammatory cells, and nerves is necessary and heretofore has been largely ignored. In the present invention, an advantage is that the VS comprises blood and lymphatic endothelia as well as various immune cells (monocytes, dendritic cells, mast cells, macrophages, neutrophils, fibroblasts), cell types important for evaluating inflammatory responses to irritants, scaffold materials, and the assemblage of such a construct. These additions are important to achieve a valid physiological response to properly assess the cosmetic, chemical, drug, biologic, vaccine or adjuvant in question.

An embodiment of the present invention comprises a tissue engineered scaffold to integrate vascular tubes into constructs lined with vascular and lymphatic endothelium, with and without epidermal epithelium. This requires identifying conditions that permit growth of the desired cell types in a cannulated scaffold at a known blood flow rate through postcapillary venules. With this design, the result is a more realistic vaccination site. For example, with a continuous flow loop of leukocytes through the vascular compartment, administration of an inflammatory stimulus to the connective tissue space would allow all recruitment of cells to occur with their normal kinetics and normal endothelial cues, such that the endogenous environment would orchestrate the entire response to the administered vaccine. Cells could be collected from the lymphatic cannula for analysis, or this cannula could be established to communicate with the artificial lymph node In a tissue engineering approach to forming a VS tissue, having determined desired cell types and scaffold characteristics, in one embodiment, a digital printing system is used to form the scaffold and to seed cells into a configuration amenable to the final AIS bioreactor format. Deposition conditions include:
1. BAT handling of cells,
2. optimal scaffold pore size and framework dimensions,
3. scaffold characteristics for each tissue type,
4. interfacing/connecting scaffolds for various tissue types and fluid/nutrient paths,
5. materials to prevent cell adherence to non desired bioreactor surfaces including adherence of cells to scaffold areas devised for other tissue types,
6. cell seeding density for each tissue type,
7. order of cell seeding (simultaneously or staged; and how to achieve in final bioreactor configuration), and
8. integration and digital printing of methods into final bioreactor configuration.

Difficult engineering challenges in making engineered human tissues according to the present invention include the delivery of nutrients and uniform seeding of cells throughout the scaffold or growing tissue construct. In a preferred embodiment, the digital printing BioAssembly Tool (BAT) system is used to create 3D interwoven structures of nutrient, oxygen and tissue paths. The BAT prints cells into the appropriate path and the materials used to make each path are conducive to growth for a particular type of cell, but inhibitory to others. For example, only endothelial cells would attach to and line oxygen delivery channels. Only stromal and parenchymal cells would anchor in the tissue areas. Adjacent areas will likely have to be inhibitory to undesired cell types, as it is our experience that if an engineered tissue is put in contact with a 2D surface, cells migrate out of the tissue and form monolayers on the 2D surface. Because of this, in the present invention, 3D cultures are preferably grown suspended in medium, away from any 2D bioreactor surfaces. In a preferred embodiment, the BAT can be used to create this structure.

If an engineered tissue adequately mimics the in vivo setting, the tissues will respond as they do in vivo. Hence, it is possible that if an engineered skin equivalent is injected with an antigen and put in contact with a fluid stream containing monocytes, the skin equivalent itself may create the chemokines necessary to attract monocytes.

Immature DCs are recruited to sites of inflammation in peripheral tissues following pathogen invasion; this is to directing cells to the VS (skin equivalent) in the in vitro immune system of the present invention. Internalization of foreign antigens can subsequently trigger their maturation and migration from peripheral tissues to lymphoid organs. Chemokine responsiveness and chemokine receptor expression are important components of the DC recruitment process to sites of inflammation and migration to lymphoid organs Immature DCs may express chemokine receptors including CCR1, CCR2, CCR5, CCR6, and CXCR1.14, 15. They can thus be chemoattracted to areas of inflammation primarily by MIP-3β, but also in response to RANTES (regulated on activation, normal T cell-expressed and secreted)/CCL5 and MIP-1α (macrophage inflammatory protein-1α)/CCL3.16. Following antigen acquisition and processing, DCs migrate to T cell rich areas within lymphoid organs via blood or lymph, simultaneously undergoing maturation and modulation of chemokine and chemokine receptor expression profiles. A change in expression levels of the chemokine receptors CCR6 and CCR7 contributes to the functional shifts observed during DC maturation.

To orchestrate all of these migratory routes to the VS (monocytes), out of the VS (mature DCs), and into the LTE (mature DCs, T and B cells), it is an important feature of the present invention to incorporate chemotaxis into the in vitro immune system. An important materials/device design feature is the incorporation of the messages, soluble and insoluble molecules that promote cellular attraction. Further, development of a complete LTE requires signal delivery to T and B cells as well, to provide cues to organize these cells on the LTE scaffold.

Example 16

The Rapid Chemokine Testing System

The BioAssembly Tool (BAT) has been modified for use in observations of the lateral motility of cells in experiments on chemotaxis. The described setup enables rapid screening of chemokines and cell matrices (typically, one experiment can take about half to one hour).

Figure 21:
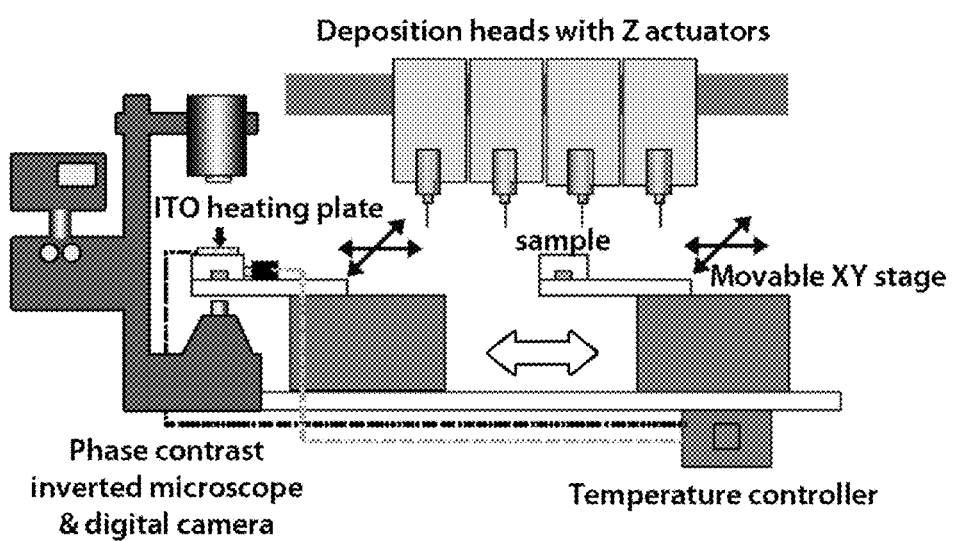
FIG. 21 is a schematic picture of a rapid chemokine testing system.

Three chemokines, fMLP-FITC; MIP-β (macrophage inflammatory protein-β), and MIP-3β, were tested with human monocytes. It was found that the saturation level for fMLP FITC (N-formyl-methionyl-leucyl-phenylalanine-fluorescein isothiocyanate) (~40 nM) was close to that known for fMLP (N-formyl-methionyl-leucyl-phenylalanine) (~30 nM). MIP-3β was found ineffective (as expected for immature monocytes); MIP-3α was found effective, despite negative information and expectations. It was also found that fibrin glue effectively arrested cell motility even at low concentration (~1 mg/ml), whereas collagen favored motility. Thus, fibrin matrices should be used preferably in cases when cell retention is required, and collagen should be used to make cell-permeable barriers. This latter observation may be important when considering the use of ETCs for wound healing procedures. A schematic picture of the rapid chemokine testing system is shown in FIG. 21. This system can be used to further refine and optimize chemokine doses using various microparticle strategies and formulations, temporal release characteristics, and scaffold characteristics (e.g., geometry, porosity, material) on cell migration.

The rapid chemokine testing system can be used to examine saturation of cell receptors by chemokines. When a chemokine reaches its saturating concentration, cells become insensitive to the signal and stop their locomotion. In most cases, chemotaxis occurs through gradients of chemokines. The steeper the gradient, the more effective the attraction; in the same time, the shorter the distance that can be covered by the gradient before saturation is achieved.

Example 17

Cell Maturation in LTE

This example relates to the lymphoid tissue equivalent (LTE) which is also referred to as the artificial lymphoid tissue. LTE is the command center of the artificial (ex vivo) immune system that contains the naive and/or memory T and B lymphocytes. T and B cells play key roles in adaptive immunity by destroying infected cells, producing antibodies that opsonize pathogens, and secreting cytokines that induce effector functions in other immune cells. Activation of naive lymphocytes occurs within secondary lymphoid tissues (including lymph nodes, Peyer's patches, spleen). T cells are activated by antigenic peptides presented to them in the cleft of class I and class II MHC molecules by dendritic cells emigrating from the periphery to the lymph nodes, while B cells are activated by direct binding of foreign molecules with their antigen receptors and subsequent interactions with activated T cells.

T cells, B cells, and DCs in lymph nodes are found in two anatomically distinct regions (FIG. 22). These are the paracortex or T zone (home to T cells and dendritic cells) and the follicles (home to B cells and associated supporting cells, including follicular dendritic cells).

During resting homeostasis, T and B cells continuously recirculate through the blood between secondary lymphoid organs. T and B lymphocytes enter the lymph nodes from the blood via specialized vessels known as high endothelial venules (HEVs) in the paracortex, and are directed toward the T zone or follicles by specific chemokines produced in each zone. T and B cells typically reside within a given lymph node for 24-48 hrs, and if activation signals are not encountered, they move on to continue their recirculation via the blood to other secondary lymphoid organs.

On initiation of an immune response, these cells leave their respective zones and follow a program of cell-cell interactions in an orchestrated fashion within the lymph node. These steps in the generation of adaptive immune responses are discussed below.

Figure 23A:
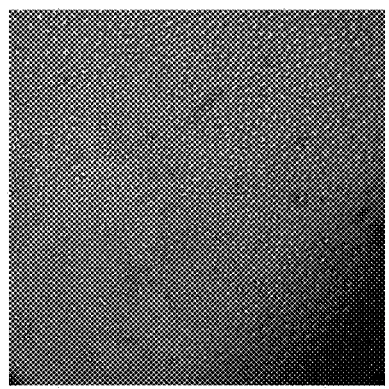
FIGS. 23A-23I are phase contrast micrographs of a confluent monolayer of HUVEC cells on a collagen cushion.
Figure 23C:
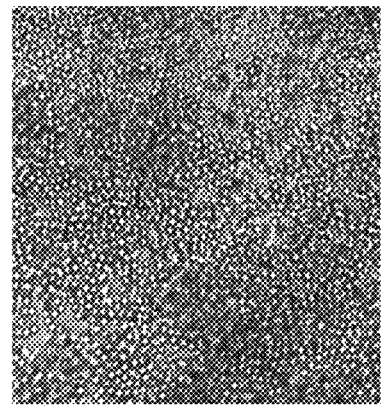
Figure 23B:
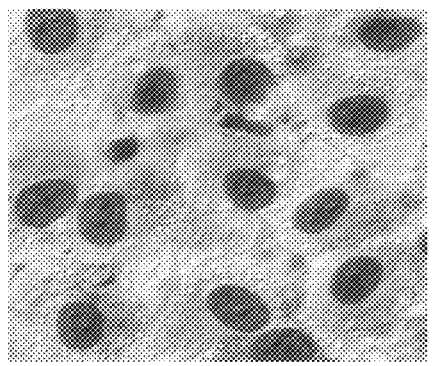
Figure 23D:
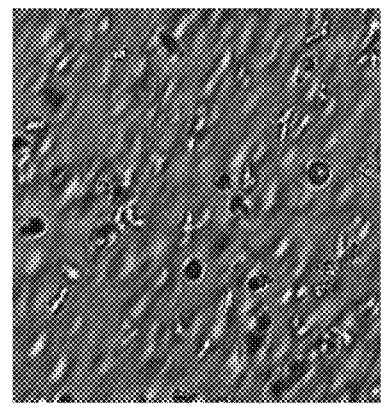
Figure 23E:
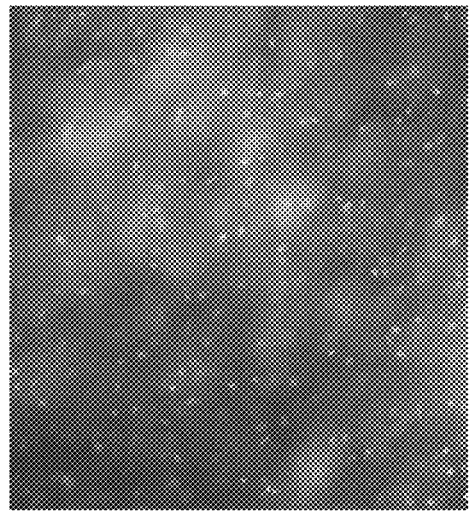
Figure 23F:
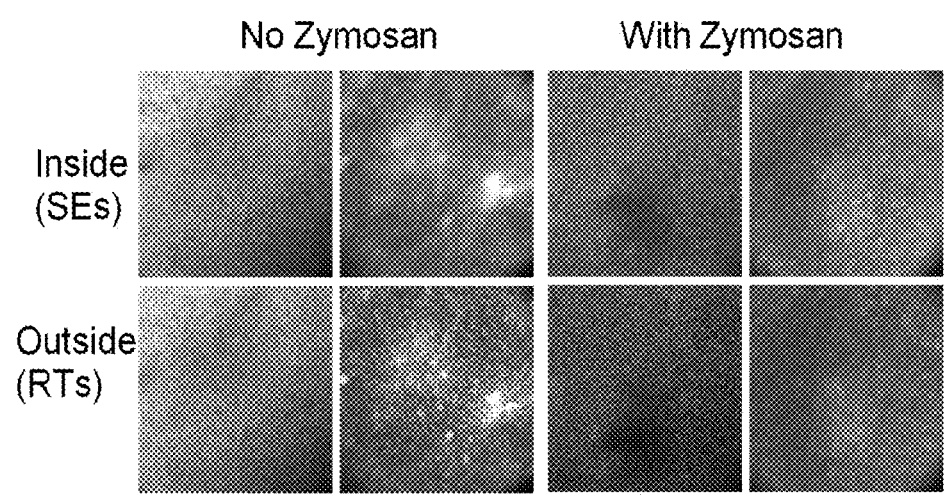
Figure 23G:
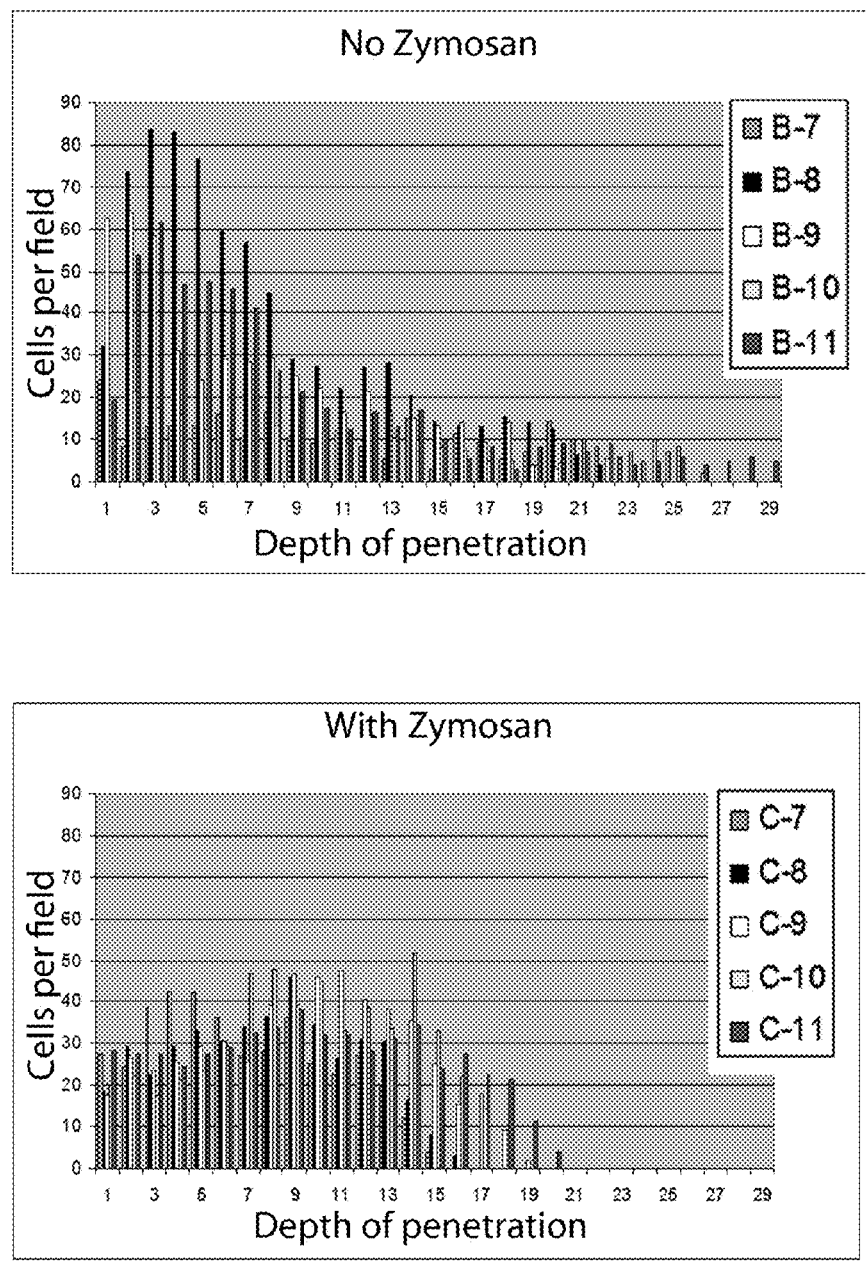
Figure 23H:
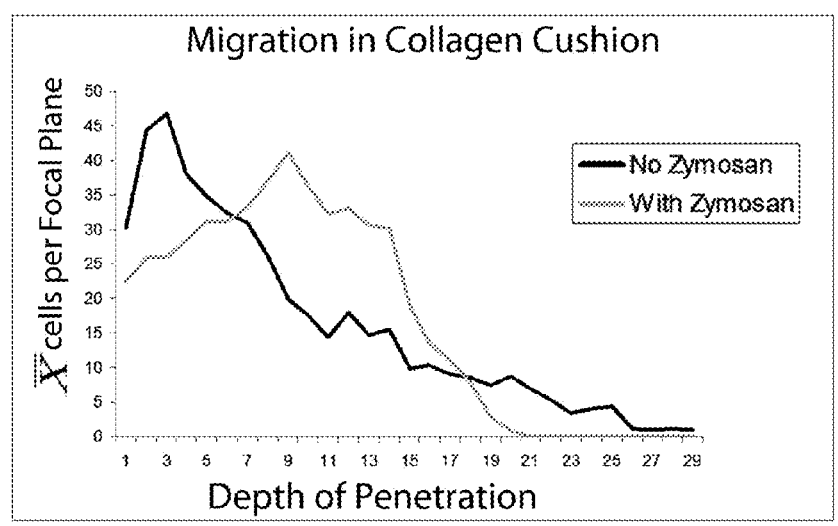
Figure 23I:
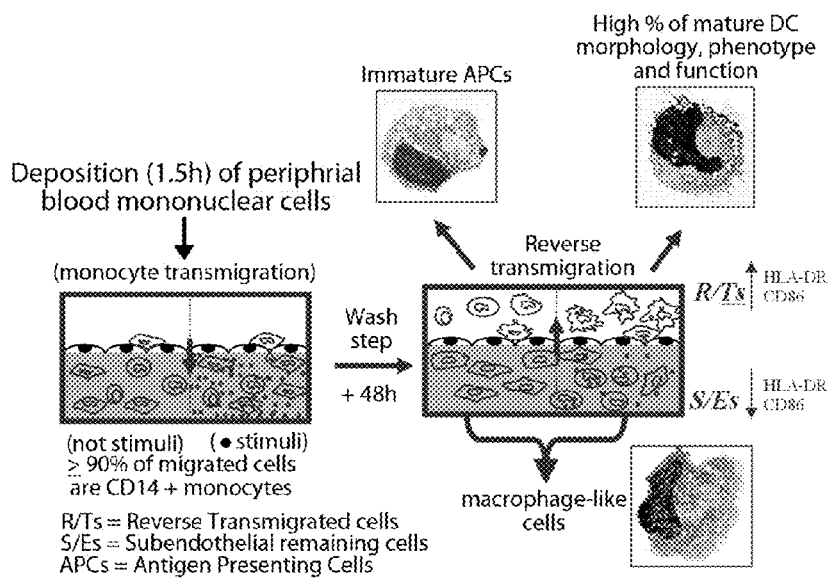

In an embodiments of the present invention, synthetic and/or natural ECM materials may be used to fabricate matrices for the LTE to achieve 3D structures that provide a physical structure mimicking the lymph node's "open" reticular network, containing lymphocytes, as well as biochemical cues (e.g., adhesion motifs, chemokine gradients) expected by lymphocytes in secondary lymphoid tissue. In addition, hybrid approaches can be used that combine the controlled microstructure design of synthetic approaches with the more native materials of natural ECM. Example LTE structures comprising segregated T and B zones can be fabricated with overall structures mimicking the physical arrangement shown in FIGS. 23A-23I. Briefly, FIGS. 23A and 23B is an image of toluidine blue-stained HUVEC cells on a collagen cushion, showing characteristic cell packing. From the time of seeding the HUVEC cells on a collagen cushion, it typically takes about 5 days from confluency to occur and for the cells to take on the normal vascular endothelial morphological characteristics. FIG. 23C shows a high density of newly applied peripheral blood mononuclear cells (PBMCs) on the layer of HUVEC. FIG. 23D shows a focal plane below the HUVEC cells, within the collagen matrix, 45 minutes after the application of PBMCs. Cells in focus are within the collagen and are easily distinguished between HUVEC and surface PBMCs. In FIG. 23E, CMFDA labeling was done to show cell viability and position of live cells within the collagen cushion. FIG. 23F shows transmigration of PBMCs into collagen cushions without or with the presence of Zymosan. Phase contrast, and CMFDA labeling was done to determine cell placement within the cushion. Z-stack images were taken through the entire cushion to determine the numbers of cells within the cushion and those that had undergone transmigration. Data analysis showed increased numbers of transmigrated cells remained in the cushion in the presence of Zymosan as compared to cushions with no Zymosan (FIGS. 23H and 23G). Transmigrate cells in the presence of Zymosan did not penetrate as deeply, because of the stimulatory nature of Zymosan.

Characterization of the HUVEC endothelial cells in the collagen cushion is paramount to showing a confluent layer, and appropriate morphological characteristics which will allow the highest number of PBMCs migrating into the collagen cushion. As shown in FIG. 58, the HUVEC cells maintain a confluent monolayer with typical morphologic characteristics after 10 days of culture (panel B: These morphological characteristics are important to maintain prior to PBMC application.

The role of lymphoid tissue stromal cells in supporting T and B cell functions in these LTE matrices can be assessed to further determine how lymph nodes form in vivo and to identify key factors controlling lymph node self-organization.

Primary immune responses are initiated by dendritic cells presenting foreign peptides in the cleft of major histocompatibility complex (MHC) molecules to the T cell receptor (TCR) of antigen-specific, naive T cells (Banchereau & Steinman, Nature 392:245-252 (1998); Banchereau, et al. Annu. Rev. Immunol. 18:767-811 (2000)). On contact with their cognate antigen presented by DCs, T cells remain in lymph nodes for 2-4 days, undergoing differentiation/clonal expansion and providing help to antigen-specific B cells, before exiting the lymph nodes to carry out effector functions in the periphery (Butcher, et al., Adv. Immunol. 72:209-253 (1999); Sprent et al., Cell. Immunol. 2:171-181 (1971)).

Figure 24:
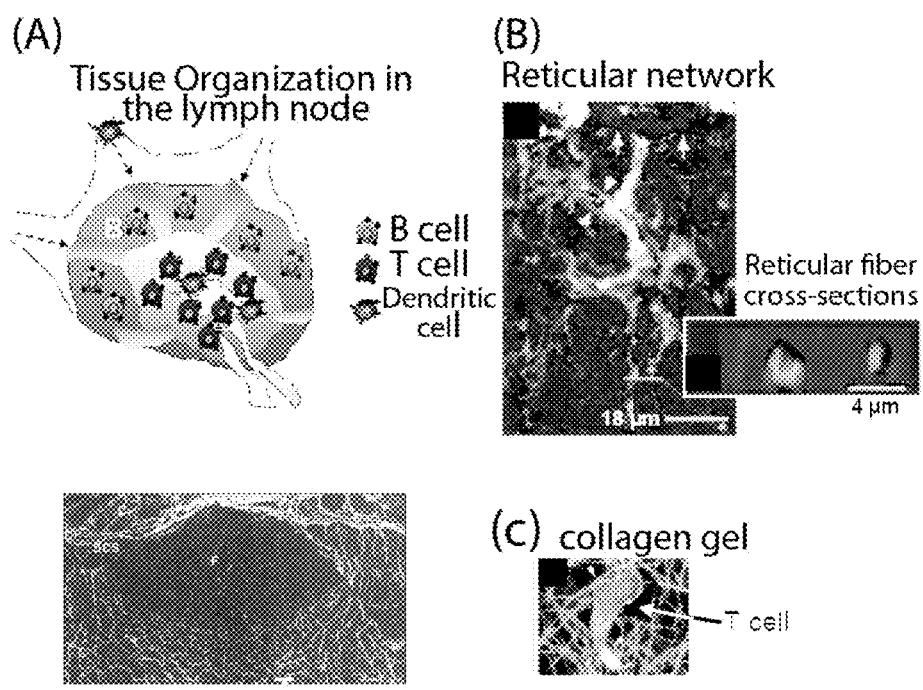
FIG. 24A-24C show organization of the T-zone of the lymph node.
Figure 25:
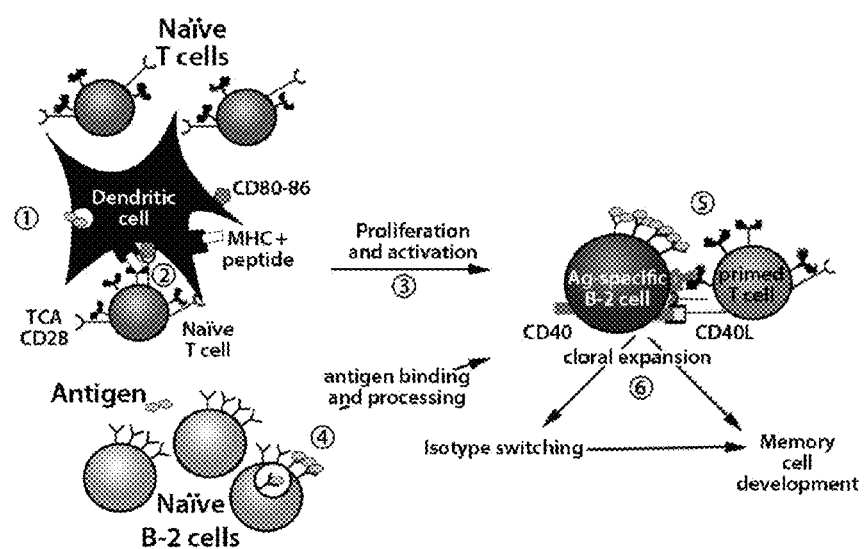
FIG. 25 shows a model of B cell activation in lymph nodes (from Baumgarth Immunol. Rev. 176:171-180, (2000)).

Naive T cell activation occurs in the T zone of lymph nodes (FIG. 24); T cells search for antigen-bearing DCs that have migrated to the T zone via blood or lymph from sites of infection in the peripheral tissues (Garside, et al., Science, 281:96-99 (1998); Jenkins, et al., Annu. Rev. Immunol. 19, 23-45 (2001); Kaldjian, et al., Int. Immunol. 13, 1243-1253 (2001)).

Unlike the fine collagen fibril mesh of peripheral connective tissues, the extracellular matrix of the T zone is organized in an open, web like system of collagen fibers, known as the reticular network (Kaldjian, et al., Int. Immunol. 13:1243-1253 (2001)). These thick (about 0.5 to about 5 µm diameter (Gretz, et al., J. Immunol. 157:495-499 (1996)) fibers are spaced about 20 to about 30 µm apart (FIG. 24); the contrast between the structure of the reticular network and that of a typical collagen gel is illustrated in FIG. 24. The reticular fibers consist primarily of collagen I, collagen III, and fibronectin (Kaldjian, et al., Int. Immunol. 13:1243-1253 (2001); Gretz, et al., Supra (1996)) and support the attachment of a layer of stromal cells, known as fibroblastic reticular cells (FRCs) via β1-integrins (van den Berg, et al., Am. J. Pathol. 143:1098-1110 (1993); Gretz, et al., J. Exp. Med. 192:1425-1440 (2000)). FRCs ensheath reticular fibers and join one another with tight junctional complexes (Stuart & Davidson, J. Pathol. 103: 41-47 (1971)) to form a "living substrate" for T cell and dendritic cell migration (Crivellato & Mallardi, J. Anat. 190:85-92 (1997)).

The T zone is also compartmentalized from bulk flow of lymph or blood, which may preserve a particular controlled microenvironment in the T zone during immune responses (Gretz, et al., J. Exp. Med. 192:1425-1440 (2000)). T cell activation thus occurs within the stromal cell latticework under conditions where exogenous factors are minimized and conversely, factors secreted by dendritic cells and stromal FRCs may have maximum potency. Once CD4+ T cells are activated by DCs, they may migrate to the periphery of the follicles to provide 'help' to activated B cells for proliferation and antibody isotype switching (Garside, et al., Science 281: 96-99 (1998)).

While it remains unclear whether the unique microenvironment of the T zone is absolutely required for naive T cell activation, several lines of evidence point to its importance in mounting efficient and effective responses to pathogens. In mice lacking the chemokine receptor CCR7 (CCR7−/−), T cells and DCs do not meet in the T zone and these mice are unable to mount immune responses (Forster, et al., Cell 99:23-33 (1999)). Mice bearing a mutation (plt/plt) causing disruption of T zone architecture show a high susceptibility to some (though not all) viruses, delayed T cell responses, and aberrant T cell expansion/survival (Gunn, et al., J. Exp. Med. 189:451-460 (1999); Junt, et al., J. Immunol. 168:6032-6040 (2002); Mori, et al., J. Exp. Med. 193:207-218 (2001)). In vitro studies of T cells interacting with DCs in 3D collagen gels have shown very different dynamics for the duration and number of T cell DC contacts occurring, compared to simple liquid phase cocultures (Gunzer, et al., Immunity 13:323-332 (2000)), and recent in vivo studies imaging T cell DC interactions in intact lymph nodes confirm that these cells behave very differently in their native 3D microenvironment compared to 2D cultures (Miller, et al., *Science* 296:1869-1873 (2002); Stoll, et al., *Science* 296:1873-1876 (2002)).

Example 18

Activation of B Cells

Figure 27:
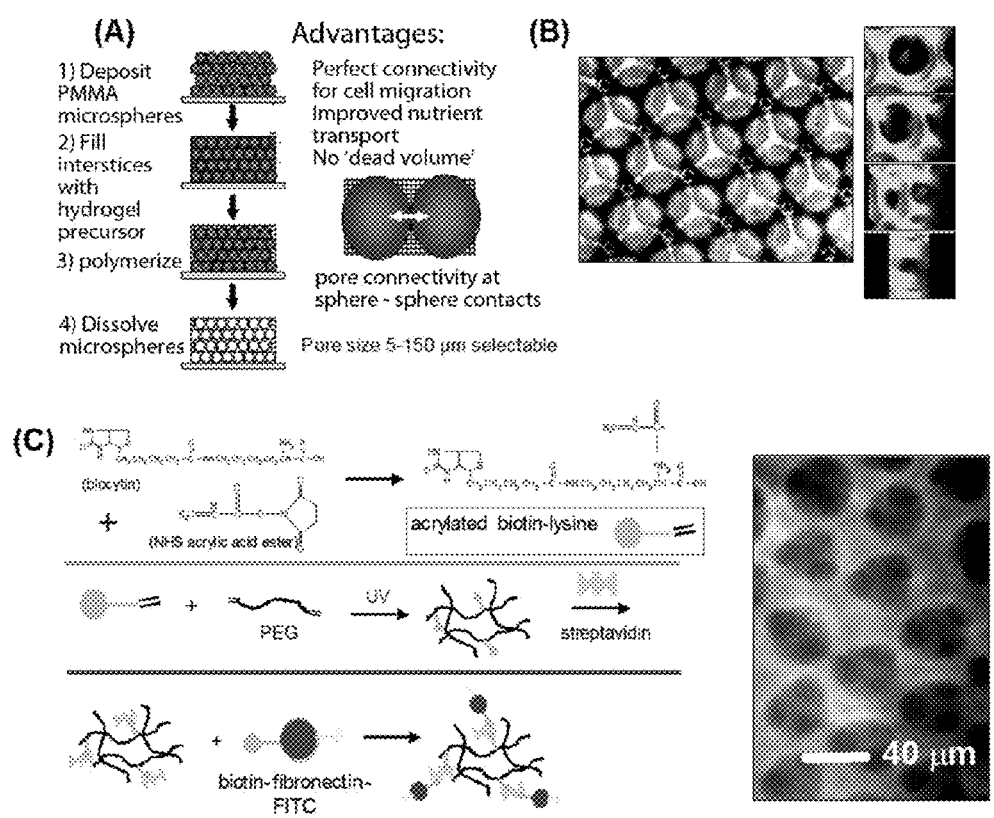
FIGS. 27A-27C show matrix design for the lymphoid tissue equivalent. (A) Approach for fabricating ordered scaffolds for the LTE. (B) Example bright field micrograph showing the highly ordered nature of the hydrogel scaffold (view through several layers observed in situ in medium). (C) Chemistry for surface bio functionalization of matrices. Shown on the right is a fluorescence micrograph of a scaffold functionalized with FITC labeled fibronectin.

The current model of B cell activation in primary immune responses is illustrated in FIG. 27 (from Baumgarth, Immunol. Rev. 176:171-180 (2000)). B cells in follicles first bind soluble antigen carried to the lymph node by the lymphatics, which triggers their migration to the edge of follicles where they meet activated CD4+ helper T cells. The activated CD4+ cells then provide 'help' in the form of CD40-CD40 ligand interactions and cytokines that promote B cell proliferation and isotype switching.

This model is in accordance with many studies showing that strong humoral immune responses to most antigens require the presence of activated CD4+ T cells (Fulcher &

Basten, Int. Rev. Immunol. 15:33-52 (1997); Parker, Annu. Rev. Immunol. 11:331-360 (1993); Goodnow, et al., Adv. Immunol. 59:279-368 (1995)). This pattern of B cell trafficking has been visualized in lymph nodes of mice (Garside, et al., Science 281:96-99 (1998)).

Following interactions with T cells, some activated B cells proceed to germinal centers, specialized regions of the follicles which develop during immune responses. Within follicles, B cells proliferate and undergo somatic hypermutation, a process designed to genetically manipulate the antibody specificity of activated cells to find high affinity mutants that can more effectively eliminate pathogens.

Specialized dendritic cells (follicular dendritic cells) capture antigen antibody complement complexes and present them to the antibody rearranging B cells in the germinal centers; those B cells that develop higher affinity antibodies (expressed in membrane bound form on their surface) are given survival and proliferation signals, while B cells whose antibody chains become unable to recognize the antigen apoptose (Kosco Vilbois, Nat. Rev. Immunol. 3:764-769 (2003)). The result is a rapidly expanded population of isotype switched, high affinity antibody producing B cells, which finally either differentiate into long lived plasma cells or memory B cells.

Two points are particularly relevant for the development of a simplified, functional model of the immune system in vitro, such as the AIS of the present invention. First is the important nature of T cell help in producing B cell proliferation and isotype switching. The second is the lack of clarity as to whether germinal center reactions are absolutely required for isotype switching, affinity maturation, and memory cell development.

In addition to effects on cellular states within the lymph node, it is likely that a 3D matrix is important to allow T cell DC interactions and the T and B cell migration that facilitates delivery of help for B cell activation and antibody production. Many animal studies have provided evidence that T cell help is important for strong antibody responses. Thus, a lymphoid tissue equivalent must support T cell-B cell interactions. In the present invention, the 'matching up' of rare antigen specific T and B cells is achieved via a LTE structure that allows the natural "self assembly" process that brings these cell populations together by autonomous migration in the lymph node.

In addition to effects of the 3D supporting matrix, cellular interactions are important in the lymph node. This likely includes interactions between lymphocytes and stromal cells. Recent studies have shown that survival and function of B cells is enhanced in vitro when they are cocultured with secondary lymphoid tissue stromal cells (Skibinski, et al., Eur. J. Immunol. 28:3940-3948 (1998)). Lymphocytes within the lymph node also have a complex interdependence; for example, dendritic cells secrete factors that promote antibody production and B cell survival/proliferation (Dubois, et al., J. Exp. Med. 185:941-951 (1997)). All of the cell types that can be part of the LTE (including T cells, B cells, DCs, lymphoid stromal cells) have the potential to interact and influence one another.

Example 19

LTE Structure and Germinal Centers

The LTE serves as an important locus for activation of naive T and B cells. The present invention includes, in the design of the LTE, multiple approaches for fabrication of a model of the lymph node extracellular matrix and providing various microenvironemental cues (such as chemokines, cytokines, cells (e.g., fibroblastic reticular cells)). Specific design considerations for the LTE include:

1. using synthetic and/or natural lymphoid ECM derived hydrogel matrices as models of the reticular network 'scaffold' of the lymph node.
2. The role of matrix composition and presence of supporting lymphoid stromal cells on T cell activation and DC survival/function within the LTE.
3. Fabrication of LTE structures comprising both T and B zones. These will be assembled using several complementary strategies.
   a. Direct physical assembly of segregated T and B cell areas.
   b. Self organization and maintenance of T and B cell areas via creation of engineered local chemokine sources within distinct locations with the matrix.

The following description sets out in detail the experimental rationale and approach for each of these features of the present invention.

Clearly, the dynamic multi cellular interactions occurring during an immune response in the lymph nodes or other secondary lymphoid tissues represent a complexity significantly above anything attempted in an in vitro model of tissue or organ function to date, except in whole, ex vivo organ cultures. To manage the complexity of this problem, the present invention is limited to a model of aspects of lymph node physiology that are, relatively, quite well understood and likely important for basic functions of the lymph node.

Germinal centers represent one of the most complex and dynamic tissue microenvironment in the body; their function is as yet poorly understood. Affinity maturation occurring within germinal centers is an extremely complex process that is not well understood; both the stromal cells and follicular dendritic cells that are involved and local microenvironmental factors (cytokines, chemokines) remain poorly defined (Kosco Vilbois, Nat. Rev. Immunol. 3:764-769 (2003); Cyster, et al., Immunol. Rev. 176:181-193 (2000)).

The LTE of the present invention thus lacks any 'engineered' germinal centers or germinal center precursors. This choice is based on the following experimental observations. First, B cells from mutant mice (lymphotoxin-$\alpha$- or tumor necrosis factor-$\alpha$-deficient) lacking germinal centers are still able to undergo antibody isotype class switching and somatic mutation, and further produce high-affinity antibodies in response to antigen, suggesting that germinal centers are not absolutely required for affinity maturation (Matsumoto, et al., Nature 382:462-466 (1996); Pasparakis, et al., J. Exp. Med. 184:1397-1411 (1996)). Second, functional B cell memory (defined by rapid production of high titer IgG1 in response to antigen re-challenge) has been found to be intact in mice lacking Bc16, which also do not form germinal centers (Kosco-Vilbois, Supra (2003); Toyama, et al., Immunity 17:329-339 (2002)). Finally, in vitro studies have shown that B cells cultured with activated T cells (or surrogate cells providing CD40L signals) are capable of promoting a partial germinal center phenotype, isotype switching, and somatic mutations (Galibert, et al., (1996) J. Exp. Med. 183:77-85; Razanajaona, et al., J. Immunol. 159:3347-3353 (199&)).

Figure 26:
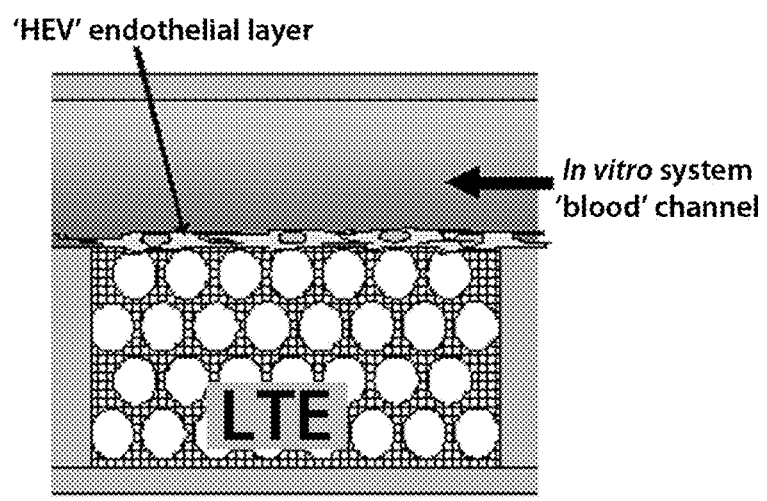
FIG. 26 shows a potential HEV model for the in vitro model immune system. A separate monolayer in the plane of the HEV surface would be composed of lymphatic endothelium to provide to separate access points to the LTE.

A second simplification in the LTE of the present invention is the lack of programmed naive T cell/B cell recirculation; cells loaded into the LTE are not exposed to structures mimicking high endothelial venules (HEV) that might promote exit from the lymph node during homeostasis. In vivo, T cells depart a given lymph node to recirculate among the various secondary lymphoid tissues via the blood every 24-48 hours. In an alternative embodiment of the present invention, an in vitro model of HEV monolayers atop the LTE structure is contemplated (FIG. 26). In a murine system, high endothelial cells have been isolated (Phillips & Ager, Eur. J. Immunol. 32:837-847 (2002); Rot, J. Immunol. Methods 273:63-71 (2003)).

In one embodiment, the LTE comprises a synthetic hydrogel 'inverse opal' matrix. Ordered macroporous hydrogels are prepared by pouring a poly(ethylene glycol) (PEG) dimethacrylate and PEG peptide PEG block copolymer solution over an ordered colloidal crystal of poly(methyl methacrylate) latex microspheres (monodisperse with diameters of about 5-150 μm) and UV polymerizing the gel (FIG. 27A). Microspheres are then leached out by brief treatment with acetic acid followed by extensive washing of the gel with phosphate buffered saline (PBS). Shown in FIG. 27B is an example of the ordered honeycomb like structures obtained by this method; the sequence of four smaller images is a 3D reconstruction of one "cell" of the scaffold in rotation, showing the "side ports" connecting this pore of the scaffold to its neighbors in the x-y plane. As illustrated in FIG. 60, scaffolds of arbitrary shape and dimensions can be synthesized, of both macroscopic or microscopic dimensions.

Use of peptide containing crosslinkers in the gel allows tailored ECM mimicking peptides, or complete ECM proteins as desired, to be included in the gel (FIG. 27C) (Irvine, et al., Biomacromol. 2:85-94 (2001); West & Hubbell, Macromolecules 32:241-244 (1999)). Adhesion sequences can also be included in the hydrogel to promote cell attachment and migration in the structure. In addition, the design incorporates enzyme sensitive cross linkers that allow cells to remodel the structure using native pathways (e.g., collagenase). With this system, well defined ECM mimetic structures with tailored pore size, mechanical properties, and biochemical composition are designed in.

To complement the above approach to fabricating a suitable matrix for the LTE, the present invention also includes a approach to fabricating hybrid synthetic/natural ECM structures, in which one can apply the colloidal crystal templating method to fabricating natural ECM scaffolds with a defined architecture. In these experiments, the hydrogel prepolymer solution in the templating step (FIG. 27A) can be replaced with ECM gel in its liquid form. The gel was subsequently solidified at 37° C. in the presence of the templating spheres, cross link the ECM in place covalently, and dissolve out the templating spheres with acetic acid. This approach combines the native biochemical structure of the ECM gel with the defined microstructure of the synthetic inverse opal structures.

Example 20

Microbeads Fabricated from Lymphoid Extracellular Matrix

Microbeads were fabricated from porcine lymphoid extracellular matrix prepared using a protocol provided by Dr. Stephen Badylak, University of Pittsburgh.

Figure 28:
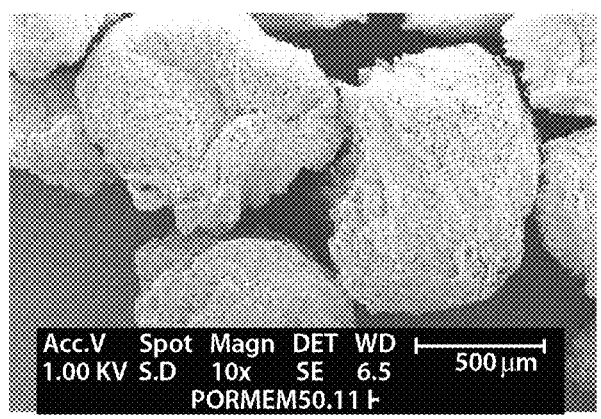
FIG. 28 shows image of microbeads fabricated from lymphoid ECM (80% w/w) and Protasan (20% w/w) by flash freezing, freeze drying, and gelation with tripolyphosphate.

A suspension containing ~10 mg/ml lymph node (LN) ECM microfragments in 2 mg/ml Protasan, pH 3.5, was sprayed over the surface of liquid nitrogen in a laminar, drop-by-drop mode, making droplets of about 1.5 mm in size. The frozen beads were then freeze dried overnight, incubated in 10% tripolyphosphate (TPP), pH 6.0, for 1 hour thereafter, then washed three times with deionized water over a 100 μm cell strainer, and were then freeze-dried again (FIG. 28).

Example 21

Loading LTE with Chemokine and Lymphocytes

In another embodiment of the present invention, the LTE comprises a microcarrier loaded with a chemokine and lymphocytes. Another embodiment of the invention relates to a method of constructing the LTE; said method comprises (1) providing matrix; (2) loading said matrix with a chemokine; and (3) cultivating lymphocytes with said matrix.

Figure 29A:
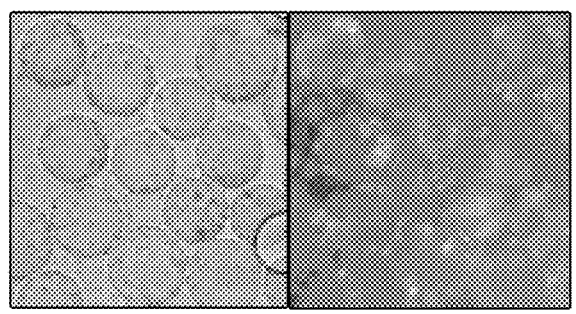
FIG. 29(A) shows image of B cells on Cytodex-1 microcarriers (Amersham), bright field microscopy (left) and fluorescence (right).
Figure 29B:
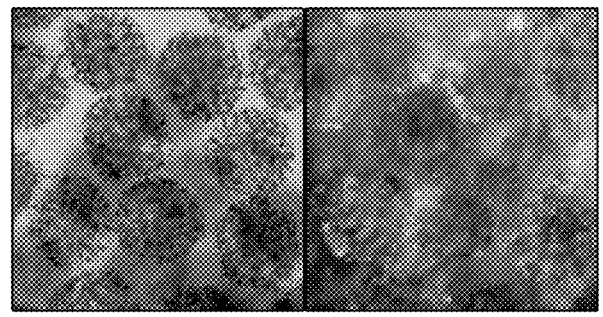
FIG. 29(B) shows image of T cells on Cytopore-1 microcarriers (Amersham), bright field (left) and fluorescence (right).
Figure 29C:
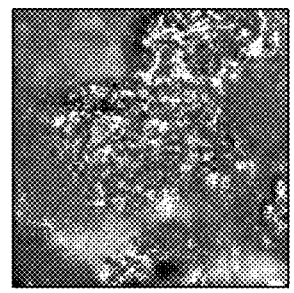
FIG. 29(C) shows confocal fluorescence image of T cells on LN ECM/Protasan in-house microcarriers.

In order to attach B and T cells to microcarriers, B and T cell fractions were negatively selected from peripheral blood lymphocytes using a magnetic bead-based separation protocol. Cell suspended in PBS were deposited onto various microcarriers and incubated for 1 hr. The microcarriers were then washed in PBS four times, and attached cells were revealed on the surface of carriers by the green fluorescence of the internalized CFSE stain (FIG. 29(A), (B), (C)).

The microcarriers can be saturated with chemokines. In one embodiment, CXCL-13 (BCA-1; BLC) and CCL-21 (SLC; Exodus-2) were chosen as basic B and T cell specific chemokines, respectively.

Many chemokines are strongly basic proteins; that is, they bear amino groups which are positively charged at neutral pH (Proudfoot, et al., J. Biol. Chem. 276:10620-10626 (2001)). On the other hand, many microcarriers also contain positively charged groups (e.g., diethyl aminoethyl fragments in Amersham products; amino groups in chitosan/Protasan). Consequently, to provide for proper attachment of chemokines, charge modification of the surface of the carriers is important.

As an example, this could be accomplished using polyanionic mediators that attach to positively charged microbeads and overcompensate the charge, according to the known mechanism of layer-by-layer (LBL) supramolecular assemblies (Kotov, NanoStructured Materials 12:789-796 (1999)), thus providing for subsequent reversible electrostatic attachment of positively charged chemokines.

Figure 30:
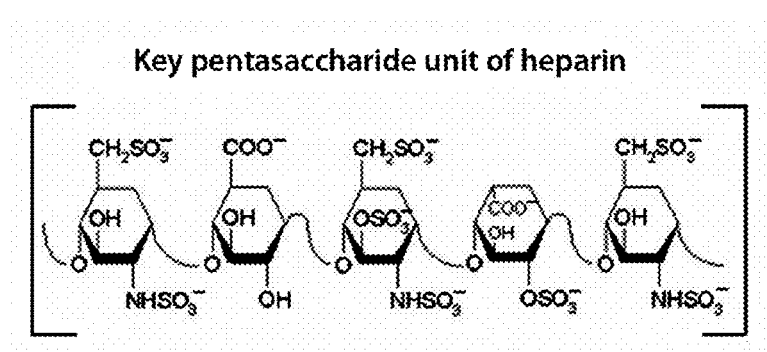
FIG. 30 shows the structure of heparin, a natural component of extracellular matrix. Heparin contains multiple pentasaccharide units bearing sulfate and carboxylic groups; the average charge per unit ratio is 2.3.

Heparin, a natural component of extracellular matrix, was chosen as a mediator. Heparin contains multiple pentasaccharide units bearing sulfate and carboxylic groups; the average charge per unit ratio is 2.3 (Sasisekharan & Venkataraman, Current Opinion in Chemical Biology 4:626-631 (2000)) (FIG. 30).

Figure 31A:
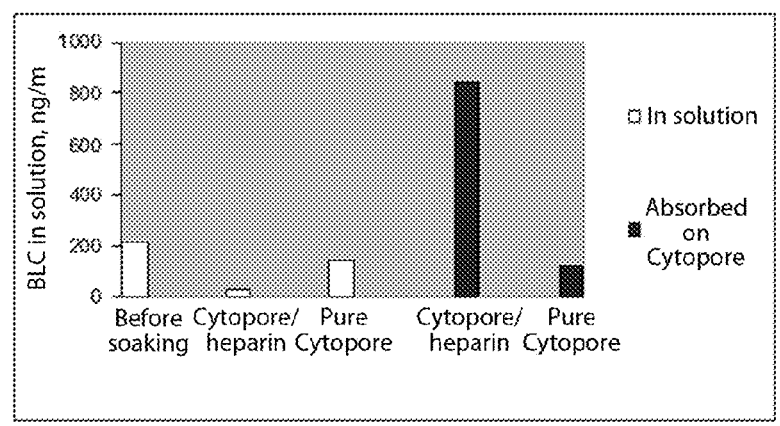
FIG. 31 illustrates that heparin-treated Cytopore possesses ample sorption capacity for the BLC chemokine (FIG. 31A), and steep time-release curve (FIG. 31B). Thus, it is a suitable carrier for B and/or T cells.
Figure 31B:
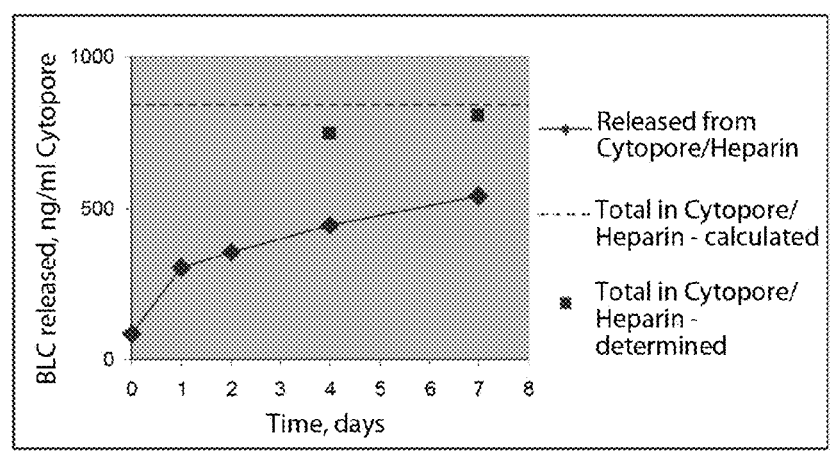

In an embodiment, cytopore-1 microcarriers (Amersham), 10 mg total, were soaked overnight in 1 ml PBS buffer containing 10 mg porcine heparin (Sigma-Aldrich); another portion of Cytopore-1 was soaked in the buffer containing no heparin. The samples were washed afterwards 7 times with copious volumes of deionized water and 1 time in PBS containing 0.1% bovine serum albumin (BSA), and transferred into glass tubes containing 2 ml PBS/BSA plus ~200 ng/ml BLC chemokine. Upon incubation overnight, the samples were analyzed for BLC remaining in solution and absorbed on Cytopore microcarriers using a one-step Quantikine ELISA kit (R&D Systems) (FIG. 31).

Example 22

Tissue and Matrix Effects on T Cell Activation in the LTE

Both the extracellular matrix and stromal cells of lymph nodes likely play significant roles in T cell, B cell, and dendritic cell function in the secondary lymphoid organs. From the standpoint of the cellular makeup of lymph nodes, stromal cells of the T zone are likely to play a significant role in T cell activation, via production of cytokines and/or chemokines, as well as the expression of receptors that support T cell and DC migration through the T zone.

Figure 32:
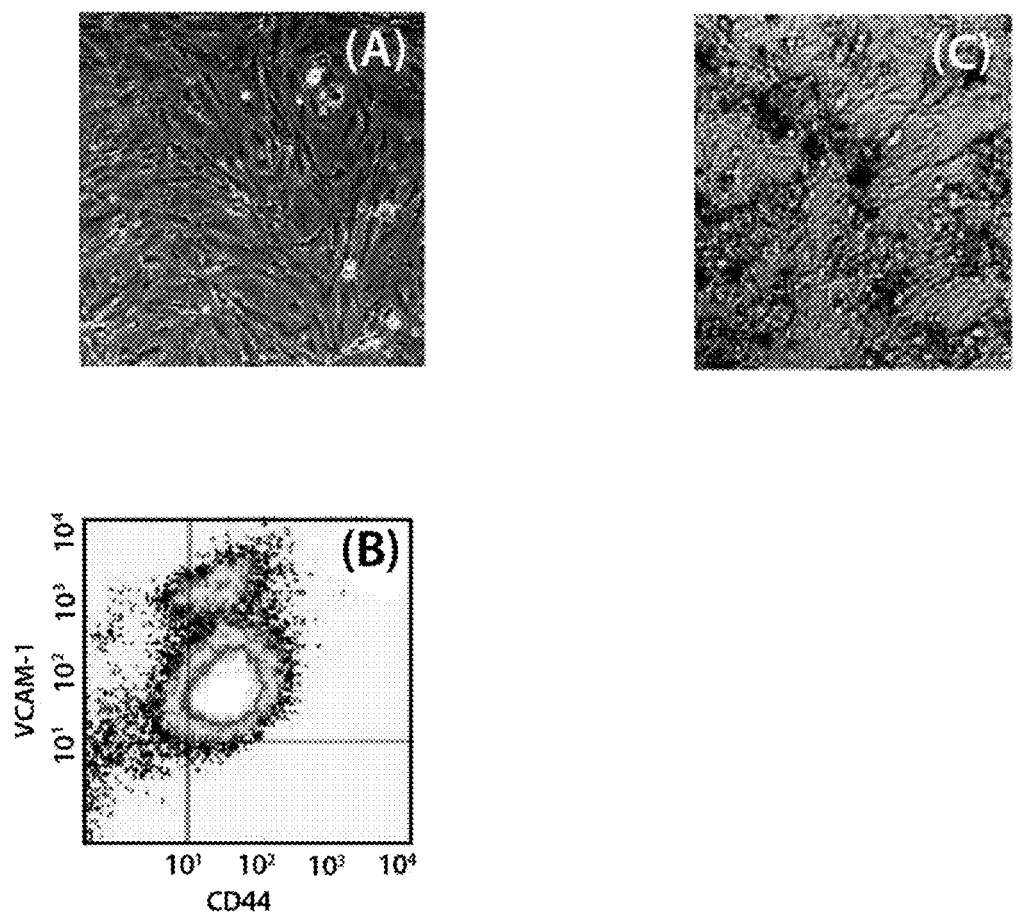
FIG. 32 demonstrates fibroblastic reticular cell line derivation. (A) phase contrast micrograph of a confluent monolayer of T zone FRCs in culture. (B) flow cytometry measurement of CD44 and VCAM-1 expression by FRCs. (C) micrograph of FRC growth on flat RGD-PEG hydrogel surfaces.

Derivation of T zone stromal cells. The design of the LTE in the present invention includes the engrafting of T zone fibroblastic reticular cells (FRCs, stromal cells of the T zone) on the hydrogel scaffolds. As an example, stromal cells were isolated from lymph nodes of C57BL/6 mice in a manner similar to previous reports (Bogdan, et al., J. Exp. Med. 191:2121-2130 (2000); Castro, et al., Eur. J. Cell Biol. 74:321-328 (1997); Skibinski, et al., Immunology 102:506-514 (2001); LeBedis, et al., Int. J. Cancer 100:2-8 (2002)) to test the response of these cells to our synthetic materials. The stromal cells thus obtained had a characteristic fibroblast-like morphology (FIG. 32A). Stromal cells of lymph nodes express high levels of CD44 and VCAM 1 (Skibinski, et al., Eur. J. Immunol. 28:3940-3948 (1998); Ruco, et al., Am. J. Pathol. 140:1337-1344 (1992)); flow cytometry analysis of FRCs stained with anti CD44 and anti VCAM 1 confirmed expression of these molecules by the stromal cell lines (FIG. 32B). Synthetic poly(ethylene glycol)-based hydrogels presenting RGD adhesion peptides supported the attachment, spreading, and growth of FRCs over several days in culture (FIG. 32C). These cells also grew well on fibronectin, collagen IV, and collagen I-coated surfaces, but not on laminin (data not shown).

Example 23

Assembly of T and B Cell Areas

To provide the lymph node function of T cell help for B cell antibody production, distinct T and B cell areas within the LTE of the present invention are fabricated by the combined action of digital printing (directly assembling T cells and B cells within distinct zones) and/or controlled release technologies (e.g., using microspheres releasing T and B cell attractants to maintain T and B cell areas, respectively). Together with the materials used to fabricate the matrix, this allows spatial and temporal control over the model lymphoid microenvironment, to properly tune cell migration and cell-cell interactions: both adhesion ligand and chemokine type, spatial location, density, and concentration with time can be varied to optimize lymphocyte functions. While full control over all of these variables provides the fullest mimic of the in vivo environment, as illustrated in the data given above for model LTE structures, some limited subset of adhesion molecule, chemokines, and other soluble factor information in the LTE can achieve significant functionality within these in vitro constructs.

Figure 33:
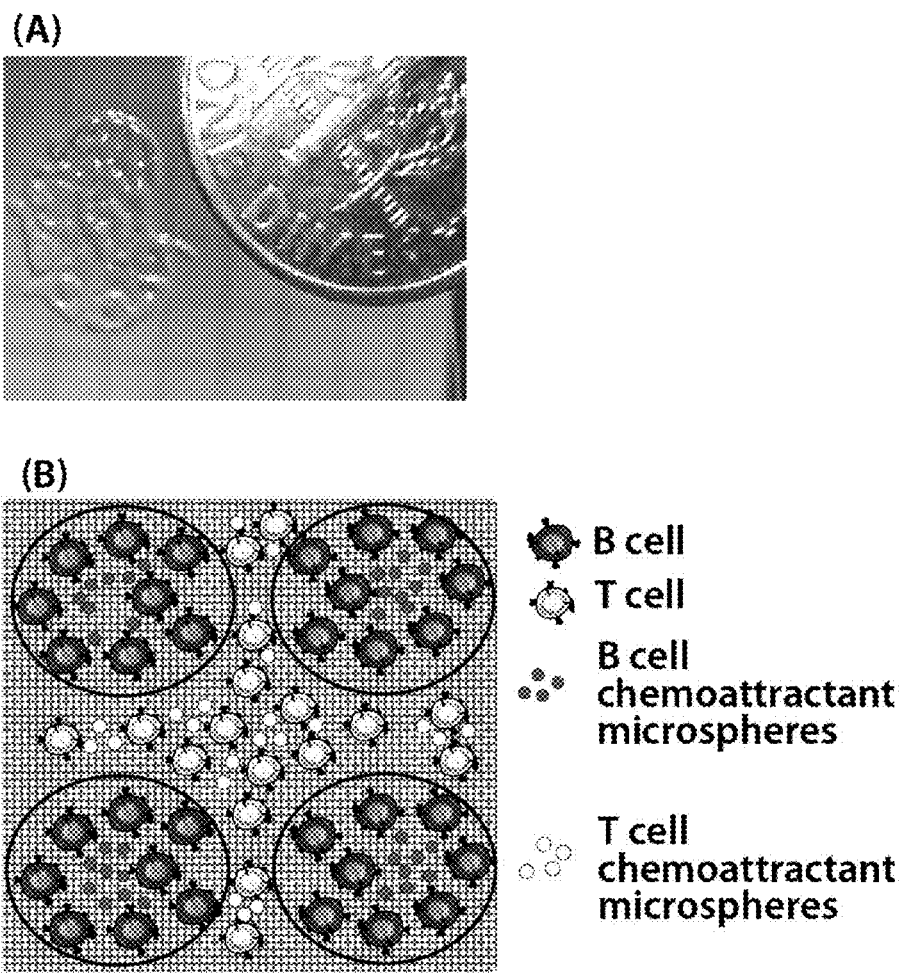
FIG. 33 illustrates a mock lymph node. (A) direct printing of a heterogeneous matrix. Example of a digitally-printed mock 'lymph node' structure. (B) schematic of digital printing assembly of heterogeneous LTE with T- and B-zones, using co-deposited controlled release microspheres to maintain lymphocyte localization.

Digital printing of heterogeneous LTE zones. The Bio-Assembly Tool (BAT) allows the deposition of viscous liquids, including live cell suspensions with micrometer scale precision, using computer control. Sequential depositions allow 3D structures to be built, as illustrated by the mock lymph node gel structure (FIG. 33A). The digital printing ability of the BAT is used to co-deposit lymphocytes with or without controlled-release microspheres into designated 'zones' within LTE scaffolds, comprising, e.g., the synthetic and/or natural ECM matrix examples described above.

Example 24

Maintenance of T and B Cell Areas Using Chemokines

T and B lymphocytes are highly motile, and one might expect that if the microenvironment of the LTE matrix supports migration, the T cell and B cell areas created by direct printing into the LTE will not remain well-defined over time in culture. In vivo, these zones are believed to be maintained by the action of local chemokine gradients that locally attract T and B cells to their respective compartments within secondary lymphoid tissues (Cyster, et al., Immunol. Rev. 176: 181-193 (2000); Cyster, J. Exp. Med. 189:447-450 (1999)) (FIG. 34A). To provide a defined simulation of these conditions in the LTE, an embodiment of the LTE of the present invention includes the co-deposition of cells with chemokine releasing microspheres, designed to provide a local center of gravity for each cell type in their local zone (FIG. 34B).

Distinct chemokines serve to organize the T cell and B cell areas of lymph nodes; CXCL13 (BLC) is known to be a key factor localizing B cells in lymph node follicles (Cyster, et al., Immunol. Rev. 176:181-193 (2000); Ansel, et al., Nature 406, 309-314 (2000)), while CCL19 (MIP-3β) and CCL21 (SLC) draw T cells and dendritic cells to the T zone (Cyster, J. Exp. Med. 189:447-450 (1999); Mebius, Nat. Rev. Immunol. 3:292-303 (2003)). In an embodiment of the present invention, lymph node fibroblastic reticular cells can be included in the T zone of the LTE to obtain a "native" source of chemokines to self organize the T zone of the scaffold. In another embodiment, the LTE includes controlled release microspheres to obtain defined chemoattractant depots within the LTE. For example, the use of degradable poly(lactide-co-glycolide) (PLGA) microspheres to chemoattract dendritic cells and monocytes using formyl peptides or the chemokine MIP-3β has been demonstrated. For self organization of the LTE, similar procedures can be used to encapsulate BLC, MIP-3β, and SLC in microspheres for controlled release within the LTE matrix. As both MIP-3β and SLC are involved in T zone organization, these can be included separately or in combination. One then can co-deposit microspheres with T cells and B cells into LTE scaffolds, and compare the maintenance of defined T cell and B cell areas within these structures over time in these chemokine directed scaffolds, compared with matrices that lack such microspheres. In another embodiment, it is possible to directly encapsulate microspheres within the 'struts' of the hydrogel matrix during polymerization. In still another embodiment, FRC-engrafted T cell areas can be prepared to determine whether these stromal cells can guide T cell localization within scaffolds.

Example 25

In Vitro Tissue Slice Templates

Additional approaches to constructing a functional LTE. The embodiments above describe an approach to fabricating a minimal, functional mimic of mammalian, preferably human, secondary lymphoid tissue. Other embodiments considered within the scope of the present invention are now described.

Figure 35:
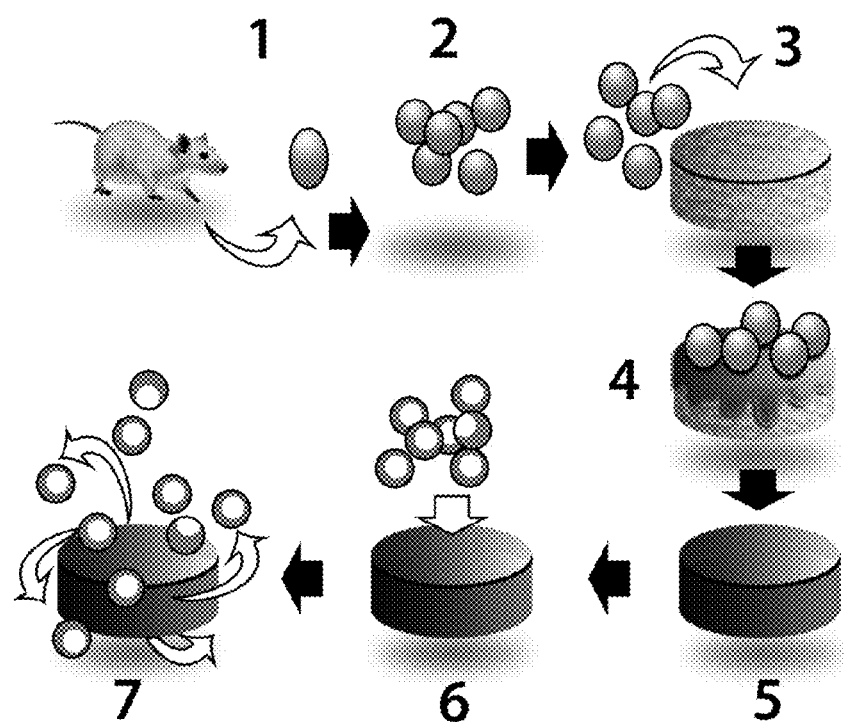
FIG. 35 shows an additional embodiment involving 'templating' the LTE using native human stromal cells in a manner similar to that reported by researchers attempting to create an in vitro artificial thymus (Poznansky, et al., Nat. Biotechnol. 18:729-734, (2000)).

Another embodiment involves 'templating' the LTE using native human stromal cells (FIG. 35), in a manner similar to that reported by researchers attempting to develop an in vitro artificial thymus (Poznansky, et al., Nat. Biotechnol. 18:729-734 (2000)). Their approach comprised the following steps:
1. small thymus fragments from mice were cultured on the surface of Cell Foam disks (a porous matrix) in 12-well plates and covered in growth media for 14 days until a confluent layer of stroma had formed throughout the matrix.
2. upon reaching confluence, human lymphocyte progenitor cells were added into the co-culture.

3. during co-culture for 4 to 21 days, non-adherent cells were periodically harvested and cell surface markers were analyzed to determine T lymphopoiesis.

Following a similar scheme, in an embodiment of the present invention, LTE matrices could be "templated" with stromal cells derived from lymph node fragments or lymph node, spleen, or tonsil "slices" to seed the construct with native stromal cells and provide a ready microenvironment for added T cells, B cells, and DCs. Such cocultures can be maintained in vitro using standard organ culture methods during the templating step, and the templated LTE can subsequently be loaded into the AIS bioreactor for continued maintenance. This approach not only provides an alternative for generating a correct lymphoid microenvironment, but also a complementary in vitro approach for analysis of lymph node formation and organizing principles.

Example 26

Sources of Cells to Populate the Artificial Immune System

To populate the in vitro immune system, a large number of cells, including monocytes, T and B cells, endothelial cells, fibroblasts, keratinocytes, stromal cells, as well as neutrophils, mast cells, and other immune cells may be needed. In one embodiment, a ready source of immune cells is peripheral blood (PBMC), which will provide many of the cells needed for the vaccination site and for the LTE. In another embodiment, skin related cells from human samples (described in the vaccination site section) can be used. In still another embodiment, it is possible to use the HuScid mouse as a source of hematopoietic cells that are generated from CD34+ stem cells in vivo. Additionally, as methodologies for generating all these cell types from embryonic stem (ES) cells are developed, the present invention is considered to include using completely matched cells derived from one ES cell strain/line.

Example 27

Bioreactor Design and Construction: Integration of the AIS Components

Drawing an analogy with high throughput drug screening technology, an AIS suitable for rapid vaccine or chemical screening will require multiple, low-cost, disposable bioreactors, designed for single-use. Each bioreactor will be challenged with a different antigen and, upon activation of the immune response, harvested for antibodies, B cells, and T cells. Microfluidic bioreactors are preferred for achieving this goal and provide the additional advantage of requiring fewer scarce cells for seeding tissue constructs.

Figure 36:
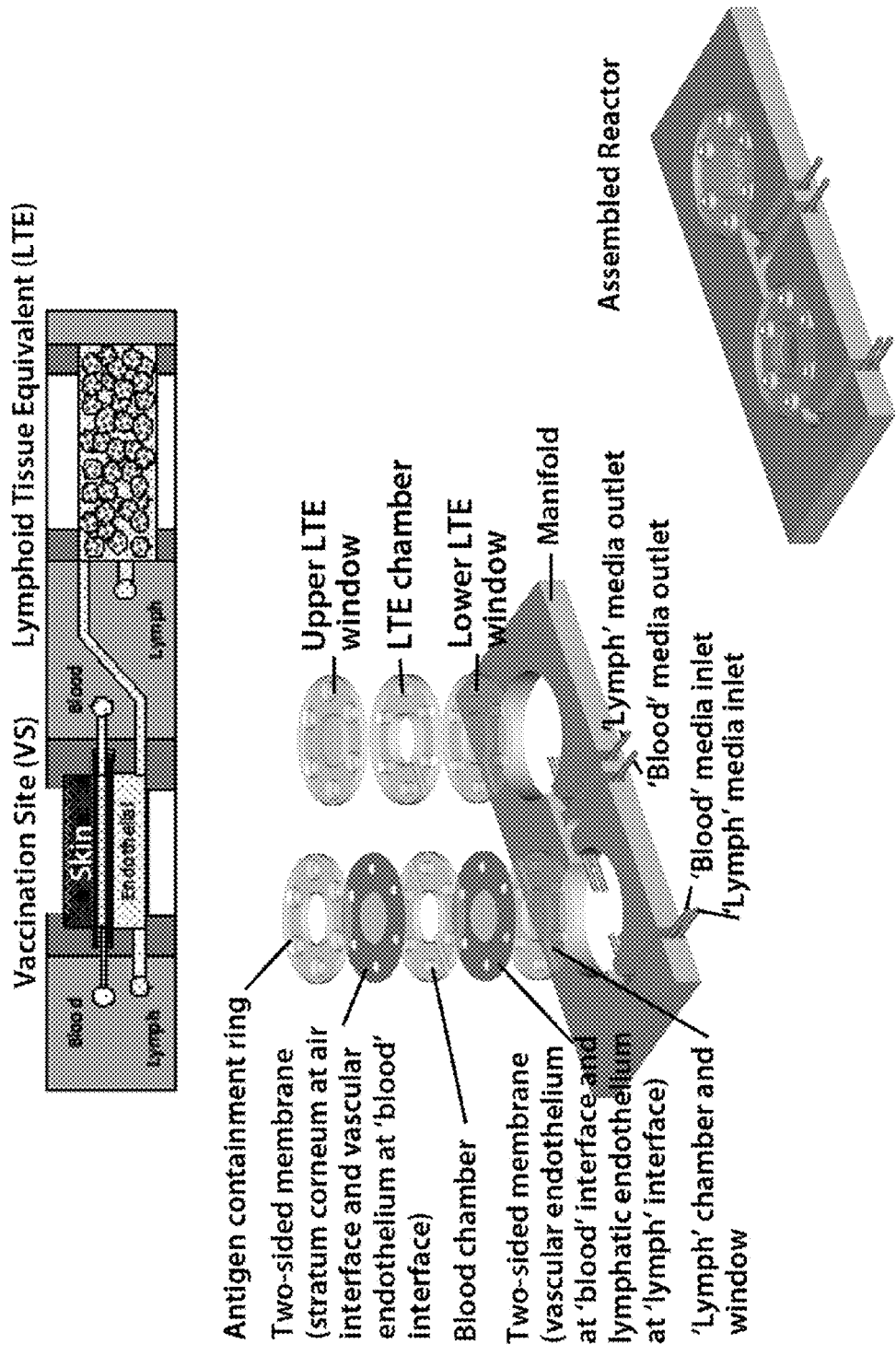
FIG. 36 is a schematic of a bioreactor.

As illustrated in FIG. 36, in an embodiment, the AIS bioreactor can be fabricated as a two-compartment microscope slide with a transparent polymer sheet or glass coverslip for microscopic examination. In a preferred embodiment, the physical dimensions of each immune bioreactor measure of the order of about 7.5 cm long and about 2.5 cm wide, with an overall thickness of about 2 mm or less. The first chamber contains the VS and LTE membranes that can be grown as modular units and later inserted into the lower structural layer or as a fully integrated system from the start. The second chamber contains the LTE, comprising T and B cell populations. If required, additional LTE constructs can be added to enable lymphoid organ trafficking or trafficking to other tissues. Syringe tube ports located on the upper layer permit injection of factors and/or cells at strategic positions along the vascular pathways and within ETCs. FIG. 48 shows a plan view of an example integrated bioreactor that shows micromachined blood vascular and lymphatic pathways with high contact area beneath the VS and LTE ETCs.

Figure 37:
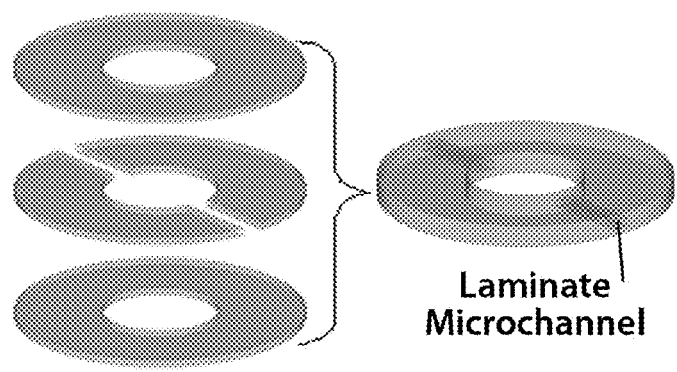
FIG. 37 shows a laminate based insert whereas a larger milled tubular design is incorporated in to the design illustrated in FIG. 36.

To promote interaction between cells migrating along the blood vascular and lymphatic pathways and in the VS and LTE tissue constructs, the contact spacing between each tissue membrane can be adjusted by using, e.g., machined inserts or thin laminates that have small, integrated microchannels. Suitable construction materials include biologically compatible polymers, such as polycarbonate, polyethylene, or acrylic. A laminate-based insert is as shown in the example (FIG. 37), where as a larger milled tubular design is incorporated in to the design illustrated in FIG. 36. In a sense, these designs mimic a thin venule pathway that supports lymphocyte migration from peripheral blood into secondary lymphoid organs.

Nutrient-rich media is pumped from an external media reservoir through the channels, flowing tangentially past the VS and LTE constructs, and back to the reservoir. Nutrient and waste product transport between the recirculating media and the tissue constructs occurs through both diffusional and convective (Starling flow) processes.

Figure 38:
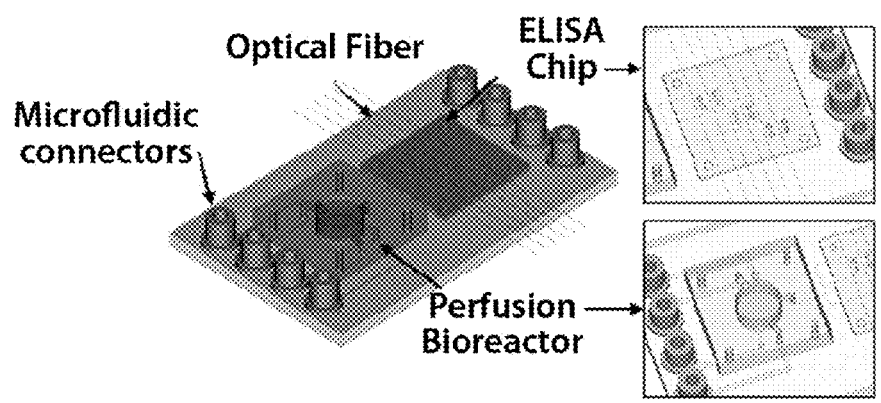
FIG. 38 shows an example microfluidic bioreactor with optical diagnostics on microfluidic backplane.

In contrast to other nutrients, oxygen is only sparingly soluble in cell culture media. Consequently, high perfusion rates may be required to sustain a sufficient oxygen supply and to avoid developing necrotic zones. Should required perfusion rates exceed physical capabilities (e.g., unusually high pressure drops can compromise the integrity of bioreactor seals) or generate excessive fluid shear, in alternative embodiments, the oxygen tension in the media may be increased by, for example, using an O2 microexchanger in-line with the circulating blood media. By circulating the blood media over gas permeable polymers, exposed to high oxygen concentrations on the opposite side, the O2 environment can be adjusted to compensate for any O2 consumption and loss. Monitoring and making adjustments to the O2 concentration in the bioreactor can be accomplished using commercially available non contact fluorescent probes to provide feedback to an oxygen air supply. Creating a high concentration gradient between the gaseous oxygen at the polymer interface and the tissue construct, can facilitate diffusional transport and culturing of thicker constructs. An example of an assembled construct with transparent covers for optical inspection/fluorescent imaging is shown in FIG. 38.

Example 28

Fabrication and Assembly of Layered AIS

Fabrication of such microfluidic bioreactors may require ultra short pulse machining trials with the biocompatible materials to determine optimum processing conditions (such as laser fluence and translation speed). The design of the present invention is sufficiently flexible to allow laser machining of a layered device (e.g., gas permeable polymer top layer, BAT deposited middle layer, and PDMS bottom layer) for additions of vias or ports after the device has been assembled.

FIG. 49 shows cross sectional views of direct deposition in an embodiment of an AIS device. Various biomaterial structures can be incorporated as constituents of the artificial immune system (e.g., bio concrete, inverse hydrogel opal, colloidal particles, ECM gels, collagen gels, microcarriers). For example, a polymeric mesh rebar can be deposited layer by layer directly in the recessions of the VS and LTE areas. In such a design, it is preferred to have the lower plate of the AIS unit made of polyacrylate, polystyrene, or another transparent plastic sensitive to DM, to allow the mesh rebar to attach to the plate. In this embodiment, the surface will be micropatterned using KOH in a manner similar to the ESC scaffolds. Fibrin gel matrix bearing all necessary nutrients and cytokines will be used to coat the threads of the mesh as a thin film, leaving sufficient space for cell accommodation and motion.

As shown in FIGS. 50 and 51, the design of the present invention is sufficiently flexible to allow laser machining of a layered device (e.g., gas-permeable polymer top layer, BAT-deposited middle layer, and PDMS bottom layer). FIG. 52 provides a schematic diagram of a perfused bioreactor system with the associated external pumps for the lymphatic and blood vascular loops and external media reservoirs. The AIS bioreactor can be operated in either semi-batch or continuous mode.

In an embodiment of the present invention, integration of membranes in the bioreactor is achieved by crimping the membranes between thin metal (e.g., stainless steel) rings, as illustrated in FIG. 53. Using such a crimping method, biological membranes can be supported without use of adhesives and can be pressed into a disk with thickness profile of about 400 µm or less.

FIG. 54 shows the fabrication of a 3-layer planar waveguide. FIG. 55 shows an example device comprising a perfusion bioreactor, ELISA chip with integrated optical waveguides, microfluidic backplane to connect and allow swapping of devices and microfluidic connectors for external pumps and reservoirs.

In addition to machining channels directly, molds can be machined in suitable materials to create a reusable master from which PDMS devices may be formed. This will allow a higher volume of devices to be fabricated than laser machining in serial. Channel encapsulation methods will be evaluated to provide a leak-proof construct. The materials that comprise the device will likely be damaged at high temperatures, so robust, low-temperature bonding methods will be needed.

Testing of the devices will require fixtures for mounting and providing external connections. Laser machining can also be used to provide manifolds for these test fixtures that would support fast swapping of devices without the need to disconnect external pumps or reservoirs. Equipment for measuring pressure, flow resistance and flow rate can also be connected to the devices via the manifold. Revisions to optimize the channel geometries can be made based on this data and performance of the ETCs.

The AIS microfluidic bioreactor system can be placed in an incubator that maintains constant temperature, humidity, and carbon dioxide control. Phenol red can serve as a colorimetric pH indicator in the media, so that pH can be monitored, e.g., periodically through visual inspection or photometric determination with logging capabilities. In another embodiment, pH can be monitored continuously and precisely in the external media reservoir with a pH probe and recorder.

Design of the flow channels to control shear forces is important to aid in cell migration through the membrane and to minimize cell stress or damage. Studies and modeling have shown that by applying shear forces in a controlled range near 2.5 dynes/cm2, lymphocyte migration across an endothelial membrane can be improved (Cinnamon, et al., Nature Immunol. 2:515-521(2001)). It has also been shown that elevated shear rates on the order of 70 dynes/cm2 can damage cells and alter cell function (Moazzam, et al., Proc. Natl. Acad. Sci. USA 94:5338-5343 (1997); Johnson, Biophys. J. 67:1876-1881 (1994); Hochmuth, J. Biomech. Eng. 115:515-519 (1993)). Channels dimensions in the bioreactor are preferably modified to create minimal shear stresses. Preferably, the inlet ports are maximized in size while the flow channel across the membrane is reduced to localize the shear forces at the membrane interface and reduce the shear forces in the injection ports. By increasing the shear forces at the membrane interface, cell migration can be improved and cell alteration can be eliminated.

Creating insert supports for both synthetic and natural membranes has been accomplished by using laminates, crimped rings, and adhesives (FIG. 19). Laminates and adhesives have primarily been used to support polymer meshes, which in turn are provide mechanical strength to synthetically formulated biological membranes. Fabrication using the laminate comprises sandwiching a stretched mesh between two pieces of polymer laminates, which are then thermally sealed together. The adhesive method comprises stretching a mesh support and adhering a stainless steel ring using a biocompatible glue. The crimping method, discussed earlier, comprises compressing the membrane between two stainless steel rings. Generally, the laminate and adhesive methods are limited to synthetic mesh-supported membranes, while the crimping method can accommodate both natural biological membranes and synthetic meshes.

Example 29

Optically Diagnostic AIS Microfluidic Bioreactor

Immunology has many cascades of events that cannot be observed in any human system at this time. In particular, if a vaccine fails as a result of a rate-limiting step related to entry into and interactions within an immunological tissue, there is presently no method to measure or improve this process in humans. To address this problem, an embodiment of the present invention include building the AIS in such a way as to be able to optically monitor in situ the steps of the in vitro immunological/vaccination process.

In one embodiment, integrated optical waveguides become part of a micro-total analytical system (µTAS) of the AIS, with many different functions including optical excitation, absorption, fluorescence, and imaging on a single microfluidic bioreactor system. An in situ diagnostic system will make optimization and conducting diagnostic evaluations of the immunological constructs more rapid. Two-photon fluorescence can enable visualization of immunological events in all three dimensions in both artificial and living tissues. This technique can aid in understanding and optimizing the effects of various adjuvants, vaccine candidates, drugs, biologics, biomolecules, and antigen presentation vehicles in vitro and with in situ diagnostics.

Prototype results are presented regarding fabrication of µTAS that can be used to perform the immunological analysis steps in situ, to simplify the process and reduce analysis time. In one embodiment, the present invention provides an AIS device with the addition of integrated optical waveguides for in situ optical diagnostics. These waveguides provide optical excitation and detection pathways for colorimetric analyses (such as ELISA assays, absorption and fluorescence analysis).

In this example, single layer, planar polymer waveguides were fabricated using selective femtosecond laser ablation of a polymer substrate. A glass slide was coated with an 80 µm-thick layer of a single part, ultraviolet curing polymer with a refractive index of 1.56. After curing for 30 minutes with a ultraviolet (UV) lamp (4 W), planar optical waveguides and microfluidic channels were machined into the polymer using a Ti:sapphire femtosecond regime laser. The optical waveguides and microfluidic channels were each approximately 100 µm wide by 80 µm deep. Light from a CW Nd:YVO4 laser was coupled to the planar waveguides through a 50 µm core diameter optical fiber inserted into a tapered alignment groove as shown on the left. Light guided through the planar waveguides passes through an intersecting microfluidic channel. This waveguide/channel intersection is shown in the middle with the laser source off and on the right with the laser source on. Light entering the channel from the right is collected in the waveguide on the opposite side of the channel. This light is then coupled to another 50 µm core optical fiber and sent to a silicon detector for measurement.

Example 30

In Situ Diagnostic Bioreactor Development

Microfluidic devices that mimic in vivo systems are proving valuable in studying cell interactions and biological processes in vitro. Such devices offer several advantages over traditional large-scale fluidic assemblies including small sample and reagent volumes, small waste volumes, increased surface area-to-volume ratios, low Reynold's numbers (laminar flow), fast sedimentation for particle separation, reduced reaction times, and portability. Some microfluidic devices also integrate pumps, valves, filters, mixers, electrodes, and detectors. The ease of alignment and shorter reaction times make near real-time detection possible using this approach.

Fabrication of microfluidic devices has relied mainly on technology developed in the microelectronics industry, such as photolithography and subsequent etching of silicon or glass. These technologies often require multiple processing steps and clean room facilities and can take days or weeks to produce a working device; they are better suited to mass production of devices than rapid prototyping. A relatively new method of fabrication is ultra-short pulse laser micromachining (USPLM). USPLM has the advantage that materials can be machined directly without the need for masks or photoresist development. Devices can therefore be fabricated more quickly, often in a day or less, permitting rapid prototyping. Furthermore, due to the extremely short pulse duration (<150 fs) and high intensities, almost any material can be readily ablated because of multiphoton absorption and ionization, even if it is transparent at the laser wavelength. This is especially useful in machining materials for an optically transparent bioreactor. FIG. 46 shows an ultra-short pulse laser micromachined planar optical waveguides integrated into microfluidic channel. Left panel: Tapered port for fiber optic coupling. Middle panel: microfluidic channel intersection of planar waveguide (source off). Right panel: microfluidic channel intersection of planar waveguide (source on, entering from right).

Figure 39:
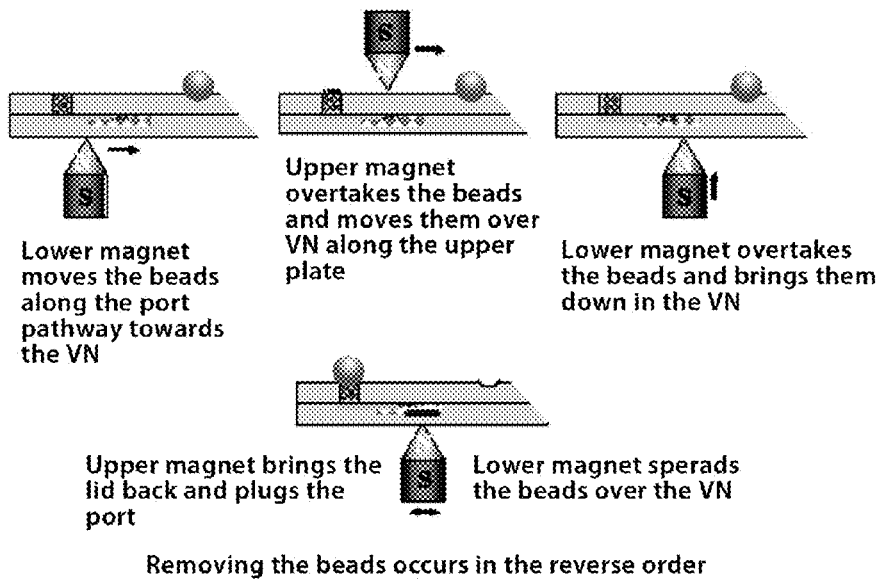
FIG. 39 shows an embodiment of the MaAIS.
Figure 40:
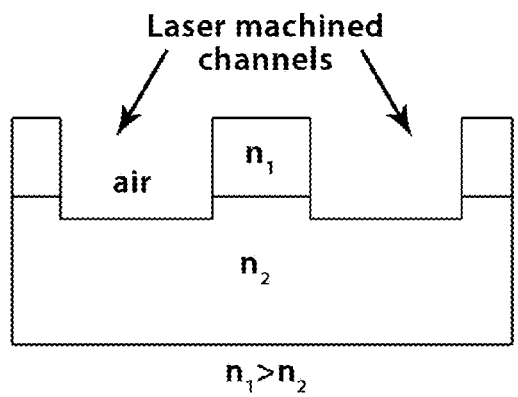
FIG. 40 shows laser machined integrated optical waveguides: $n_1$ represents the refractive index of the waveguide core, $n_2$ is the cladding index.

In an embodiment of the present invention, USPLM was used to machine microfluidic channels, vias, reservoirs, and integrated optical waveguides in the bioreactors. An inexpensive and widely used biocompatible silicone elastomer, polydimethylsiloxane (PDMS), comprises the main body of the structure. Sheets of PDMS can be patterned by USPLM and then assembled to form the 3D construct (Laser-machined microfluidic bioreactors with printed scaffolds and integrated optical waveguides, Nguyen, et al., Proc. SPIE Int. Soc. Opt. Eng., 5591). The layers may be either permanently bonded by treating with oxygen plasma or temporarily bonded by applying mechanical pressure. Thus, fabrication of disposable or re-usable devices is easily accomplished In one embodiment, integrated optical waveguides are fabricated as illustrated in FIG. 39 The waveguides comprise multiple alternating refractive index polymer layers in which the middle polymer layer has the higher refractive index. In preferred embodiments, the polymers can be either UV or thermal cured or a combination of both (e.g., PDMS cladding and UV curing core). The waveguides are defined by removing material on either side using an ultra-short pulse laser. The laser can also be used to integrate tapers for fiber optic coupling to the waveguides. Microfluidic channels are machined either parallel or perpendicular to the waveguides. Light is launched into a waveguide on one side of the microfluidic channel, passed through the channel where it interacts with the fluid in the channel and then collected by the waveguide on the opposite side of the channel and sent to a detector. In another embodiment, fiber optics are embedded into PDMS and then microfluidic channels machined perpendicular to the fibers, removing a small section of the fiber in the channel. This eliminates the need for planar polymer waveguides and fiber-to-waveguide coupling losses at the expense of elaborate waveguide geometries, such as splitters and combiners FIG. 40.

FIG. 59 shows an example bioreactor construction with collagen membranes on rings and support matrix. Collagen cushion congealed at 37° C. for 1 hour remained highly stable with no collagen degradation for more than 3 weeks. Panel A shows the bioreactor design. Panel B shows progression from the whole bioreactor to the level of the collagen matrix cushion within the mesh. After the HUVEC cells have reached confluence on the collagen cushion, the bioreactor is assembled under sterile conditions (Panel C). Once assembled, media flow is initiated.

Example 31

Imaging System

Understanding a complex living system requires a thorough comprehension of the interactions of cells and their 3D microenvironment. Understanding those cells will necessitate an integrated understanding of all functional units, signal transduction molecules, structural scaffolding, and genetic material.

Imaging is a powerful unifying tool for such studies. Specifically, in an embodiment of the present invention, confocal microscopy and two-photon fluorescence can be integrated in a transparent bioreactor that houses the vaccination site (VS) and lymphoid tissue equivalent (LTE). Light-microscopic analyses of fluorescently tagged markers may provide important information about the location and behavior of proteins, as well as many details of protein-protein interactions. At relatively low resolutions, confocal microscopy can produce three-dimensional (3D) images of fluorescently tagged gene products to determine their distribution in the cell during different stages of the cell cycle or under various environmental conditions. Such information allows insights into cell and organelle biology. Furthermore, confocal microscopy permits analysis of the ETC 3D architecture, which cannot be achieved by conventional light microscopy. The broad goal is to visualize cellular constituents and general cytoarchitecture in a state as close to native organization as possible. As an example, confocal microscopy can be used to investigate the DC maturation state in vitro using integrated, optically transparent bioreactors, where the fiber waveguides are integrated into the bioreactor.

A need exists to image many biological processes in 3D at the vaccination site construct. For this, 3D confocal imaging of polymer samples can be conducted using two-photon excited fluorescence. Fluorescent molecules may absorb two photons simultaneously before emitting light. This phenomenon is referred to as "two-photon excitation." Using two-photon excitation in a conventional microscope provides several advantages for studying biological samples, including efficient background rejection, low photo-damage, and depth discrimination. A relatively long wavelength of the excitation source (e.g., 798 nm from a mode-locked Ti:Sapphire laser) can be used to enable a larger penetration depth into the 3D ETC than provided by conventional single-photon fluorescence confocal microscopy.

Two-photon confocal microscopy, in conjunction with highly efficient fluorophores, is useful as a tool to study the surface, interface, and inner dimensions of the in vitro vaccination site (VS) and LTE. It can provide diagnostic information to aid in understanding features such as cell motility towards the VS and within the VS, cell differentiation, and cell maturation to enable optimization of various DC activities.

Several biomarkers are of interest for monitoring in the system. These include IL-12 (secreted by DCs when they mature: inhibits migration of DCs), IL-4 (Th2-like responses), CD40, CD40L, CCR7 (migratory chemokine receptor), IL-1β (inflammatory chemical secreted by immune cells), TNF-α, and VEGF (important modulator of monocyte differentiation into macrophages or DCs.

Example 32

Complete Design of AIS Device

An example AIS device is illustrated in FIG. 38. The device comprises a microfluidic bioreactor, ELISA chip with integrated optical waveguides, microfluidic backplane to connect and allow swapping of devices and microfluidic connectors for external pumps and reservoirs. The bioreactor has four external ports, two each above and below the tissue construct. An ELISA chip with three sets of two channels is illustrated, though more channels are contemplated in the same footprint in other embodiments. In each set, one channel is for a sample assay and the other is a control with no sample. Each set is attached to the same ELISA input port, allowing both channels to be prepared simultaneously; however, only one channel in a set is attached to the sample fluid. This fluid is pumped from the bioreactor to the ELISA chip through a channel in the microfluidic backplane. Valves control the addition of the sample fluid to each channel. Light is coupled to the ELISA channels through optical fibers and the transmitted light is coupled to another fiber attached to a detector. In this preferred embodiment, the bioreactor and ELISA chips are both optically transparent for two-photon and confocal microscopic examination. In this preferred embodiment, the footprint of the entire assembly in this example is approximately 50×75 mm.

Example 33

Magnet Assisted AIS

In a further embodiment the functionality of the AIS is enhanced using magnetic microbeads or nanobeads (the magnet assisted AIS, MaAIS). Because the AIS allows monocyte and DC transport between compartments (blood, skin, lymph node) to be accounted for, biomimetic pathways for migration to and from the immunological constructs in the AIS will lead to new insights in vaccine design and better predictive power for the AIS. The two vascular highways are the blood to move monocytes to the VS and lymphatics to move mature DCs from the VS to the LTE.

Guided monocyte and DC migration between compartments via chemoattractants in the flow loops of the bioreactor (with sources at the VS and LTE, respectively) mimic the natural trafficking properties of these cells in vivo, a "biomimetic" solution. In another embodiment, magnetic microbeads and electromagnetic fields can be used as a means to directly move cells between compartments of the AIS, an "engineering" solution.

Magnetic beads are commonly used as a tool for cell separation, sorting and assay, where the carrier particles bind cells specifically, usually via antigen antibody interactions, or using streptavidin biotin coupling. Magnetic beads typically consist of a magnetite ($Fe_3O_4$) or other paramagnetic core of 1-5 μm coated with biocompatible polymers, to which the affinity groups can be covalently attached. Products of DYNAL (Norway) are, however, macroporous polystyrene particles that are magnetized by in situ formation of magnetic material inside the pores (Safarik & Safarikova Rev. J. Chromatog. B 722:33-53 (1999); DYNAL (Norway) http://www-.dynalbiotech.com/). The micron size of the magnetic particles annuls their ferromagnetism (i.e., the ability to retain magnetization after removal of the field) so the beads do not cluster.

Localization and separation of these paramagnetic beads is simple and straightforward; moderate magnetic fields, typically from hundreds to thousands of Gauss, and readily attainable field gradients are sufficient for this (DYNAL (Norway) http://www.dynalbiotech.com/). Many types of magnetic beads surface grafted with various antibodies, as well as with streptavidin, protein A, and other anchoring groups are available commercially (Safarik & Safarikova, Rev. J. Chromatog. B 722:33-53 (1999); DYNAL (Norway) (http://www.dynalbiotech.com/); AGOWA GMBH (Germany) http://www.agowa.de/struktur/magneticbasis.html). When assembled in a confined pool, the beads can be readily transported in aqueous solutions by movement of a pointed magnet. These features allow magnetic beads to be used to perform various tasks in a micro bioreactor, such as selection of cells with appropriate surface markers (receptors; epitopes), transporting selected cells from one area to another; and bringing cells into contact with a desired environment, including other cells. The use of trafficking magnetic and other field controlled beads in chemical and biological analyses and syntheses has been recently elaborated in Oestergaard & Bankenstein (1999) WO patent application No. WO 99/49319. This approach can be taken a step further. In another embodiment of the present invention, bead trafficking can be implemented in the design of the AIS.

In this additional embodiment, the magnet assisted AIS includes the following important features:
1. the in vitro device will remain a single unit, preferably flat, with its major elements located in a single isolated volume.
2. most of the available volume will remain filled with, and periodically recirculated with media containing necessary nutrients, signal molecules and gases.
3. most of the cell trafficking will be directed, with specific beads used as vehicles (random traveling of cells will be greatly reduced).
4. the beads will be moved by means of pointed permanent or electromagnets, preferably along the lower surface of the upper plate of the flat in the MaAIS construct.

5. major signaling and activation molecules, such as chemokines, maturation signals, antigens can be delivered to the cells by special beads in a controlled fashion, if desired.
6. the order of events and the routes of magnetic trafficking can be controlled by computer.

The MaAIS bioreactor is an extension of the "biomimetic" AIS system. In an embodiment, the construct is a transparent, flat two plate sandwich. The lower plate harbors specific areas for the VS and LTE sections. These latter elements can be machined as flat depressions in the lower plate, preferably filled with, e.g., bioconcrete components, regularized PCL mesh, and matrix (ECM; suitable materials include collagen, fibrin clot, Dermagraft). The plates have special ports for the delivery and/or evacuation of the magnetic beads. The beads can be brought to the ports by computer-controlled deposition heads, similar to those in the BAT. The plates have recirculation channels to provide media flow. How the system can be used is schematically illustrated in FIG. 39.

DCs can be attached to the magnetic beads and moved only when the maturation process is complete. This can be achieved using microbeads functionalized with antibodies against mature DC surface markers, (e.g., CD83, in human cells, which are commercially available).

To allow mature DC-specific labeling of cells exiting the VS after antigen uptake, magnetic particles functionalized with antibodies against markers upregulated upon DC maturation can be used (including, for example, CD83 (in human cells), CD80, and CD86). In another embodiment, pan-DC markers, such as CD11c, can be used to traffic all DCs (mature or not) exiting the VS endothelium into the AIS bioreactor pathway.

Figure 42:
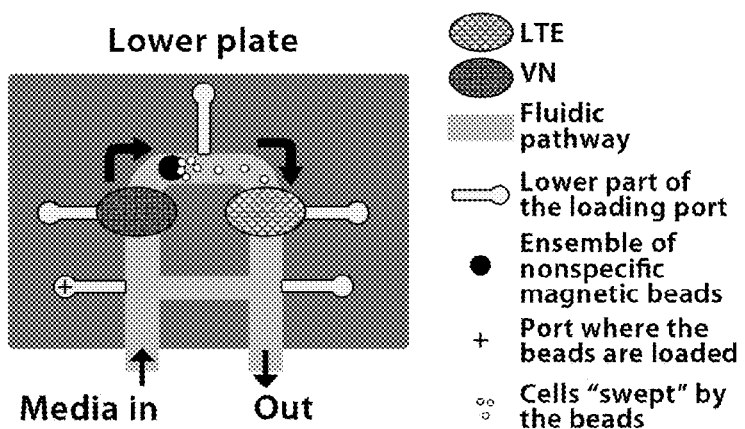
FIG. 42 is a schematic of a "Magnetic broom" used to move cells from VS to LTE.

Magnetic beads can be also used as nonspecific locomotives, facilitating cell travel in the fluidic channels of the AIS. An ensemble of magnetic beads sufficiently numerous to partially or substantially fill the cross section of the fluidic channel can be forced by a computer controlled magnet to travel around the circular route of the fluidic channel, moving any particulate object along with them. If the beads are coated with biocompatible materials and the speed of their movement is sufficiently slow (low Re numbers), then they can assist cell movement via collisions with cells without damage (FIG. 42). In some cases, this kind of trafficking may be preferable, as no specific receptors on cells will be involved, minimizing the risk of modulating cell state.

Example 34

Magnetic Bead-Based ELISA for Rapid in situ Read Out of AIS Function

There are at least two parameters of the immune response to be assessed in the AIS: the titer of specific antibodies produced by activated B cells, and the total quantity and the ratio of the activated T helpers and cytotoxic T cells (that is, the CD4/CD8 response). In an embodiment, magnetic beads can also be used at this stage, to provide a rapid, computer-controlled, and magnetically actuated assay.

Introduced in the early 1990s (Luk & Lindberg, J. Immunol. Meth. 137:1-8 (1991); Gundersen, et al., J. Immunol. Meth. 148, 1-8 (1992)), the so-called Immuno Magnetic Separation ELISA (IMS-ELISA) has drawn recent attention and is now a fast and sensitive immunoassay method (Chou, et al., J. Immunol. Meth. 255:15-22 (2001); Kourilov & Steinitz, Anal. Biochem. 311:166-170 (2002)). For example, Kourilov & Steinitz used magnetic beads as solid phase platforms for the attachment of the antibodies to be determined, instead of customary ELISA plates (Anal. Biochem. 311: 166-170 (2002)). Secondary antibodies raised against the primary antibodies and tagged with, for example, alkaline phosphatase or peroxidase were used to titrate the primary targets. This general scheme provides a mechanism for performing the assay in the AIS device in a potentially fully automated and facile microscale mode.

Example 35

Phagocytosis

Figure 41:
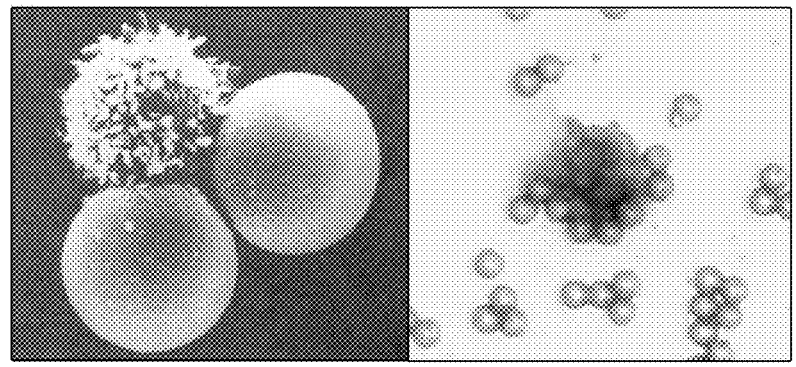
FIG. 41 shows images of cells captured using Dynabeads M450. Left: T-lymphocyte (from Safarik & Safarikova, Rev. J. Chromatog, (1999) B, 722:33-53; DYNAL (Norway); Right: MCF-7 breast cancer cell (from Sieben, et al.).

Phagocytosis reportedly depends on the size and surface properties of the particles in question. In general, microparticles in the size range of about 1 to about 3 μm, those that are more hydrophobic; and those bearing positive surface charges are most likely to be engulfed. Particles bigger than about 5 μm or smaller than about 1 μm, those that more hydrophilic, and those bearing negatively charged surfaces are not readily engulfed by DCs (Chen, et al., J. Colloid Interface Sci. 190: 118-133(1998)). Consequently, large and appropriately coated particles can be used to minimize or effectively stop phagocytosis. The biggest Dynabeads particles produced by DYNAL (Norway) are about 5um (Safarik & Safarikova, Rev. J. Chromatog. B 722:33-53 (1999); DYNAL (Norway) http://www.dynalbiotech.com/). Much larger beads (10 μm and bigger) are available, from, e.g., AGOWA (AGOWA GmbH (Germany) http://www.agowa.de/struktur/magneticbasis.html). Even bigger magnetic beads, structurally resembling the Dynal products, can be synthesized from chitosan (Banchereau & Steinman, Nature 392:245-252, (1998)). FIG. 41 illustrates M450 Dynabeads attached to the cells of differing type and size. Mature DCs are approximately the size of the tumor cell captured on the right of the figure, about 30 to 35 μm (Sieben, et al. Comparison of different particles and methods for magnetic isolation of circulating tumor cells). As a consequence, it is hard to expect them to be able to phagocytose beads of, say, about 20 μm size or bigger. FIG. 56 show the phagocytosis of microparticles by a monocyte.

Phagocytosis can also be minimized by temporarily decreasing the temperature of the VS of the AIS to 4° C. This can be achieved, for example, using a miniature thermoelectric element.

In another embodiment of the present invention, phagocytosis can be allowed to occur, and the cells that have internalized cell specific magnetic nanoparticles/microparticles can then be moved using a magnet. Magnetic beads made by Dynal (Norway), and by other manufacturers, contain the magnetic material as a minor component of the beads; 80% or more of the weight, and, accordingly, more than 90% of the volume is occupied with biocompatible material (Safarik & Safarikova, Rev. J. Chromatog. B 722:33-53 (1999); DYNAL (Norway) (http://www.dynalbiotech.com/); Denkbas, et al., Reactive & Functional Polymers 50:225-232 (2002)), which can be made biodegradable without loss of other useful properties of the beads. Magnetite ($Fe_3O_4$) is biocompatible.

Example 36

Stimulators of the AIS

The AIS design allows the introduction of peptides or proteins derived from common pathogens or vaccines, including influenza, CMV, or tetanus toxoid. Such antigens can be injected directly into the in vitro VS. In addition, different adjuvants or stimulators of the innate immune system can be introduced to trigger dendritic cells and other cells to be activated and induce T and B responses in turn.

Example 37

Measuring Immune Responses in the AIS

After DCs, T and B cells have interacted from about 1 to about 7 days, cells can be extracted from the LTE to assess their properties in detail. In addition, the liquid phase of the LTE and the VS can be sampled to measure antibody titers and cytokine/chemokine levels.

(a) T cells: A preferred direct method for gauging antigen specific T cell activation is tetramer staining. Tetramer technology can be used to quantify antigen specific responses if the AIS is populated with cells of a defined HLA type for which there are available tetramers (e.g., HLA-A*0201 MP peptide for influenza responses) (Larsson, et al., J. Immunol. 165:1182-1190 (2000); Danke & Kwok, *J. Immunol.* 171: 3163-3169 (2003)). T cells can then be stained using the appropriate MHC class I or II tetramer. In addition, they can also be co-stained intracellularly for cytokines (such as IL-2, IFN-γ, IL-4) to assess effector functions of CD4+ T cells. Additionally, CD8+ T cells can be further tested for their ability to lyse target cells pulsed with the same peptide.

For antigens for which associated tetramer staining reagents are not available, traditional restimulation approaches can be used to test for an increase in antigen specific T cells, by, for example, looking for [$^3$H]-thymidine incorporation in response to antigen-pulsed, syngeneic dendritic cells. In addition, cytokine production can be measured by, for example, ELISPOT and intracellular staining, and CTL lysis by standard target lysis methods. A more general method that can be used to study T cell proliferation is staining input T cells with CFSE dye, which allows quantification of cell division by measuring CFSE dilution using flow cytometry (Hasbold, et al., *Immunol. Cell. Biol.* 77:516-522 (1999)).

(b) B cells: In parallel, B cell responses and antibody titers in the 'serum' or fluid of the artificial immune system can be measured (c) Dendritic cells: Dendritic cells can be isolated from about several hours to about several days after immunization and tested for, for example, viability, maturation marker expression, and functionality. It is anticipated that DCs will change their properties, depending on the initial vaccine stimulus.

(d) Cytokines and chemokines. It will also be important to assess the levels of key cytokines (including IFN-γ, IL-12, IFN-α, IL-2,) and chemokines (including ELC, BLC) that are present during the cascade of vaccine action, to gauge the efficacy of a vaccine.

Example 38

Titration of Vaccine-Specific Antibodies

Figure 43:
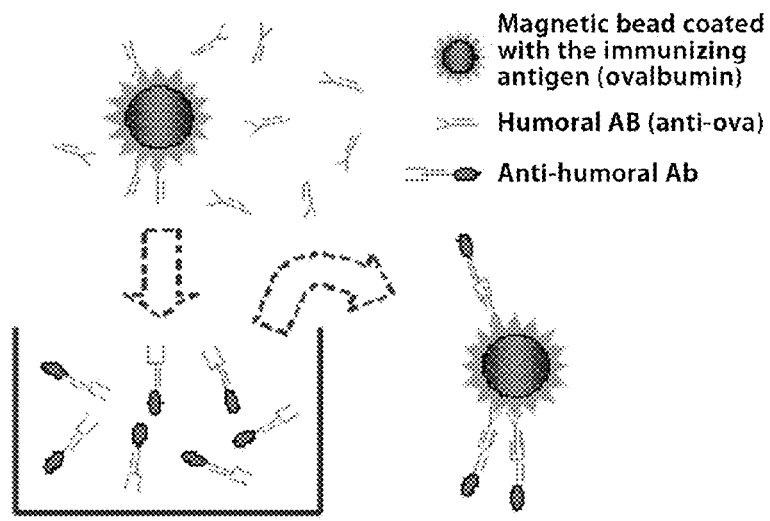
FIG. 43 is a schematic showing magnetic bead assisted ELISA of antibodies in the LTE compartment.

B cells cultivated in the LTE are expected to produce antibodies (Abs) in response to the immunization of the AIS device with a tested vaccine. Magnetic beads tagged with the antigen of immunization (e.g., ovalbumin) should bind to these antibodies. Secondary antibodies raised against the primary Abs and tagged with enzymatic or fluorescent reporting groups can be used to form a traditional ELISA sandwich, allowing determination of the level of the primary Abs (FIG. 43).

Example 39

Titration of the CD4/CD8 T cells

Figure 44:
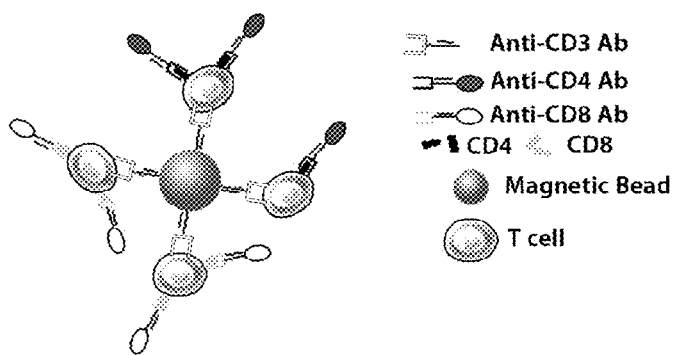
FIG. 44 is a schematic showing hypothetical hyper conjugate of the anti CD3 magnetic bead with CD4+ and CD8+ T cells and fluorescent anti-CD4 and anti-CD8 antibodies.
Figure 47A:
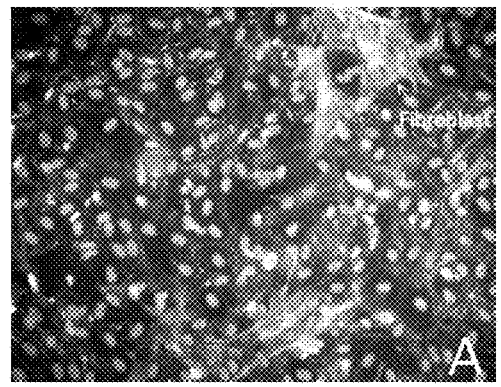
FIG. 47 is a composite of pictures showing seeding of endothelial cells on both sides of an amniotic membrane.
Figure 47B:
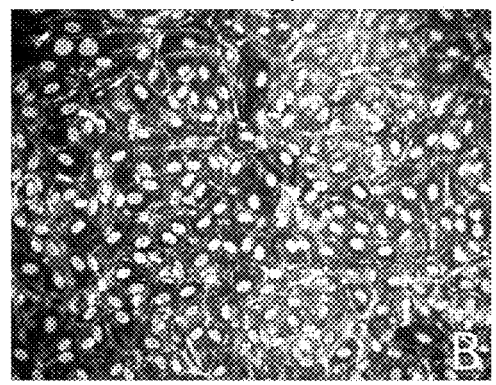
Figure 47C:
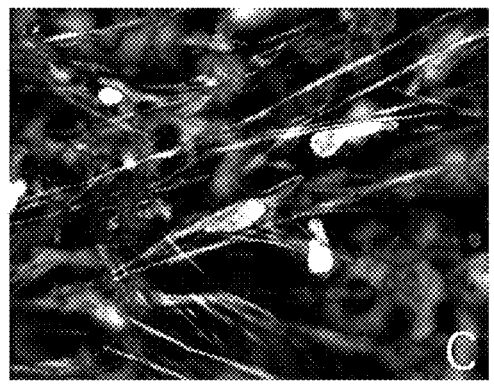
Figure 47D:
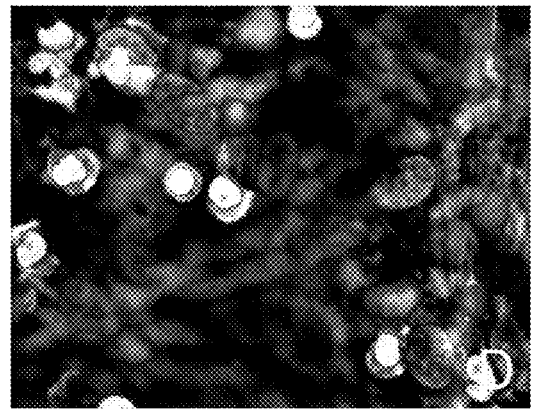
Figure 47E:
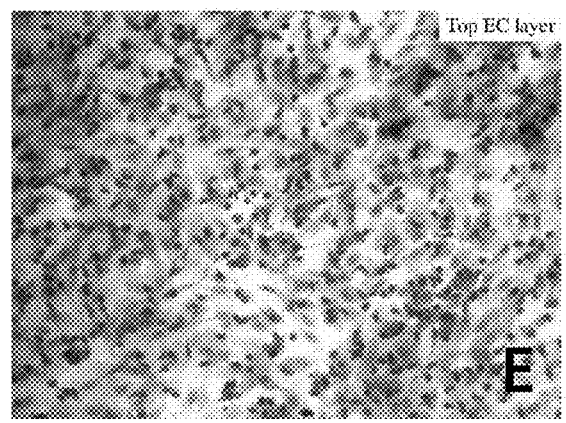
Figure 47F:
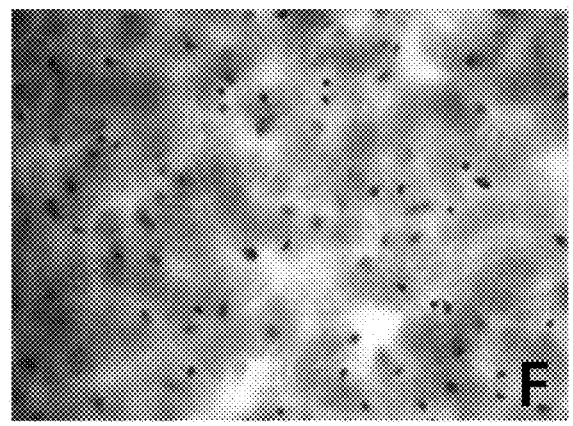

Appearance of the CD4+ and CD8+ markers on T cells is an outcome measure of their DC-induced activation. To employ an IMS-ELISA sandwich scheme for a CD4/CD8 assay, it is important to anchor the activated T cells to magnetic beads; this can be achieved using CD3 or CD2 activation markers. It is known, however, that binding antibodies to these markers per se typically initiates activation of T cells, which is undesirable in the assessment of T cell activity. On the other hand, the time period necessary to activate T cells via Ab attachment to CD3 is about 2 to 4 days (Protocol for anti-CD3 activation of T cells from E-Bioscience (San Diego, Calif.) (http://www.ebioscience.com/ebioscience/appls/AC145.htm#human)). Consequently, an assay performed in a significantly shorter time will likely still be informative. A magnetic bead/T cell conjugate formed via attachment of the bead to CD2 or CD3 will be a target for anti-CD4 and anti-CD8 antibodies tagged with specific labels, preferably with fluorescent groups (FIG. 44).

In general, more sophisticated and less routine multi target assessments of T and B cell activity can be performed for the AIS device with the aid the magnetic beads and sandwich ELISA techniques.

Example 40

Rapid Vaccine Assessment: How the AIS Can be Used to Assess Vaccines

A more accurate in vitro model for the assessment of human vaccines for, e.g., bio-warfare agents, emerging infectious diseases, and current global epidemics, is presented. The following example illustrates how the AIS can be used to assess efficacy and mechanisms of vaccines and other immunotherapies.

Traditional vaccine formulation starts with attenuation of a viral or bacterial strain, to reduce infectivity and pathogenic effects, while preserving immunogenicity and adjuvanticity Important features of a vaccine are thus to provide target antigenic epitopes for neutralizing antibodies and for CTL responses and adjuvant activity to stimulate a potent B and T cell memory response. However, there is no formula for reliably designing optimal epitopes or adjuvants; it remains largely empirical. The AIS can aid in discovering the rate-determining steps in vaccine efficacy and providing data to enable improved vaccine design and formulations.

A use of the AIS is in rapid screening of vaccine formulations to find optimal methods for antigen delivery and adjuvant stimulation of a human immune response. In particular, with the AIS, the efficacy of a vaccine can be tested in a more physiological context, thus providing an improvement over the predictive power of current testing methodologies. The activity of vaccines at each step of the vaccine life cycle can be measured, thus helping to determine which steps are important for vaccine success and failure.

Using the AIS, it is possible to quantitatively assess T and B cell stimulation in the context of more physiological environment than that found in a tissue culture dish or a non-human animal. Specifically:

1. by providing a venue in the LTE for DCs, CD4+ T, CD8+ T and B cells to meet, it can be determined whether a candidate vaccine promotes optimal levels of T cell help to induce CTL and B cell responses;

2. by allowing DCs, T and B cells to meet in a 3D environment with extracellular matrix and support cells, the LTE more realistically mimics the environment of the lymph node where the triad of cells interact in vivo;
3. the inclusion of endothelium ensures that monocytes and DCs interact with endothelial cells during recruitment and emigration; these interactions require the expression of specific proteins on the surface of immune and endothelial cells, some of which may be sensitive to the vaccine candidate and thus affect vaccine efficacy in humans; and
4. the presence of a more representative population of cells and of cells that must migrate across the endothelium and differentiate in response to local tissue signals, will lead to more accurate results (for example, it will be possible to distinguish the effects of TLR9 (Tol-like receptor 9) ligands versus TLR4 ligands as they are expressed differentially on multiple DC subtypes that may not be present in 2D cultures and that are known to be different in their Tlr expression in mice (Kadowaki, et al., *J. Exp. Med.* 194:863-869 (2001)).

The AIS of the present invention allows more accurate readouts because it contains a representative distribution of different cell types, opportunities for typical cell-cell interactions, basal activation states of cells that mimic cells in living tissues, and a more natural 3D extracellular matrix to support cell behavior and function.

The AIS enables the measurement of many important early and acute parameters of the response in the VS, and later parameters of the response in the LTE. Such measurements would be almost impossible to make in human clinical trials. The ability to measure many parameters will allow identification of steps that differ between vaccine candidates and will enable rational change and optimization of the vaccine candidate.

Measurements that can be made with the AIS include:
1. monocyte recruitment;
2. differentiation of DC subtypes;
3. DC antigen loading;
4. DC maturation;
5. DC emigration;
6. endothelium activation and function;
7. kinetics and numbers of DCs arriving into lymph node;
8. efficiency of interactions between T cells and DCs;
9. efficiency of interactions between B cells and DCs;
10. efficiency of interactions between T and B cells and DCs; and
11. activation status of T and B cells.

Differences in efficacy among vaccine candidates may be due to their differential ability to modulate any one of these or other steps. Identification of the steps that differ in successful and failed vaccines will allow a more rational model of how vaccines work.

For example, FIG. 45 shows the role of CCR8 in monocyte immigration in both in vitro and in vivo models. In panels A and C, monocytes were co-cultured with endothelial cells grown on a type I collagen gel for 48 h, permitting the separation of the population into reverse-transmigrating DCs or macrophages that remain in the subendothelium. Inclusion of neutralizing anti-CCR8 mAb 3B10 during the assay period when monocytes traverse endothelium in the apical-to-basal direction had no effect (panel A), but 3B10 anti-CCR8 mAb and anti-CCR8 mAb 5B11 significantly inhibited reverse transmigration in more than 5 independent experiments (panel C). In panels B and D, green fluorescent latex microspheres were injected into the skin of CCR8-deficient mice that were compared to age- and sex-matched wild-type C57BL/6 counterparts. This method traces monocyte conversion into DCs that present antigen in draining lymph nodes. Ungated day 1 skin analysis shows the cell suspension recovered from the site of injection. Fluorescent latex is found in a population of infiltrating monocytes in both wild-type and CCR8 knock-out mice. The number of DCs bearing 2 or more latex particles in the draining lymph nodes was quantified 3 days later. To combine data from different experiments, the mean number of migrated cells in wild type mice was set equal to 1.0 for each experiment and relative values for all wild type and knock-out individuals in that experiment were calculated. Lymph node dot plots show MHC II (I-Ab) and Gr-1 levels in lymph nodes and skin of wild type and CCR8−/− mice. These are quantitative comparisons, as they depict the entire population of latex-bearing cells recovered from pooled brachial lymph nodes from individual mice.

Example 41

Utilizing AIS as a Biofactory

In an embodiment of the present invention, the assembled LTE is used as a "biofactory," biosynthesizing various desired biomolecules (such as cytokines, proteins, antibodies). For example, if an antigen is presented to B cells, they can create antibodies in the LTE. Potentially, the created antibodies could also be monoclonal, depending on the repertoire of B cells and how the peptide is presented to the B cells. Monoclonal antibodies (mAb) are used extensively in basic biomedical research, in diagnosis of disease, and in treatment of illnesses, such as infections and cancer. Antibodies are important tools used by many investigators in their research and have led to many medical advances.

Example 42

T Cell Motility Induction in Inverse Opal Scaffolds

Among the multiple factors influencing naive T cell migration, adhesion molecules and chemokines play a significant role, and inclusion of the correct balance of these factors in an inverse opal hydrogel LTE allows naive T cell motility, quantitatively similar to in vivo cell migration, to be stimulated. As an example, fluorescently-labeled, mature murine dendritic cells (generated from the bone marrow of C57BL/6 mice by the method of Inaba, et al., J. Exp. Med., 176:1693 (1992) and matured by treatment with LPS for 12 hrs) and labeled naive CD4+ T cells from the lymph nodes of OT-II transgenic mice were added to inverse opal scaffolds coated with fibronectin. It is postulated that chemokines produced by mature dendritic cells (e.g., CCL19), and adhesion molecules expressed on the surface of these cells would promote naive T cell motility. Time-lapse 3D videomicroscopy was used to record the dynamics of cells within the scaffold over 2 hrs. T cells were highly active and exhibited 'start-stop' migration patterns reminiscent of migration behavior observed by intravital imaging studies of T cell migration in mouse lymph nodes. As shown in FIG. 61, T cells could migrate from void to void over the surface of dendritic cells in the scaffold, both vertically (FIG. 61A), and laterally (FIG. 61B). Quantitation of the cell paths and velocities (FIG. 62) showed that the cells moved with an average velocity of 4.6 µm/min, approaching the values reported in vivo for naive T cells, and that T cells had maximal bursts' of speed up to 30 µm/min, as seen in vivo. Naive T cells alone at lymph-node-like densities in inverse opal scaffolds failed to polarize or migrate (FIG. 63), indicating the need for a more complete lymphoid microenvironment to stimulate cell migration.

Example 43

Sorption Capacity of Heparin-Saturated Cytopore

Cytopore aliquots (0.4 ml, tightly sedimented) were treated with heparin and thoroughly washed and incubated in different concentrations of BLC in 3 ml PBS/BSA and washed. Afterwards, BLC remaining in solution and BLC absorbed by Cytopore/heparin were determined separately. As shown in FIG. 67, the sorption curve of Cytopore/heparin appeared sufficiently linear. Consequently, the conditions used were likely far from saturating the Cytopore with the BLC chemokine. This suggests Cytopore saturated with heparin as described, can potentially carry much higher (~10 times or more) loads of chemokines than in the example experiments.

Example 44

Kinetic in Silico Modeling of T and B Interaction in LTE

As shown in FIG. 57, B and T cells were modeled in 2D space as physical objects endowed with capability to walk randomly and come in physical contact with each other for a certain time. It was found that at a reasonably high concentration, for example at $\sim 3 \times 10^7$ cells/ml, the LTE model containing microcarriers as centers of self-concentration of B cells and T cells randomly walking around has an advantage towards the model of randomly distributed and co-cultured B and T cells: T cells had sufficiently higher probability to come in contact with B cells in the LTE model. This advantage gradually decreased with further increasing the cell concentration, and became negligible at concentration $\sim 3 \times 10^8$ cells/ml, which correspond to dense slurry of cells (FIG. 57). This computational result is considered circumstantial evidence in favor of LTE designs containing areas of concentrated B cells (mimicking the germinal centers of the natural lymph node) and loosely migrating T cells.

The above description is for the purpose of teaching the person of ordinary skill in the art how to practice the present invention, and it is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for assaying immunogenicity of a test agent comprising:
    a) loading a vaccination site comprising a first matrix and a plurality of cells attached to said matrix with blood monocytes and non-monocytic dendritic cell precursors;
    b) contacting the blood monocytes and non-monocytic dendritic cell precursors in the culture of a) with a test agent;
    c) culturing the culture of b) under conditions promoting conversion of the blood monocytes and non-monocytic dendritic cell precursors into mature antigen-presenting cells;
    d) transferring the mature antigen-presenting cells of the culture of c) to a three-dimensional artificial lymphoid tissue comprising a second matrix and a plurality of lymphocytes;
    e) culturing the culture of d) under conditions promoting stimulation of the lymphocytes by the mature antigen-presenting cells; and
    f) evaluating a response by the lymphocytes to stimulation by the mature antigen-presenting cells, wherein said response correlates with the immunogenicity of the test agent.

2. The method of claim 1, wherein the evaluating comprises comparing a lymphocyte response in the culture of f) with a lymphocyte response from an equivalent culture to which the test agent was not added.

3. The method of claim 1, wherein the lymphocyte response is evaluated by detecting the presence or measuring the level of a lymphokine.

4. The method of claim 1, wherein the lymphocyte response is evaluated by detecting the presence or measuring the level of a plurality of lymphokines.

5. The method of claim 1, wherein the lymphocyte response is evaluated by measuring one or more of (i) T cell and/or B cell activation, (ii) T cell and/or B cell proliferation, and (iii) antibody production by B cells.

6. The method of claim 1, wherein the test agent is select from the group consisting of a vaccine, an adjuvant, a drug, a biomolecule, a chemical and a cosmetic.

7. The method of claim 1, wherein the test agent is a vaccine.

8. The method of claim 1, wherein the first matrix comprises a natural biopolymer selected from a group consisting of type I rat tail collagen, bovine type I collagen and chitosan.

9. The method of claim 1, wherein the first matrix comprises bovine type I collagen matrix deposited and congealed on a nylon mesh.

10. The method of claim 1, wherein the first matrix is selected from the group consisting of xenographic extracellular matrix (ECM) sheet, natively polymerized human amniotic connective tissue, reconstituted collagen matrix and chitosan/collagen membrane scaffolds.

11. The method of claim 1, wherein the plurality of cells in the vaccination site comprises vascular and lymphatic endothelial cells.

12. The method of claim 1, wherein the plurality of cells in the vaccination site comprises human skin-derived vascular endothelial cells.

13. The method of claim 1, wherein the plurality of cells in the vaccination site comprise human vascular endothelial cells (HUVECs).

14. The method of claim 1, wherein the artificial vaccination site further comprises a chemokine.

15. The method of claim 1, wherein the second matrix comprises synthetic extracellular matrix (ECM) materials or natural ECM materials.

16. The method of claim 1, wherein the second matrix comprises microbeads fabricated from lymphoid ECM.

17. The method of claim 1, wherein the second matrix comprises segregated T cell and B cell zones.

18. The method of claim 17, wherein the T cell zone comprises naive T cells and collagen fibers.

19. The method of claim 18, wherein the collagen fibers comprise collagen I, collagen III or fibronectin.

20. The method of claim 17, wherein the T cell zone comprises fibroblastic reticular cells.

21. The method of claim 17, wherein the segregated T cell and B cell zones are fabricated by digital printing.

22. The method of claim 17, wherein the segregated T cell and B cell zones are fabricated by controlled release of chemoattractants.

23. The method of claim 17, wherein the segregated T cell and B cell zones are fabricated by combined action of digital printing and controlled release of chemoattractants.

24. The method of claim 1, wherein the plurality of lymphocytes comprises T cells and B cells.

25. The method of claim 24, wherein the plurality of lymphocytes further comprises dendritic cells.

26. The method of claim 1, wherein the plurality of lymphocytes comprises naive T cells and naive B cells.

27. The method of claim 1, wherein the plurality of lymphocytes comprises memory T cells and memory B cells.

28. The method of claim 1, wherein the plurality of lymphocytes comprises B cells and T cells negatively selected from peripheral blood lymphocytes.

29. The method of claim 1, wherein the artificial lymphoid tissue further comprises a chemokine.

30. The method of claim 29, wherein the chemokine is selected from the group consisting of CXCL-13, CCL-21 and MIP3.

* * * * *

UNITED STATES PATENT AND TRADEMARK OFFICE
CERTIFICATE OF CORRECTION

PATENT NO. : 8,722,402 B2
APPLICATION NO. : 13/608579
DATED : May 13, 2014
INVENTOR(S) : Warren et al.

Page 1 of 1

It is certified that error appears in the above-identified patent and that said Letters Patent is hereby corrected as shown below:

In the Specification

Column 1, Lines 17-26, the paragraph STATEMENT REGARDING FEDERALLY SPONSORED RESEARCH should be changed to:
-- STATEMENT OF GOVERNMENT LICENSE RIGHTS
This invention was made with government support under grant numbers DAMD17-02-1-0562 and DAMD17-02-1-0137 awarded by the Army Medical Research and Materiel Command, CA083856 awarded by the National Institutes of Health, and contract number NBCHC060058 awarded by the Defense Advanced Research Projects Agency. The government has certain rights in the invention. --

Signed and Sealed this
Fourteenth Day of April, 2020

Andrei Iancu
*Director of the United States Patent and Trademark Office*